(12) United States Patent
Bando et al.

(10) Patent No.: US 10,150,735 B2
(45) Date of Patent: *Dec. 11, 2018

(54) LOW HYGROSCOPIC ARIPIPRAZOLE DRUG SUBSTANCE AND PROCESSES FOR THE PREPARATION THEREOF

(71) Applicant: OTSUKA PHARMACEUTICAL CO. LTD., Tokyo (JP)

(72) Inventors: Takuji Bando, Tokushima (JP); Satoshi Aoki, Tokushima (JP); Junichi Kawasaki, Tokushima (JP); Makoto Ishigami, Tokushima (JP); Youichi Taniguchi, Tokushima (JP); Tsuyoshi Yabuuchi, Tokushima (JP); Kiyoshi Fujimoto, Tokushima (JP); Yoshihiro Nishioka, Tokushima (JP); Noriyuki Kobayashi, Tokushima (JP); Tsutomu Fujimura, Tokushima (JP); Masanori Takahashi, Tokushima (JP); Kaoru Abe, Tokushima (JP); Tomonori Nakagawa, Tokushima (JP); Koichi Shinhama, Tokushima (JP); Naoto Utsumi, Tokushima (JP); Michiaki Tominaga, Tokushima (JP); Yoshihiro Ooi, Tokushima (JP); Shohei Yamada, Tokushima (JP); Kenji Tomikawa, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,595

(22) Filed: Feb. 18, 2015

(65) Prior Publication Data
US 2015/0225347 A1 Aug. 13, 2015

Related U.S. Application Data

(60) Continuation of application No. 13/749,753, filed on Jan. 25, 2013, now Pat. No. 8,993,761, which is a continuation of application No. 11/790,604, filed on Apr. 26, 2007, now Pat. No. 8,399,469, which is a division of application No. 10/333,244, filed as application No. PCT/JP02/09858 on Sep. 25, 2002, now abandoned.

(30) Foreign Application Priority Data

Sep. 25, 2001 (JP) .................. 2001-290645
Nov. 14, 2001 (JP) .................. 2001-348276
Mar. 27, 2002 (CA) ....................... 2379005

(51) Int. Cl.
C07D 215/227 (2006.01)
C07D 215/22 (2006.01)

(52) U.S. Cl.
CPC ....... *C07D 215/227* (2013.01); *C07D 215/22* (2013.01); *C07B 2200/13* (2013.01); *Y10T 428/2982* (2015.01)

(58) Field of Classification Search
CPC .................................... C07D 401/12
USPC ......................................... 544/363
See application file for complete search history.

(56) References Cited

U.S. PATENT DOCUMENTS

| 4,438,119 A | 3/1984 | Allen et al. |
| 4,687,772 A | 8/1987 | Alderice et al. |
| 4,734,416 A | 3/1988 | Banno et al. |
| 4,771,053 A | 9/1988 | Cott et al. |
| 4,983,607 A | 1/1991 | Manoury et al. |
| 5,006,528 A | 4/1991 | Oshiro et al. |
| 5,073,377 A | 12/1991 | Alexander et al. |
| 5,162,375 A | 11/1992 | Nicholson et al. |
| 5,200,410 A | 4/1993 | Traber et al. |
| 5,385,914 A | 1/1995 | Fujioka et al. |
| 5,504,093 A | 4/1996 | Gelfand et al. |
| 5,652,247 A | 7/1997 | Ogawa et al. |
| 5,691,330 A | 11/1997 | Nakao et al. |
| 5,824,680 A | 10/1998 | Turner et al. |
| 6,267,942 B1 | 7/2001 | Mori et al. |
| 6,267,989 B1 | 7/2001 | Liversidge et al. |
| 7,053,092 B2 | 5/2006 | Jordon et al. |
| 8,017,615 B2 | 9/2011 | Bando et al. |
| 8,399,469 B2 * | 3/2013 | Bando et al. ............ 514/252.13 |
| 8,580,796 B2 * | 11/2013 | Bando ................ C07D 215/227 514/253.07 |

(Continued)

FOREIGN PATENT DOCUMENTS

AU 2002226752 B2 8/2002
CA 1117110 A1 1/1982

(Continued)

OTHER PUBLICATIONS

Decision of Technical Board of Appeal regarding Opposition T2059/13 to European Patent No. EP1712225 (Application No. EP06015782.3), dated Dec. 7, 2015.

(Continued)

Primary Examiner — Alexander R Pagano
Assistant Examiner — Ebenezer O Sackey
(74) Attorney, Agent, or Firm — Finnegan, Henderson, Farabow, Garrett & Dunner, LLP

(57) ABSTRACT

The present invention provides low hygroscopic forms of aripiprazole and processes for the preparation thereof which will not convert to a hydrate or lose their original solubility even when a medicinal preparation containing the anhydrous aripiprazole crystals is stored for an extended period.

12 Claims, 31 Drawing Sheets

(56) References Cited

U.S. PATENT DOCUMENTS

| | | | |
|---|---|---|---|
| 8,642,760 | B2 | 2/2014 | Bando et al. |
| 8,759,350 | B2 | 6/2014 | Kikuchi et al. |
| 8,993,761 | B2 * | 3/2015 | Bando et al. ............... 544/363 |
| 9,017,737 | B2 | 4/2015 | Kikuchi et al. |
| 9,125,939 | B2 | 9/2015 | Kikuchi et al. |
| 9,359,302 | B2 * | 6/2016 | Bando ............... C07D 215/227 |
| 2002/0076437 | A1 | 6/2002 | Kothari et al. |
| 2002/0156067 | A1 | 10/2002 | Wong et al. |
| 2003/0027817 | A1 | 2/2003 | Tollefson |
| 2010/0069317 | A1 | 3/2010 | Forino et al. |
| 2012/0238584 | A1 | 9/2012 | Jordan et al. |
| 2012/0316180 | A1 | 12/2012 | Bando et al. |

FOREIGN PATENT DOCUMENTS

| | | |
|---|---|---|
| DE | 29 12 105 C2 | 8/1985 |
| DE | 29 12 105 C3 | 8/1985 |
| DE | 29 53 723 C2 | 1/1989 |
| EP | 0 226 441 | 6/1987 |
| EP | 0 360 077 | 3/1990 |
| EP | 0 367 141 | 5/1990 |
| EP | 0 565 274 | 10/1993 |
| EP | 0 776 927 B1 | 6/1997 |
| EP | 1145711 A1 | 10/2001 |
| EP | 1 621 198 B1 | 2/2006 |
| EP | 2 223 702 | 9/2010 |
| GB | 2017701 B | 10/1979 |
| JP | 54-130587 | 10/1979 |
| JP | 55-127371 | 10/1980 |
| JP | 56-46812 | 4/1981 |
| JP | 62-149664 | 7/1987 |
| JP | 2-191256 | 7/1990 |
| JP | A-70135 | 3/1995 |
| JP | 07-304740 | 11/1995 |
| JP | 9-40648 | 2/1997 |
| JP | 11-508280 | 10/1997 |
| JP | 9-301 867 | 11/1997 |
| JP | 9-291034 | 11/1997 |
| JP | 11-509865 | 11/1997 |
| JP | 11-335286 | 12/1999 |
| JP | 2001-302499 | 10/2001 |
| WO | WO 92/10200 | 6/1992 |
| WO | WO 92/20655 | 11/1992 |
| WO | WO 93/04681 | 3/1993 |
| WO | WO 94/09765 | 5/1994 |
| WO | WO 94/13620 | 6/1994 |
| WO | WO 98/07426 | 2/1998 |
| WO | WO 98/08817 | 3/1998 |
| WO | WO 99/38864 | 8/1999 |
| WO | WO 99/52870 | 10/1999 |
| WO | WO 2000/16777 | 3/2000 |
| WO | WO 2001/52855 | 7/2001 |
| WO | WO 02/060423 A2 | 8/2002 |
| WO | WO 02/102297 A2 | 12/2002 |
| WO | WO 03/026659 A1 | 4/2003 |
| WO | WO 03/030868 | 4/2003 |

OTHER PUBLICATIONS

Decision of the Technical Board of Appeals in Opposition of EP 1419776, dated Apr. 29, 2015.
English translation of Petitioner's Second Brief in Invalidation Action of Korean Patent No. 10-763588, filed May 29, 2016.
Letter of Opponent (Fermion) regarding Appeal T777/15 of Opposition to European Patent No. 1330249, dated Apr. 4, 2016.
Letter of Opponent in Opposition to EP 1330249, dated Apr. 4, 2016.
Letter of Opponent in Opposition to EP 1330249, dated Jun. 16, 2016.
Petition by Daewoong Pharma. Co. regarding Invalidation action of Korean Patent No. 10-0490222, dated Jan. 22, 2016.
Petitioner's Brief in Invalidation Action of Korean Patent No. 10-0490222, with English translation dated Mar. 10, 2016.
Third Party Observations regarding EP 1925308, dated Apr. 22, 2016.
Third Party Observations regarding EP 1925308, dated Jun. 23, 2016.
Communication from EPO, Office Action in Application EP16169141. 5, dated Jul. 8, 2016.
Third Party Observation in Appeal T0777/15-3.3.02, regarding EP 1330249, dated Aug. 5, 2016.
Brittain, H.G., "Polymorphism in Pharmaceutical Sciences: Chapter 6—Methods for the Characterization of Polymorphs and Solvates," (Marcel Dekker, New York 1999) pp. 235-237, 270-271.
Communication from EPO, Summons to attend oral proceedings regarding Examination of EP 08000358.5 (EP1925308), dated Sep. 25, 2015.
Glennon, "Concepts for the design of 5-HT1A serotonin agonists and antagonists," Drug Development Research, vol. 26, p. 251-274 (1992).
Office Action in U.S. Appl. No. 13/426,886 dated Nov. 3, 2015.
Tottori et al., "Pharmacology profile of OPC-14523: a novel antidepressant drug—sigma receptor agonistic, 5-HT1A receptor Agonistic, and Serotonin reuptake inhibitory activities," XXIst CINP Congress, Int'l J. of Neuropsychopharmacology, vol. 1, p. S8(Jul. 1998).
Yamada et al., "Pharmacology profile of OPC-14523(2): a novel antidepressant drug—effects of animal models of stress and obsessive-compulsive disorder," XXIst CINP Congress, Int'l J. of Neuropsychopharmacology, vol. 1, p. S9 (Jul. 1998).
"Aripiprazole OPC 14597," Drugs R & D, 2(1):47-48 (1999).
"Aripiprazole," Drugs Fut., 25(9):961-963 (2000).
Abe et al., "Effect of 5-{3-[((2,S)-1,4-Benzodioxan-2-ylmethyl)amino]propoxy}-1,3-benzodioxole HCl (MKC-242), a Novel 5-HT1A-Receptor Agonist, on Aggressive Behavior and Marble Burying Behavior in Mice," Jpn. J. Pharmacol., 76:297-304 (1998).
Abi-Dargham, "Probing cortical dopamine function in schizophrenia: what can D1 receptors tell us?" World Psychiatry, 2(3):166-171 (2003).
Abou-Gharbia et al., "Synthesis and Structure-Activity Relationship of Substituted Tetrahydro- and Hexahydro-1,2-benzisothiasol-3-one 1,1-Dioxides and Thiadiazinones: Potential Anxiolytic Agents," J. Med. Chem., 32(5):1024-1033 (1989).
Abraham et al., "LSD-Like Panic From Risperidone in Post-LSD Visual Disorder," Journal of Clinical Psychopharmacology, 16(3):238-241 (1996).
Aceto et al.., "Suppression of Opiate Withdrawal and Cocaine Hyperarousal Syndromes by Buspirone," Arzneim.-Forsch./Drug Res., 43 (II), Nr. 9, pp. 942-945 (1993).
Addington et al., "Cognitive functioning and positive and negative symptoms in schizophrenia," Schizophrenia Research 5:123-134 (1991).
Advisory Action dated Jun. 2, 2014, in U.S. Appl. No. 13/303,265.
Affidavit of Bruce Sugriv Singh sworn Jan. 19, 2012, in case No. NSD 121/2012 concerning Australian Patent Nos. 2002226752 and 2005201772 (including Exhibits BSS-3 to BSS-15).
Affidavit of Christopher John Easton affirmed May 26, 2010, in case No. NSD 1116/2009 concerning Australian Patent No. 2002334413.
Affidavit of Professor Clive Allan Prestidge affirmed Oct. 12, 2009, in case No. NSD 1116/ 2009 concerning Australian Patent No. 2002334413.
Affidavit of Professor Cools (2008), pp. 1-5.
Affidavit of Professor Patrick Dennistoun McGorry dated Feb. 21, 2012, in case No. NSD 121/2012 concerning Australian Patent Nos. 2002226752 and 2005201772 (including Exhibits PDM-5 to 7, PDM-9 to PDM-14).
Agmo et al., "Dopamine and Sexual Behavior in the Male Rabbit," Pharmacol. Biochem. Behav., 55:289-295 (1996).
Agnew et al., "Dorlands illustrated medical dictionary, 24th Edition," 1965, W:B: Saunders Company, Philadelphia, p. 1088.
Aguirre, Introduccion a la Tecnologia Farmaceutica, vol. 1, pp. 92, 96, and 117 (1989).
Ahlenius et al., "Effects of Selective Dopamine D1 and D2 Antagonists on Male Rat Sexual Behavior," Experientia, 46:1026-1028 (1990).

(56) References Cited

OTHER PUBLICATIONS

Ahlenius et al., "Specific Involvement of Central 5-HT1A Receptors in the Mediation of Male Rat Ejaculatory Behavior," Neurochemical Research, 22(8):1065-1070 (1997).
Ajit, "Does Aripiprazole Have a Role in Treating Cognitive Impairment in Parkinson's Disease," J. Neuropsychiatry Clin. Neurosci., 19(2):205-206 (2007).
Alfieri et al., "Comparative efficacy of a single oral dose of ondansetron and of busipirone against cisplatin-induced emesis in cancer patients," British Journal of Cancer, 72:1013-1015 (1995).
Amended Statement of Grounds of Opposition filed Mar. 17, 2011, for Australian Patent No. 2007201701 by Alphapharm Pty. Ltd.
American Psychiatric Association, "DSM-IV Classification for Bipolar Disorders," Quick Reference to the Diagnostic Criteria from DSM-IV, pp. 24-25 (1994).
American Psychiatric Association, "DSM-IV-TR," Diagnostic and Statistical Manual of Mental Disorders, Fourth Edition, "Mood disorders", 345-428 (2000).
American Psychiatric Association, "DSM-IV-TR," Diagnostic and Statistical Manual of Mental Disorders, Fourth Edition, "Pervasive Developmental Disorders," 69-75 (2000).
Angst et al., "Prevalence of Bipolar Disorders: Traditional and Novel Approaches," Clin. Appr. Bipol. Disord. 1:10-14 (2002).
Aoki et al., "Study on Crystal Transformation of Aripiprazol"; 4th Japanese-Korean Symposium on Separation Technology, pp. 937-940, (1996).
Aoki et al., Poster accompanying "Study on Crystal Transformation of Aripiprazol," Fourth Japanese-Korean Symposium on Separation Technology (1996).
Aouizerate et al., "Updated Overview of the Putative Role of the Serotoninergic System in Obsessive-compulsive Disorder," Neuropsychiatric Disease and Treatment, 1(3):231-243 (2005).
Appeal by Egish Died'Jserdiar Nail'Jvanoshan Mukede Resven'Jtarshashag from the decision of the Arbitrazh Court of Moscow, in re Case No. A40-115364/12-12-530, issued Dec. 4, 2012.
Apr. 10, 2008, Communication from the European Patent Office forwarding Notices of Opposition submitted by Teva Pharmaceutical Ind., Ltd. And STADA Arzneimittel AG.
Apr. 12, 2010, Communication from European Patent Office, forwarding a copy of a letter from opponent 01, Teva Pharmaceutical Industries Limited, dated Mar. 29, 2010, regarding the Appeal of EP Patent No. 1330249.
Apr. 12, 2010, Communication from European Patent Office, forwarding a copy of a letter from opponent 03, Pharmaceutical Works Polpharma, dated Mar. 22, 2010, regarding the Appeal of EP Patent No. 1330249, including Documents D15a (Experimental Results(D15) Obtained in 2006), D15b (Further data from experimental results as obtained by Opponent 03 in 2006), and D15c (Experimental results (D15c)—a Second Series of experiments).
Apter et al., "Buspirone: Future Directions," Journal of Clinical Psychopharmacology, 19(1):86-93 (1999).
Arkle et al., "Ipsapirone Suppresses Food Intake in Food-Deprived Rats by an Action at 5-HT1A Receptors," European Journal of Pharmacology, 408:273-276 (2000).
Aug. 9, 2012, Communication from European Patent Office, forwarding a copy of a letter from opponent 02, Stada Arzneirnittel AG, dated Aug. 6, 2012, regarding the appeal of EP Patent No. 1621198.
Aulton, Pharmaceutics: The Science of Dosage Form Design, Churchill Livingstone, Edinburgh, 1988, pp. 8-9 and 223-226.
Australian Government, IP Australia Examiner's first report on patent application No. 2002334413, dated Aug. 13, 2003.
Australian Government, IP Australia Examiner's report No. 2 on patent application No. 2002334413, dated Mar. 5, 2004.
Australian Government, IP Australia Examiner's report No. 3 on patent application No. 2002334413, dated Aug. 27, 2004.
Australian Government, IP Australia, Patent Examination Report No. 1 for Patent Application No. 2013203248, dated Jul. 28, 2014.
Australian Patent Office, Search Report and Written Opinion re Application No. 200302928-7, dated Sep. 30, 2004.
Australian Therapeutic Goods Administration, Australian Public Assessment Report for Aripiprazole, dated Apr. 2011.
Banov et al., "Clozapine Therapy in Refractory Affective Disorders: Polarity Predicts Response to Long-Term Follow-Up," J. Clin. Psychiatry, 55(7):295-300 (1994) (Abstract).
Baptista et al., "Long Term Administration of Some Antipsychotic Drugs Increases Body Weight and Feeding in Rats. Are D2 Dopamine Receptors Involved?" Pharmacology Biochemistry & Behavior, vol. 27, No. 3, pp. 399-405 (1987).
Bartoszyk, "Anxiolytic Effects of Dopamine Receptor Ligands: I. Involvement of Dopamine Autoreceptors," Life Sciences, 62:649-663 (1998).
Bauer et al., "Pharmazeutische Technologie," Georg Thieme Verlag, Stuttgart, pp. 75 81 (1986).
Bazire, "Psychotropic Drug Directory Feb. 2001: The professionals' pocket handbook and aide memoire," pp. 78-83 (2001).
Beers, M.D. et al., "The Merck Manual of Diagnosis and Therapy, seventeenth edition" Merck Research Laboratories, Whitehouse Stations, N.J., pp. 1513-1516, (1999).
Benabarre et al., "Bipolar disorder, schizoaffective disorder and schizophrenia: epidemiologic, clinical and prognostic differences," Eur. Psychiatry 16(3):167-172 (2001) (Abstract).
Bjorvatn et al., "Sleep/waking effects of a selective 5-HT1A receptor agonist given systemically as well as perfused in the dorsal raphe nucleus in rats," Brain Research, 770:81-88 (1997).
Boast et al., "5HT Antagonists Attenuate MK801-Impaired Radial Arm Maze Performance in Rats," Neurobiology of Learning and Memory, 71, pp. 259-271 (1999).
Bochner et al., Therapeutic Guidelines: Psychotropic (version 4), 2000, pp. 1, 2, 4, and 115-122.
Bondolifi et al., On behalf of the risperidone Study Group, "Risperidone Versus Clozapine in Treatment-Resistant Chronic Schizophrenia: A Randomized Double-Blind Study," Am. J. Psychiatry, vol. 155, pp. 499-504 (1998).
Bowden, "Novel Treatments for Bipolar Disorder," Exp. Opin. Invest. Drugs, 10(4):661-671 (2001).
Bradford et al., "Atypical antipsychotic drugs in treatment-refractory schizophrenia," Psychiatry Annals, vol. 28, pp. 618-626 (1998).
Braun et al., "Conformational Polymorphism in Aripiprazole: Preparation, Stability and Structure of Five Modifications," J. Pharmaceutical Sciences, 98(6): 2010-2026 (2009).
Breier et al., "Comparative Efficacy of Olanzapine and Haloperidol for Patients with Treatment-Resistant Schizophrenia," Biol. Psychiatry, vol. 45, pp. 403-411 (1999).
Bristol Myers Squibb & Otsuka, Package insert for Abilify® tablets, Sep. 2011.
Bristol-Myers Squibb Press Release, "New Data Presented Today at American Psychiatric Association Annual Meeting," May 22, 2002.
Brittain, "Polymorphism in Pharmaceutical Solids," Drugs and the Pharmaceutical Science, vol. 95, Chapter entitled: "Methods for the Characterization of Polymorphs X-Ray Powder Diffraction," pp. 235-238, 1999.
Brittain, "Polymorphism in Pharmaceutical Solids," New York, pp. 334-335 (1999).
Brittain, "Spectral Methods for the Characterization of Polymorphs and Solvates," Journal of Pharmaceutical Sciences, 86(4):405-412 (1997).
Brittain, Polymorphism in Pharmaceutical Solids, Marcel Dekker, Inc., New York, 1999, pp. 235-237 and 270-271.
Brown et al., "Switching Outpatients With Bipolar or Schizoaffective Disorders and Substance Abuse From Their Current Antipsychotic to Aripiprazole," J. Clin. Psychiatry, vol. 66, No. 6, pp. 756-760 (2005).
Buckley et al., "When Symptoms Persist: Clozapine Augmentation Strategies," Schizophrenia Bulletin, 27(4):615-628 (2001).
Burris et al., "Aripiprazole is a high affinity partial agonist at human D2 dopamine receptors," Int. J. Neuropsychopharmacol, 3 (Suppl 1):S129 (2000).
Caira, "Crystalline Polymorphism of Organic Compounds," pp. 165-166, (1988).

(56) References Cited

OTHER PUBLICATIONS

Canive et al., "Spontaneous Brain Magnetic Activity in Schizophrenia Patients Treated With Aripiprazole," Psychopharmacol Bull, 34(1):101-5 (1998).
Carli et al., "S 15535, a benzodioxopiperazine acting as presynaptic agonist and postsynaptic 5-HT1A receptor antagonist, prevents the impairment of spatial learning caused by intrahippocampal scopolamine," British J. Pharmacology, 128:1207-1214 (1999).
Carli et al., "Stimulation of 5-HT1A receptors in the dorsal raphe reverses the impairment of spatial learning caused by intrahippocampal scopolamine in rats," European J. Neuroscience, 10:221-230 (1998).
Certified English translation of Planowski et al. Procesy i paraty w technologii chemiczej, WNT, Warswa (1974) p. 765-771.
Cervo et al., "Effects of dopaminergic and glutamatergic receptor antagonists on the establishment and expression of conditioned locomotion to cocaine in rats," Brain Research, 739:31-38 (1996).
Chou et al., "Occupancy of 5-HT1A Receptor by Clozapine Revealed by Positron Emission Tomography in the Primate Brain," Int. J. Neuropsychopharmacol., vol. 4 (Suppl. 3), pp. S130, (2000).
Citrome & Volavka, "Atypical antipsychotics: revolutionary or incremental advance?" Expert Rev. Neurotherapeutics, 2(1):69-88 (2002).
Clifton et al., "Stimulation and Inhibition of Food Intake by the Selective Dopamine D2 Agonist, N-0437: A Meal Pattern Analysis," Pharmacol. Biochem. Behav, 33:21-26 (1989).
Cohen et al., "Characterization of the Discriminative Stimulus Produced by the Dopamine Antagonist Tiapride," J. Pharmacol. Exp. Ther., 283:566-573 (1997).
Cole et al., "5-HT1A receptor agonists improve the performance of normal and scopolamine-impaired rats in an operant delayed matching to position task," Pyschopharmacology, 116:135-142 (1994).
Communication from European Patent Office dated Jul. 8, 2010, forwarding a copy of Maiwald's statement setting forth grounds of appeal for European Application Patent No. 05023971.4 (EP 1 621 198) dated Jun. 29, 2010.
Communication to the European Patent Office, dated Oct. 24, 2014, Attachment to Submission (Auxiliary Request), regarding EP 1330249.
Communication to the European Patent Office, dated Oct. 24, 2014, Attachment to Submission (Main Request), regarding EP 1330249.
Communication to the European Patent Office, dated Oct. 24, 2014, Letter regarding the Submission of Additional Experimental Data, regarding EP 1330249.
Communication to the European Patent Office, dated Oct. 24, 2014, Submission of Additional Experimental Data, regarding EP 1330249.
Comparison of PXRD spectra; Hydrate A and MAB-1541-w—matching scales; attached to Opposition submitted by Opponent I Teva Pharmaceuticals and transmitted by European Patent Office on Apr. 27, 2009, in EP Patent No. 1 330 249.
Comparison of PXRD spectra; Hydrate A and MAB-1541-w—spectra aligned to take account of systematic error attached to Opposition submitted by Opponent I Teva Pharmaceuticals and transmitted by European Patent Office on Apr. 27, 2009, in EP Patent No. 1330 249.
Conely et al., "Evaluation of Treatment>Resistant Schizophrenia," Schizophr. Bull., vol. 23, pp. 663-674 (1997).
Conley et al., "Olanzapine compared with chlorpromazine in treatment-resistant schizophrenia," American Journal of Psychiatry, 155(7):914-920 (1998).
Conley et al., "Treatment-resistant schizophrenic patients respond to clozapine after olanzapine non-response," Biol. Psychiatry, 46:73-77 (1999).
Connor et al., "The Use of Aripiprazole in Obsessive-Compulsive Disorder: Preliminary Observations in 8 Patients," J. Clin. Psychiatry, 66(1):49-51 (2005).
Correll, "Assessing and Maximizing the Safety and Tolerability of Antipsychotics Used in the Treatment of Children and Adolescents," J. Clin. Psychiatry, 69(Supp 4):26-36 (2008).
Cottraux et al., "A Controlled Study of Cognitive Behavior Therapy with Buspirone or Placebo in Panic Disorder with Agoraphobia," British Journal of Psychiatry 167:635-641 (1995).
Court Judgment, Federal Court of Australia, *Bristol-Myers Squibb Co. v. Apotex Pty. Ltd.*, regarding Australian Patent No. 2002334413, dated Jan. 23, 2015.
Craig & Young, "1-Benzylpiperazine," Organic Syntheses, 42:19 (1962).
Cuesta et al., "Effects of Olanzapine and Other Antipsychotics on Cognitive Function in Chronic Schizophrenia: A longitudinal Study," Schizophrenia Research, 48:17-28 (2001).
Daniel et al., "Aripiprazole. a novel antipsychotic: Overview of a phase II study result," Int. J. Neuropsychopharmacol, 3 (Suppl 1):S157 (2000).
Davis et al., "Ziprasidone," CNS Drugs 8(2):153-159 (1997).
De Vry et al.,"Discriminative stimulus properties of the 5-HT receptor agonist 1A BAY x 3702 in the rat," Euro J. of Pharmacology, vol. 357, pp. 1-8 (1998).
Decision of the Arbitrazh Court of the City of Moscow in Case No. A40-115364/12-12-530 dated Dec. 4, 2012.
Declaration of Markus Antonietti executed Jan. 29, 2013, during opposition proceedings for European Patent No. 1330249, including Exhibits A and B.
Declaration of Nikkiso Co., Ltd. by Yasuo Kizawa dated Feb. 7, 2013, during opposition proceedings for European Patent No. 1330249, including "Pamphlet of Microtrac HRA" and "Pamphlet of Nanotrac UPA".
Drevets et al., "PET Imaging of Serotonin 1A Receptor Binding in Depression," Biol. Psychiatry, vol. 46: pp. 1375-1387 (1999).
Dziegilewski, "Selected Mood Disorders," DSM-IV TR in Action, 2nd Edition, pp. 297-298 (2010).
Ebenezer et al., "Effects of the 5-HT1A Receptor Agonist 8-OH-DPAT on Operant Food Intake in Food-Deprived Pigs," Physiology & Behavior, 67(2):213-217 (1999).
Ebsworth, et al., "Diffraction by powders," Structural Methods in Inorganic Chemistry, Blackwell Scientific Publications, 2nd ed., p. 360 (1991).
Ecuadorian Institute of Intellectual Property Patentability Examination Report for Application No. SP06 6521, dated Sep. 5, 2008.
Ecuadorian Institute of Intellectual Property Patentability Examination Report for Application No. SP06 6522, dated Sep. 19, 2008.
Ecuadorian Institute of Intellectual Property, Patentability Examination Report for Application No. SP034434 PCT, dated Jun. 8, 2004.
Elvevag et al., "Cognitive Impairment in Schizophrenia Is the Core of the Disorder," Critical Reviews in Neurobiology, 14(1):1-21 (2000).
English abstract of JP 54-130587 published Oct. 9, 1979.
English abstract of JP 56-46812 published Apr. 28, 1981.
English translation of a letter from opponent 02, Stada Arzneirnittel AG, dated Aug. 6, 2012, regarding the appeal of EP Patent No. 1621198.
English translation of Aripiprazol Experimental Report by Dr. Schmidt, Dec. 23, 2006.
English translation of Aripiprazol Experimental Report by Dr. Striegel, Dec. 21, 2006.
English translation of communication from European Patent Office dated Jul. 8, 2010, forwarding a copy of Maiwald's statement setting forth grounds of appeal for European Application Patent No. 05023971.4 (EP 1 621 198) dated Jun. 29, 2010.
English translation of Decision of the Arbitrazh Court of the City of Moscow in Case No. A40-115364/12-12-530 dated Dec. 4, 2012.
English translation of Ecuadorian Institute of Intellectual Property, Patentability Examination Report for Application No. SP034434 PCT, dated Jun. 8, 2004.
English translation of European Patent Office Submission of Ratiopharm GMBH in Opposition to European Patent No. 1330249, transmitted Jul. 2, 2010.
English translation of European Patent Office Submission of Ratiopharm GMBH in Opposition to European Patent No. 1330249, transmitted Jul. 21, 2010, submitting Projektbericht Aripiprazol by Roland Boese and Carsten Schauerte (Document D37 referenced in the

(56) References Cited

OTHER PUBLICATIONS

European Patent Office Submission of Ratiopharm GMBH in Opposition to European Patent No. 1330249, transmitted Jul. 2, 2010).
English translation of European Patent Office, Communication of a notice of opposition for EP Application No. 06015782.3/ EP Patent No. 1712225, dated Jan. 26, 2012, forwarding a copy of Helm AG's Jan. 6, 2012, submission.
English translation of Examination Report Aripiprazole by Roland Boese, dated May 31, 2010, (Document D36 referenced in the European Patent Office Submission of Ratiopharm GMBH in Opposition to European Patent No. 1330249, transmitted Jul. 2, 2010).
English translation of Examination Report in Argentine Patent Application No. P100104973, dated Nov. 6, 2014.
English translation of Examination Report in Argentine Patent Application No. P110101189, dated Dec. 11, 2014.
English translation of excerpt from Examination Guidelines for Patent and Utility Model in Japan, Part VII: Examination Guidelines for Inventions in Specific Fields, Ch. 3 Medicinal Inventions, p. 5, attached to the Notice of Information Disclosure byThird Party issued by the Japanese Patent Office in Japanese Patent Application No. 2007-179275 dated May 31, 2010.
English translation of Hirose, "New Schizophrenia Drug Aripiprazole (OPC-14597)," Brain Science (Nou no Kagaku), vol. 20, pp. 1135-1140 (1998).
English Translation of Japanese Decision of Rejection dated Aug. 22, 2014, JP 2011-133032 DA-05122.
English translation of Krowczynski et al., "Technologia Postaci Lekow," National Institute of Medical Publications, Warsaw, 1969, pp. 54-63, 78-81, 368-379.
English translation of Laboratory Report by Ratiopharm, dated Sep. 22, 2008 (Document D38 referenced in the European Patent Office Submission of Ratiopharm GMBH in Opposition to European Patent No. 1330249, dated Jul. 2, 2010).
English translation of List of Queries to Panel of Experts by Otsuka Pharmaceutical Co., Ltd., dated Oct. 21, 2013, to the Office of the Honorable Judge of Istanbul 3rd Civil Court for Intellectual and Industrial Property Rights in File No. 2012/200E.
English translation of Notice of Information Disclosure by Third Party issued by the Japanese Patent Office in Japanese Patent Application No. 2007-179275 dated May 31, 2010.
English translation of Novelty Search Report from Hungarian Application No. P0600141, dated Feb. 19, 2008.
English translation of Office Action in Japanese Patent Application No. 2011-133032 dated Feb. 28, 2014.
English translation of Office Action in Japanese Patent Application No. 2011-133033 dated Aug. 19, 2014.
English translation of Office Action in Japanese Patent Application No. 2011-133033 dated Feb. 28, 2014.
English translation of Office Action in Taiwanese Patent Application No. 098116881 dated May 17, 2010.
English translation of petition of Sanovel Ilac Sanayi Ve Ticaret A.S. regarding Turkish patent TR 2006 02467 T4, submitted to the Istanbul 3rd Civil Court of Intellectual and Industrial Property Rights on Jun. 6, 2013.
English translation of Request for declaratory judgment on lack of infringement by Generica Ilac Sanayi Ve Tic A.S. dated Mar. 27, 2013, before the Istanbul Court on Duty for Intellectual and Industrial Rights.
English translation of Russian Patent Office Submission of Egis Gyógyszergyár Nyrt in Opposition to Russian Patent No. 2259366 (Application No. 2003101334), including Enclosure 1, transmitted Oct. 5, 2011.
English translation of Submission of questions to experts of Sanovel Ilac Sanayi Ve Ticaret A.S. dated Oct. 21, 2013, to the Office of the Honorable Judge of Istanbul 3rd Civil Court for Intellectual and Industrial Property Rights in File No. 2012/200E.
English translation of Submission of Sanovel Ilac Sanayi Ve Ticaret A.S. dated Dec. 29, 2014, to the Office of the Honorable Judge of Istanbul 3rd Civil Court for Intellectual and Industrial Property Rights in File No. 2012/200E, regarding Patent No. TR 2006/02467 T4.
English translation of Submission of Sanovel Ilac Sanayi Ve Ticaret A.S. dated Nov. 21, 2013, to the Office of the Honorable Judge of Istanbul 3rd Civil Court for Intellectual and Industrial Property Rights in File No. 2012/200E.
English translation of Technical Examination Report in Brazilian Patent Application No. PI 0206237-2, received on Dec. 22, 2014.
English translation of Technical Opinion 1907 from the Colombian Superintendence of Industry and Trade, dated Jul. 3, 2009.
English translation of Technical Opinion 2309 from the Colombian Superintendence of Industry and Trade, dated Dec. 28, 2007.
English translation of the Office Action from Japanese Patent Office issued in Japanese Patent Application No. 2007-179275 dated Apr. 13, 2011.
English translation of the Office Action from Japanese Patent Office issued in Japanese Patent Application No. 2007-179275 dated Oct. 22, 2010.
European Medicines Agency report on aripiprazole, 2005.
European Patent Office Communication of a notice of opposition for EP Application No. 04002427.5-2101/ EP Patent No. 1419776, dated Jan. 19, 2011, forwarding a copy of Teva Pharmaceutical Industries Ltd.'s Jan. 13, 2011, submission including Experimental Report 1 and Annexes 1-3.
European Patent Office Decision of the Technical Board of Appeals regarding Appeal T0801/10 of Opposition to European Patent No. 1621198, dated Sep 1, 2014.
European Patent Office Decision revoking European Patent No. EP-B-1330249 and Provision of a copy of the minutes of the oral proceedings, Jul. 7, 2009.
European Patent Office Decision revoking European Patent No. EP-B-1419776 and Provision of a copy of the minutes of the oral proceedings, Jun. 5, 2012.
European Patent Office Official Minutes of Oral Proceeding regarding Appeal T0801/10 of Opposition to European Patent No. 1621198, dated Jul. 8, 2014.
European Patent Office Submission of Egis Gyógyszergyár Nyrt in Opposition to European Patent No. 1330249B1, transmitted Apr. 27, 2009.
European Patent Office submission of Otsuka Pharmaceutical Co., Ltd. during appeal for European Patent No. 1419776, dated Oct. 15, 2012, including enclosures D23, D24, and D25.
European Patent Office submission of Otsuka Pharmaceutical Co., Ltd. during appeal T 801/10-3.3.01 for EP1621198 dated Jan. 16, 2014.
European Patent Office submission of Otsuka Pharmaceutical Co., Ltd. during opposition proceedings for European Patent No. 1712225, dated Nov. 5, 2012, including enclosure Table listing all cited documents, D41, D42, and D51.
European Patent Office submission of Otsuka Pharmaceutical Co., Ltd. during opposition proceedings for European Patent No. 1330249, dated Mar. 6, 2009, including x-ray and DSC spectra for Samples 1 and 2 and p. 939 of D2.
European Patent Office submission of Otsuka Pharmaceutical Co., Ltd. during opposition proceedings for European Patent No. 1330249, dated Mar. 7, 2013.
European Patent Office submission of Otsuka Pharmaceutical Co., Ltd. during opposition proceedings for European Patent No. 1330249, dated Oct. 25, 2012, including enclosures D39 and D40.
European Patent Office submission of Otsuka Pharmaceutical Co., Ltd. during opposition proceedings for European Patent No. 1419776, dated Apr. 3, 2012, including Declarations 1 and 2 of Mr. Aoki, executed Apr. 2, 2012.
European Patent Office submission of Otsuka Pharmaceutical Co., Ltd. during opposition proceedings for European Patent No. 1419776, dated Aug. 29, 2011, including DSC and XRD data for Type-2 Crystal.
European Patent Office submission of Otsuka Pharmaceutical Co., Ltd. during opposition proceedings for European Patent No. 1419776, dated Feb. 24, 2012, including Annex 1, overview of the powder X-ray diffraction spectra of Type-1, Type-2 and Type-C(Part 1-Part

(56) References Cited

OTHER PUBLICATIONS 4) and Annex 2, overview of the powder X-ray diffraction spectra of Type-2 crystals, Sample MT-2178 (Part 1) and PZ-8057-3 (Part 2) and Type-C crystals.
European Patent Office submission of Otsuka Pharmaceutical Co., Ltd. during the appeal of European Patent No. 1330249, dated Nov. 17, 2009, including Experimental Report with Annexes 1-3.
European Patent Office submission of Otsuka Pharmaceutical Co., Ltd. in European Patent Application No. 02782507.4-2101, dated Dec. 15, 2004.
European Patent Office submission of Otsuka Pharmaceutical Co., Ltd. in European Patent Application No. 04002427.5, dated Sep. 8, 2008, including Annexes 1-3.
European Patent Office submission of Otsuka Pharmaceutical Co., Ltd. in European Patent Application No. 06015782.3, dated Aug. 19, 2010.
European Patent Office submission of Otsuka Pharmaceutical Co., Ltd. in European Patent Application No. 06015782.3, dated Nov. 13, 2008, including Comparative Experiments.
European Patent Office submission of Otsuka Pharmaceutical Co., Ltd. in European Patent Application No. 08000357.7-2101, dated Mar. 5, 2009, including Annexes 1-3.
European Patent Office submission of Otsuka Pharmaceutical Co., Ltd. in European Patent Application No. 08000358.5, dated Apr. 27, 2009, including Annexes 1-3.
European Patent Office submission of Otsuka Pharmaceutical Co., Ltd. in European Patent Application No. 08000359.3-2101, dated Mar. 5, 2009, including Annexes 1-3.
European Patent Office submission of Otsuka Pharmaceutical Co., Ltd. in European Patent Application No. 08000360.1-2101, dated Mar. 5, 2009, including Annexes 1-3.
European Patent Office submission of Otsuka Pharmaceutical Co., Ltd. in the appeal of European Patent No. 1621198, dated May 27, 2011, including Affidavit of Bryan L. Roth, M.D., Ph.D., executed May 23, 2011.
European Patent Office submission of Otsuka Pharmaceutical Co., Ltd. regarding Appeal T0801/10 of Opposition to European Patent No. 1621198, dated Jun. 6, 2014.
European Patent Office submission of Otsuka Pharmaceutical Co., Ltd., regarding appeal T 2059/13-3.3.02 for EP1712225 dated Nov. 26, 2013.
European Patent Office Submission of Pentafarma S.A. in Opposition to European Patent No. 1712225, dated Apr. 11, 2013, including D55 (excerpt from online Dictionary).
European Patent Office Submission of Ratiopharm GMBH in Opposition to European Patent No. 1330249, dated Jul. 2, 2010.
European Patent Office Submission of Ratiopharm GMBH in Opposition to European Patent No. 1330249, dated Jul. 21, 2010, submitting Projektbericht Aripiprazol by Roland Boese and Carsten Schauerte (Document D37 referenced in the European Patent Office Submission of Ratiopharm GMBH in Opposition to European Patent No. 1330249, dated Jul. 2, 2010).
European Patent Office Submission of Teva Pharmaceutical Ind., Ltd., submitting facts and arguments in the appeal of European Patent Application No. 05023971.4 (EP 1 621 198), dated Jun. 29, 2010.
European Patent Office Submission of Teva Pharmaceutical Industries Limited in Opposition to European Patent No. 1330249, dated Apr. 18, 2008.
European Patent Office Submission of Teva Pharmaceutical Industries Ltd. in opposition to European Patent No. 1419776, dated Apr. 16, 2012.
European Patent Office Submission of Teva Pharmaceutical Industries Ltd. in Opposition to European Patent No. 1712225, dated Apr. 12, 2013.
European Patent Office Summons to Oral Proceedings regarding Appeal T0801/10 of Opposition to European Patent No. 1621198, dated Feb. 24, 2014.

European Patent Office, communication dated Dec. 13, 2005, of observations of a third party regarding EP Application No. 02782507. 4/EP Patent No. 1330249, forwarding letter dated Nov. 30, 2005.
European Patent Office, communication dated Jan. 27, 2006, of observations of a third party regarding EP Application No. 02782507. 4/EP Patent No. 1330249, forwarding letter dated Jan. 17, 2006 and documents D1 to D7.
European Patent Office, communication dated Jan. 28, 2014, forwarding letter of opponent Sanovel Ilac Sanayi Ve Ticaret A.S. dated Jan. 21, 2014, including exhibits WuW1 and WuW2.
European Patent Office, communication dated Jan. 28, 2014, forwarding letter of opponent Sanovel Ilac Sanayi Ve Ticaret A.S. dated Jan. 21, 2014, regarding EP1712225, including annexes WuW1 and WuW2.
European Patent Office, communication dated Jul. 16, 2013, regarding minutes of oral proceedings held Jul. 5, 2013, in Appeal No. T1772/09-3.3.01 regarding EP 1330249.
European Patent Office, communication dated Jun. 7, 2013, regarding opposition to EP Application No. 02782507.4/EP Patent No. 1330249, forwarding submission of Egis Gyógyszergyár Nyrt dated Jun. 4, 2013, including documents D43 (printout of http://showadenko. us/product/thermal.php "Thermal Functional Filler Alumina / hBN"), and D45b (printout of http://www.osrok.com/products/catalog/psa/ LA-910.pdf "Horiba LA-910, Laster Scattering Particle Size Distribution Analyzer").
European Patent Office, communication dated Mar. 10, 2014, forwarding letter of opponent Chemo Iberica, S.A. dated Mar. 5, 2014, regarding EP1712225.
European Patent Office, communication dated Mar. 20, 2014, forwarding a copy of Decision of the Technical Board of Appeal dated Jul. 5, 2013, regarding EP1330249.
European Patent Office, communication dated Mar. 27, 2014, forwarding letter of opponent Actavis Group PTC dated Mar. 20, 2014, regarding EP1712225, including document MAI8, Mutschler et al., "Mutschler Arzneimittelwirkungen: Lehrbuch der Pharmakologieund Toxikologie," 8th edition, pp. 157-172 (2001).
European Patent Office, communication dated May 10, 2013, forwarding letter of opponent Teva Pharmaceutical Industries Ltd dated May 6, 2013, in Appeal No. T1555/12-3.3.02 regarding EP1419776.
European Patent Office, communication dated May 25, 2005, of observations of a third party regarding EP Application No. 02782507. 4/EP Patent No. 1330249, forwarding letter of Maprimed S.A. dated May 17, 2005.
European Patent Office, Communication of a notice of opposition for EP Application No. 06015782.3/ EP Patent No. 1712225, dated Jan. 26, 2012, forwarding a copy of Actavis Group PTC EHF's Jan. 5, 2012, submission.
European Patent Office, Communication of a notice of opposition for EP Application No. 06015782.3/ EP Patent No. 1712225, dated Jan. 26, 2012, forwarding a copy of Chemo Iberica, S.A.'s Jan. 6, 2012, submission.
European Patent Office, Communication of a notice of opposition for EP Application No. 06015782.3/ EP Patent No. 1712225, dated Jan. 26, 2012, forwarding a copy of Helm AG's Jan. 6, 2012, submission.
European Patent Office, Communication of a notice of opposition for EP Application No. 06015782.3/ EP Patent No. 1712225, dated Jan. 26, 2012, forwarding a copy of Hexal AG's Jan. 4, 2012, submission.
European Patent Office, Communication of a notice of opposition for EP Application No. 06015782.3/ EP Patent No. 1712225, dated Jan. 26, 2012, forwarding a copy of Pentafarma S.A.'s Jan. 5, 2012, submission.
European Patent Office, Communication of a notice of opposition for EP Application No. 06015782.3/ EP Patent No. 1712225, dated Jan. 26, 2012, forwarding a copy of Sanovel Ilac Sanayi Ve Ticaret A.S.'s Jan. 3, 2012, submission.
European Patent Office, Communication of a notice of opposition for EP Application No. 06015782.3/ EP Patent No. 1712225, dated Jan. 26, 2012, forwarding a copy of Stada Arzneimittel AG's Jan. 3, 2012, submission.

(56) References Cited

OTHER PUBLICATIONS

European Patent Office, Communication of a notice of opposition for EP Application No. 06015782.3/ EP Patent No. 1712225, dated Jan. 26, 2012, forwarding a copy of Teva Pharmaceutical Industries Ltd.'s Jan. 5, 2012, submission.
European Patent Office, Interlocutory Decision in Opposition Proceedings regarding European Patent No. 1330249, dated Feb. 20, 2015.
European Patent Office, International Search Report for Application No. PCT/JP02/09858, dated Nov. 14, 2002.
European Patent Office, Minutes of Oral Proceedings regarding Opposition to European Patent No. 1330249, dated Feb. 20, 2015.
European Patent Office, Summons to attend oral proceedings pursuant to Rule 115(1) EPC, EP Patent No. 1330249, Jan. 27, 2009.
European Patent Office, Summons to attend oral proceedings pursuant to Rule 115(1) EPC, EP Patent No. 1419776, Oct. 25, 2011.
European Patent Office, Summons to attend oral proceedings pursuant to Rule 115(1) EPC, EP Patent No. 1621198, Oct. 13, 2009.
European Patent Office, Summons to attend oral proceedings pursuant to Rule 115(1) EPC, EP Patent No. 1712225, Feb. 1, 2013.
European Patent Office, Summons to Oral Proceedings regarding Opposition to European Patent No. 1330249, dated Jul. 14, 2014.
European Pharmacopoeia 5.0 and 8.0, dated 2005 and 2008.
Examination Report Aripiprazole by Roland Boese, dated May 31, 2010 (Document D36 referenced in the European Patent Office Submission of Ratiopharm GMBH in Opposition to European Patent No. 1330249, dated Jul. 2, 2010).
Examiner's Re-examination Report dated Jan. 28, 2009, for Australian Patent No. 2002226752.
Examiner's Re-examination Report dated Jan. 28, 2009, for Australian Patent No. 2002334413.
Examiner's Re-examination Report dated Jan. 28, 2009, for Australian Patent No. 2005201772.
Examiner's Re-examination Report dated Oct. 10, 2006, for Australian Patent No. 2002334413.
Excerpt from Examination Guidelines for Patent and Utility Model in Japan, Part VII: Examination Guidelines for Inventions in Specific Fields, Ch. 3 Medicinal Inventions, p. 5, attached to the Notice of Information Disclosure by Third Party issued bythe Japanese Patent Office in Japanese Patent Application No. 2007-179275 dated May 31, 2010.
Experimental Report (Aripiprazole Hydrate A), D4 from EPO Decision of Jul. 7, 2009, regarding Application No. 02782507.4-2101/1330249.
Experimental Results (D3) provided by Opposition—Pharmaceutical Works Polpharma, transmitted Jan. 16, 2007, by European Patent Office, Application No. 02782507.4-2101/1330249.
Expert Report of Sanovel Ilac Sanayi Ve Ticaret A.S. dated Oct. 30, 2014, to the Office of the Honorable Judge of Istanbul 3rd Civil Court for Intellectual and Industrial Property Rights in File No. 2012/200, regarding Patent No. TR 2006/02467 T4.
Farah, "Atypicality of Atypical Antipsychotics", Prim. Care Companion, J. Clin. Psychiatry, 7:268-274, 2005.
Feb. 12, 2004, Communication from European Patent Office, forwarding a copy of third party observations regarding EP Patent Application No. 02782507.4, dated Jan. 30, 2004.
Federal Court of Australia, Judgment of J. Yates, dated Mar. 16, 2012, in case No. NSD 121/2012 concerning Australian Patent Nos. 2002226752 and 2005201772.
Federal Court of Australia, Transcript of Proceedings in case No. NSD 121/2012, dated Feb. 3, 2012, concerning Australian Patent Nos. 2002226752 and 2005201772.
Fedoroff, "Buspirone Hydrochloride in the Treatment of an Atypical Paraphilia," Archives of Sexual Behavior, 21(4):401-406 (1992).
Ferrari et al., "The Selective D2 Dopamine Receptor Antagonist Eticlopride Counteracts the Ejaculatio Praecox Induced by the Selective D2 Dopamine Agonist SND 919 in the Rat," Life Sciences, 55(14):1155-1162 (1994).
Findling et al., "An open clinical trial of risperidone monotherapy in young children with autistic disorder," Psychopharmacol. Bull., 33(1):155-159 (1997) (Abstract).
Findling et al., "Aripiprazole in Children with Attention-Deficit/Hyperactivity Disorder," J. Child and Adolescent Psychopharma., 18(4):347-354 (2008).
Fleischhacker et al., "A double-blind, randomized comparative study of aripiprazole and olanzapine in patients with schizophrenia," Biol. Psychiatry, 65:510517 (2009).
Forbes et al., "(R)-3, N-Dimethyl-N-[1-Methyl-3-(4-Methyl-Piperidin-1-yl)Propyl]Benzenesulfonamide: The First Selective 5-HT7 Receptor Antagonist"; Journal of Medical Chemistry, 41(5):655-657 (1998).
Ford et al., "Pharmaceutical Thermal Analysis: Techniques and Applications," pp. 210-212 (1989).
Foreman et al., "Preclinical Studies on LY228729: A Potent and Selective Serotonin1A Agonist," Journal of Pharmacology and Experimental Therapeutics, 267(1):58-71 (1993).
Fratta et al., "Stress-induced insomnia: opioid-dopamine interactions," European Journal of Pharmacology, 142:437-440 (1987).
Friedman et al., "Open-Label Flexible-Dose Pilot Study to Evaluate the Safety and Tolerability of Aripiprazole in Patients with Psychosis Associated with Parkinson's Disease," Movement Disorders, 21(12):2078-2081 (2006).
Frye et al., "Clozapine in bipolar disorder: treatment implications for other atypical antipsychotics," Journal of Affective Disorders, 48:91-104 (1998).
Fujii et al., "Sexual Dysfunction in Japanese Patients with Schizophrenia Treated with Antipsychotics," Prog. Neuropsychopharmacol. Biol. Psychiatry, Nov. 28, 2009, issue 1878-4216.
Fujii et al.,"Effects of Clozapine on Cognitive Functioning in Treatment-Resistant Schizophrenic Patients," J. Neuropsychiatry Clin. Neurosci, vol. 9, pp. 240-245 (1997).
Furniss et al., Vogel's Textbook of Practical Organic Chemistry, 5th Ed., pp. 149-151, 1989.
Further Amended Particulars of Invalidity for Australian Patent No. 2002334413, dated Jun. 15, 2011, by Apotex Pty. Ltd.
Galeotti et al., "Role of 5-HT1A Receptors in Mouse Passive Avoidance Paradigm," Jpn. J. Pharmacol., 84:418-424 (2000).
Garattini et al., "Progress in Assessing the Role of Serotonin in the Control of Food Intake," Clin. Neuropharmacol., 11(suppl. 1); S8-S32, (1988).
Garcia-Anaya et al., Los Antipsycoticos atipicos: Una Revision, Salud Mental, 24(5):37-43 (2001).
Gelernter et al., "D2 Dopamine Receptor Gene (DRD2) Allele and Haplotype Frequencies in Alcohol Dependent and Control Subjects: No Association with Phenotype or Severity of Phenotype," Neuropsychopharmacology, 20:640-649 (1999).
Gelernter et al., "No Association Between D2 Dopamine Receptor (DRD2) Alleles or Haplotypes and Cocaine Dependence or Severity of Cocaine Dependence in European-and African-Americans," Biol. Psychiatry, 45:340-345 (1999).
Gentile, "A Systematic Review of Quality of Life and Weight Gain-related Issues in Patients Treated for Severe and Persistent Mental Disorders: Focus on Aripiprazole," Neuropsychiatric Disease and Treatment, 5:117-125 (2009).
Geretsegger et al., "Ipsapirone in the Treatment of Bulimia Nervosa: An Open Pilot Study," International Journal of Eating Disorders, 17(4):359-363 (1995).
Giannini et al., "Behavioral Response to Buspirone in Cocaine and Phencyclidine Withdrawal," Journal of Substance Abuse Treatment, 10:523-527 (1993).
Giron, "Investigations of Polymorphism and Pseudo-Polymorphism in Pharmaceuticals by Combined Thermoanalytical Techniques," J. Thermal Analysts and Calorimetry, 64: 37-60 (2001).
Glick et al., "Treatment with atypical antipsychotics: new indications and new populations," Journal of Psychiatric Research, 35:187-191 (2001).
Goldberg & Gold, "Neurocognitive Deficits in Schizophrenia," in Schizophrenia (Hirsch & Weinberger eds., Blackwell Science Ltd.), 1995, pp. 146-162.
Goldman-Rakic et al., "D1 Receptors in Prefrontal Cells and Circuits," Brain Research Reviews, 31:295-301 (2000).

(56) References Cited

OTHER PUBLICATIONS

Goodnick et al., "Aripiprazole: Profile on efficacy and safety," Expert Opinion on Pharmacotherapy, 3(12):1173-1781 (2002).
Goodwin, F.K. and Jamison, K.R., Manic-Depressive Illness, Oxford University Press, pp. 420-422 (1990).
Government of India, Patent Office, Communication regarding Patent Application No. 722/KOLNP/2003, dated Aug. 29, 2014.
Green et al., "Does Risperidone Improve Verbal Working Memory in Treatment-Resistant Schizophrenia?" Am. J. Psychiatry, vol. 154, pp. 799-804 (1997).
Guille et al., "A Naturalistic Comparison of Clozapine, Risperidone, and Olanzapine in the Treatment of Bipolar Disorder," J. Clin. Psychiatry, 61(9):638-642 (2000).
Haddjeri et al., "Acute and long-term actions of the antidepressant drug mirtazapine on central 5-HT neurotransmission," Journal of Affective Disorders 51:255-266 (1998).
Haddjeri et al., "Increased Tonic Activiation of Rat Forebrain 5-HT1A Receptors by Lithium Addition to Antidepressant Treatments," Neuropsychopharmacology 22(4):346-356 (2000).
Haddjeri et al., "Long-Term Antidepressant Treatments Result in a Tonic Activiation of Forebrain 5-HT1A Receptors," Journal of Neuroscience 18(23):10150-10156 (1998).
Haensel et al., "Flesinoxan: a prosexual drug for male rats," European Journal of Pharmacology, 330:1-9 (1997).
Hagger et al., "Improvement in Cognitive Functions and Psychiatric Symptoms in Treatment-Refractory Schizophrenic Patients Receiving Clozapine," Biol. Psychiatry, vol. 34, pp. 702-712 (1993).
Hammerstad et al., "Buspirone in Parkinson's Disease," Clin. Neuropharmacol., 9(6):556-60 (1986).
Hamon et al., "Alterations of Central Serotonin and Dopamine Turnover in Rats Treated with Ipsapirone and Other 5-Hydroxytryptamine1A Agonists with Potential Anxiolytic Properties," J. Pharmacol. Exp. Ther., 246(2):745-752 (1988).
Harada et al., "Aripiprazole Augmentation for a Patient With Partial Remission of Panic Disorder," J. Clin. Psychopharmacology, Letters to the Editor, 29(3):301-302 (2009).
Harwood et al., "Experimental Organic Chemistry Principles and Practice," Blackwell Scientific Publications), pp. 136-137, (1989).
Hashimoto et al., "Differential changes in serotonin 5-HT1A and 5-HT2 receptor binding in patients with chronic schizophrenia," Psycho-pharmacology, vol. 112, pp. S35-S39 (1993).
Heinrichs et al., "The Quality of Life Scale: An Instrument for Rating the Schizophrenic Deficit Syndrome," Schizophrenia Bulletin, 10(3):388-398 (1984).
Heinz et al., Organikum, Organish-chemisches Grundpractikum, VEB Deutscher Verlag der Wissenschaften, Berlin, tables A.32 and A.35 and sections 1.10.2-1.10.4, 1986.
Hellewell, "Treatment-resistant schizophrenia: Reviewing the options and identifying the way forward," J. Clin. Psychiatry, 60(Suppl 23):14-19 (1999).
Helman, Farmacotecnia Teorica y Practica. Tomo IV. Editorial Continental, S.A., 1981, pp. 1142 and 1165.
Hilty et al., "A Review of Bipolar Disorder Among Adults," Psychiatric Services, vol. 50(2): pp. 201-213 (1999).
Hirose et al., "Efficacy and favorable side effect profile of aripiprazole determined in rats with apomorphine-induced stereotypy, catalepsy, and ptosis induction," Int. J. Neuropsychopharmacol, 3 (Suppl 1):S131 (2000).
Hirose, "New Schizophrenia Drug Aripiprazole (OPC-14597)," Brain Science (Nou no Kagaku), vol. 20, pp. 1135-1140 (1998).
Hoge et al., "Aripiprazole as Augmentation Treatment of Refractory Generalized Anxiety Disorder and Panic Disorder," CNS Spectr. 13(6):522-527 (2008).
Hoshino et al., "Blood Serotonin and Free Tryptophan Concentration in Autistic Children," Neuropsychobiology 11:22-27 (1984).
Hustig & Norrie, "Managing schizophrenia in the community," MJA Practice Essentials—Mental Health, 57-62 (1998).
Inoue et al., "Aripiprazole, a novel antipsychotic drug, inhibits quinpirole-evoked GTPase activity but does not up-regulate dopamine D2 receptor following repeated treatment in the rat striatum," European Journal of Pharmacology 321:105-111 (1997).
Inoue et al., "Differential Effects on D2 Dopamine Receptor and Prolactin Gene Expression by Haloperidol and Aripiprazole in the Rat Pituitary," Molecular Brain Research, 55: 285-292 (1998).
Inoue et al., "Effects of the Novel Antipsychotic Agent 7-{4-[4-(2,3-dichlorophenyl)-1-piperazinyl]butyloxy}-3,4-dihydro-2(1H)-quinolinone (OPC-14597) on Prolactin Release from the Rat Anterior Pituitary Gland," J. Pharm. Exp. Ther., 277:137-143 (1996).
Intellectual Property Office of Singapore, Search Report and Written Opinion for Singaporean Application No. 200302928-7, dated Dec. 13, 2004.
International Standard, "Particle size analysis-Laser diffraction methods," ISO 13320-1:1999(E) (1999).
International statistical classification of diseases and related health disorders, 10th revision (ICD-10), vol. 1—Systematic directory, p. 281, 2010.
Jann, "Clozapine," Pharmacoptherapy, vol. 11, pp. 179-195 (1991).
Jan. 10, 2007, Communication from the European Patent Office forwarding a Notice of Opposition submitted by Teva Pharmaceutical Industries Limited.
Jan. 11, 2007, Communication from the European Patent Office forwarding a Notice of Opposition submitted by Fermion Oy.
Jan. 15, 2007, Communication from the European Patent Office forwarding a Notice of Opposition submitted by EGIS Gyógyszergyár Nyrt.
Jan. 15, 2007, Communication from the European Patent Office forwarding a Notice of Opposition submitted by ratiopharm GmbH.
Jan. 16, 2007, Communication from the European Patent Office forwarding a Notice of Opposition submitted by Pharmaceutical Works Polypharma.
Jan. 31, 2013, Communication from the European Patent Office, forwarding a letter of opponent Ovi, Pentafarma S.A., dated Jan. 21, 2013, regarding opposition proceedings for European Patent No. 1712225.
Japanese Decision of Rejection dated Aug. 22, 2014, JP 2011-133032 DA-05122.
Jordan et al., "In Vivo Effects of Aripiprazole on Cortical and Striatal Dopaminergic and Serotonergic Function," European Journal of Pharmacology, 483: 45-53 (2004).
Jordan et al., "In Vivo Effects of Aripiprazole on Dopaminergic and Serotonergic Function in Rat Prefrontal Cortex and Striatum," Society for Neuroscience Abstracts, Society of Neuroscience, US, 2(27):2327, AN87503 (2001).
Jordan et al., "The antipsychotic aripiprazole is a potent, partial agonist at the human 5-HT1A receptor," European Neuropsychopharmacol., 11(suppl. 3):S268 (2001).
Kane et al., "Aripiprazole for Treatment-Resistant Schizophrenia: Results of a Multicenter, Randomized, Double-Blind, Comparison Study Versus Perphenazine," J. Clin. Psychiatry, 68(2):213-223 (2007).
Kane et al., "Clozapine for the treatment-resistant schizophrenic," Arch. Gen. Psychiatry, 45:789-796 (1988).
Kane et al., "Efficacy of Aripiprazole in Psychotic Disorders: Comparison With Haloperidol and Placebo," Int J Neuropsychopharmacol, 3 (Suppl 1):Abst P01.124 (2000).
Katz et al., "Comparison of risperidone and placebo for psychosis and behavioural disturbances associated with dementia: A randomized double-blind trial," Journal of Clinical Psychiatry 60(2):107-115 (1999).
Kay et al., "The Positive and Negative Syndrome Scale (PANSS) for Schizophrenia," Schizophrenia Bulletin, 13: 261-276 (1987).
Keck et al., "Anticonvulsants and Antipsychotics in the Treatment of Bipolar Disorder," J. Clin. Psychiatry, 59(suppl. 6):74-81 (1998).
Keck et al., "Antipsychotics in the Treatment of Mood Disorders and Risk of Tardive Dyskinesia," J. Clin. Psychiatry, 61(suppl. 4):33-38 (2000).
Keck et al., "Bipolar Disorder," Advances in the Pathophysiology and Treatment of Psychiatric Disorders: Implications for Internal Medicine, 85(3): 645-661 (2001).
Keck, Jr., "Treatment Advances in Bipolar Disorder—Making Up for Lost Time," Biological Psychiatry, 48(6):430-432 (2000).

(56) References Cited

OTHER PUBLICATIONS

Keck, Jr., et al., "Bipolar Disorder," Medical Clinics of North America, W.B. Saunders Company, Philadelphia, US, 3(85):645-661 (2001).
Keefe et al., "The Effects of Atypical Antipsychotic Drugs on Neurocognitive Impairment in Schizophrenia: A Review and Meta-analysis," Schizophr Bull, 25:201-222 (1999).
Kern et al., "An Open-label Comparison of the Neurocognitive Effects of Aripiprazole Versus Olanzapine in Patients With Stable Psychosis," Schizophr Res, 49(1-2); Suppl S:234 (2001).
Kern et al., "The Neurocognitive Effects of Aripiprazole: An Open-Label Comparison with Olanzapine," Psychopharmacology, 187:312-320 (2006).
Kikuchi et al., "7-{4-[4-(2,3-Dichlorophenyl)-1-Piperazinyl]Butyloxy}-3,4-Dihydro-2(1H)-Quinolinone (OPC-14597), a New Putative Antipsychotic Drug with Both Presynaptic Dopamine Autoreceptor Agonistic Activity and Postsynaptic D2 Receptor Antagonistic Activity," J. Pharm. Exp. Ther., 274:329-336 (1995).
Kikuchi et al., "Pharmacological profile of OPC-14597, a novel antipsychotic drug (1): Presynaptic dopamine autoreceptor agonistic activity and postsynaptic dopamine D2 receptor antagonistic activity," Japanese Journal of Pharmacology, 67(Suppl. 1):144P(1995).
Kleven et al., "Modification of behavioral effects of 8-hydroxy-2-(di-n-propylamino)tetralin following chronic ethanol consumption in the rat: evidence for the involvement of 5-HT1A receptors in ethanol dependence," Euro J. of Pharmacology, vol. 281, pp. 219-228 (1995).
Kohen & Sarcevic, "Central Sleep Apnea in a Geriatric Patient Treated with Aripiprazole," Am. J. Ther, 16(2):197-98 (2009).
Krowczynski et al., "Technologia Postaci Lekow," National Institute of Medical Publications, Warsaw, 1969, pp. 54-63, 78-81, 368-379.
Kuzmitcheva, "Powder Diffractometry in Materials Technology," part II, pp. 1-2, 75-76, 2006.
Laboratory Report by Ratiopharm, dated Sep. 22, 2008 (Document D38 referenced in the European Patent Office Submission of Ratiopharm GMBH in Opposition to European Patent No. 1330249, transmitted Jul. 2, 2010).
Laitinen, Experimental Report on Aripiprazole Batches, Dec. 18, 2006.
Lawler et al., "Interactions of the Novel Antipsychotic Aripiprazole (OPC-14597) with Dopamine and Serotonin Receptor Subtypes," Neuropsychopharmacology, 20(6):612-627 (1999).
Lee et al., "Effects of Clozapine on Cognitive Function in Schizophrenia," J. Clin. Psychiatry, vol. 55 (Suppl. B), pp. 82-87 (1994).
Leo & Del Regno, "Atypical Antipsychotic Use in the Treatment of Psychosis in Primary Care," Primary Care Companion J. Clin. Psychiatry, 2(6):194-204 (2000).
Letter of Opponent (Egis) regarding Opposition to European Patent No. 1330249, dated Nov. 28, 2014.
Letter of Opponent (Hexal AG) regarding Appeal T2059/13 of Opposition to European Patent No. 1712225, dated Apr. 3, 2014.
Letter of Opponent (Hexal AG) regarding Appeal T2059/13 of Opposition to European Patent No. 1712225, dated Sep. 24, 2014.
Letter of Opponent (Stada Arzneimittel AG) regarding Appeal T2059/13 of Opposition to European Patent No. 1712225, dated Apr. 10, 2014.
Letter of Opponent (Teva Pharmaceutical Industries Ltd.) regarding Appeal T2059/13 of Opposition to European Patent No. 1712225, dated Apr. 14, 2014.
Letter of Opponent (Teva) regarding Opposition to European Patent No. 1419776, dated Mar. 2, 2015.
Letter of Third Party dated Apr. 22, 2009, re Response of Mar. 26, 2009, to Examiners Re-examination Report of Australian Patent No. 2002334413 dated Jan. 28, 2009.
Lieberman et al. (eds), Pharmaceutical Dosage Forms (Marcel Dekker Inc, 2nd revised ed.), 1989, pp. 1-130.
Lieberman, "Atypical Antipsychotic Drugs as a First-Line Treatment of Schizophrenia: A Rationale and Hypothesis," Journal of Clinical Psychiatry, 57( Suppl. 11):68-71 (1996).
List of Queries to Panel of Experts by Otsuka Pharmaceutical Co., Ltd., dated Oct. 21, 2013, to the Office of the Honorable Judge of Istanbul 3rd Civil Court for Intellectual and Industrial Property Rights in File No. 2012/200E.
Lucki, "Behavioral Studies of Serotonin Receptor Agonists as Antidepressant Drugs," J. Clin. Psychiatry 52(12 Suppl.):24-31 (1991).
Lucot et al.,"Antiemetic effects of flesinoxan in cats: comparisons with 8-hydroxy-2-(di-n-propylamino) tetralin," Euro. J. of Pharmacology, vol. 253, pp. 53-60 (1994).
Lykouras et al., "Obsessive-compulsive symptoms induced by atypical antipsychotics. A review of reported cases," Progress in Neuro-Psychopharmacology & Biological Psychiatry, 27:333-346 (2003).
Lykouras et al., "Olanzapine and obsessive-compulsive symptoms," European Neuropsychopharmacology, 10:385-387 (2000).
Mahmood et al., "Serotonin and bipolar disorder," J. Affective Disorders, vol. 66: pp. 1-11 (2001).
Malhotra et al., "An Open Clinical Trial of Buspirone in Children with Attention-Deficit/Hyperactivity Disorder," J. Am. Acad. Child Adolesc. Psychiatry, 37(4):364-371 (1998).
Mallikaarjun et al., "The Pharmacokinetics, Tolerability, and Safety of Aripiprazole Following Single and Multiple Oral Dose Administration," Int J. Neuropsychopharmacol, 3 (Suppl) 1:Abst P01.123 (2000).
Manfredi et al., "Buspirone: Sedative or Stimulant Effect?" Am. J. Psychiatry, 148(9):1213-17 (1991) (abstract).
Manfredi et al., "Dr. Manfredi and Associates Reply" Am. J. Psychiatry, 150(5):845-46 (1993).
Mar. 1, 2012, Communication from European Patent Office, forwarding a copy of Teva Pharmaceutical Industries Ltd.'s Feb. 24, 2012, submission including DYC1 (Declaration of Professor Boese together with Enclosures I and II), DYC2 (Annex III of DYC1), and DYC3 (Repetition of D3, p. 938 final paragraph, lines 1-3).
Mar. 15, 2010, Communication from European Patent Office, forwarding a copy of letter from opponent 04, Egis Gyogyszergyar Nyrt, dated Mar. 2, 2010, regarding Appeal of EP Patent No. 1330249, including Document D33c (Microtrac Timeline with the part Legacy Microtrac Instrumentation, The Leeds & Northrup Years (1972-1993) with Series 7991, 7995, and 7997& SVR).
Mar. 5, 2012, Communication from European Patent Office, forwarding a copy of a letter from opponent 01, Teva Pharmaceutical Industries Ltd., dated Feb. 28, 2012, regarding Opposition to EP Patent No. 1419776B, including a signed version of Experimental Report DYC3 and Annexes 1 and 2.
Markens et al., "Conducting Stability Studies—Recent Changes to Climatic Zone IV," Life Science Technical Bulletin, Issue 13 (2009).
Mason et al., "Clozapine has sub-micromolar affinity for 5HT receptors in human brain tissue," Eur. J. Pharmacol., vol. 221, pp. 397-398 (1992).
Mason et al., "Clozapine has sub-micromolar affinity for 5-HT1A Receptors in Human Brain Tissue," Eur. J. Pharmacol., vol. 221: pp. 397-398 (1992).
Massimo et al., "5-HT1A Receptor hypersensitivity in migraine is suggested by the m-chlorophenylpiperazine test," NeuroReport vol. 9, pp. 2605-2608 (1998).
Matuszewich et al., "Partial antagonism of 8-OH-DPAT'S effects on male rat sexual behavior with a D2, but not a 5-HT1A, antagonist," Brain Research, 820:55-62 (1999).
McCormick, "Treatment with Buspirone in a Patient with Autism," Arch. Fam. Med., 6:368-370 (1997).
McDougle et al., "A Double-blind, Placebo-Controlled Study of Risperidone in Adults with Autistic Disorder and Other Pervasive Development Disorders," Arch. Gen. Psychiatry, 55:633-641 (1998).
McDougle et al., "Atypical Antipsychotics in Children and Adolescents with Autistic and Other Pervasive Developmental Disorders," J. Clin. Psychiatry, 69(Supp 4):15-20 (2008).
McDougle et al., "Lack of efficacy of clozapine monotherapy in refractory obsessive-compulsive disorder," Am. J. Psychiatry, 152(12):1812-1814 (1995) (Abstract).
McElroy et al., "Pharmacologic Agents for the Treatment of Acute Bipolar Mania," Biol. Psychiatry, 48:539-557 (2000).

(56) References Cited

OTHER PUBLICATIONS

Meltzer et al., "Does stimulation of 5-HT1A receptors improve cognition in schizophrenia?" Behavioural Brain Research, vol. 195 pp. 98-102 (2008).
Meltzer et al., "Multisystems and Circuitry Pharmacotherapy—Single or Multiple Receptor Targets: Which are Best for Antipsychotic Drugs," Neuropsychopharmacology 23(52):S73 (2000).
Meltzer et al., "Serotonin Receptors: Their Key Role in Drugs to Treat Schizophrenia," Progress in Neuro-Psychopharmacology & Biological Psychiatry, 27:1159-1172 (2003).
Meltzer, "Evaluating the effects of antipsychotics on cognition in schizophrenia," Journal of Clinical Psychiatry 59(Suppl. 12):35-40 (1998).
Meltzer, "Treatment-resistant schizophrenia—the role of clozapine," Current Medical Research and Opinion, 14(1):1-20 (1997).
Mendelson et al., "Effects of Buspirone on Sleep and Respiration," Am. Rev. Respir. Dis. 141:1527-1530 (1990).
Meneses et al., "5-HT1A Receptors Modulate the Consolidation of Learning in Normal and Cognitively Impaired Rats," Eur. J. Neurosci, vol. 71, pp. 207-218 (1999).
Merck Manual 17th ed. Japanese, Nikkei B P, p. 1569-1576, 1999.
Micheau et al., "Stimulation of 5-HT1A Receptors by Systemic or Medial Septum Injection Induces Anxiogenic-like Effects and Facilitates Acquisition of a Spatial Discrimination Task in Mice," Prog. Neuro-Pyschopharmacol. & Biol. Psychiat., 23:1113-1133 (1999).
Millan et al., "Improving the Treatment of Schizophrenia: Focus on Serotonin (5HT)1A Receptors," J. Pharmacol. Exp. Ther., 295(3):853-61 (2000).
MIMS Annual 2000, "Antipsychotic agents," pp. 3-258 to 3-281.
Mitsukuni, "Recent Trend of Development of Psychoactive Drugs (2)—Antipsychotic Drugs," Jpn. J. Psychopharmacol., 15(3):191-210 (1995).
Miyamoto et al.,"Developing novel antipsychotic drugs: strategies and goals," Current Opinion in CPNS Investigational Drugs, vol. 2, pp. 25 (2000).
Mohs, "Cognition in Schizophrenia: Natural History, Assessment, and Clinical Importance," Neuropsychopharmacology, 21(6):203-210 (1999).
Molewijk et al., "Conditioned ultrasonic distress vocalizations in adult male rats as a behavioural paradigm for screening anti-panic drugs," Psychopharmacology, 117:32-40 (1995).
Möller et al., "Are Antidepressants Less Effective in the Acute Treatment of Bipolar I Compared to Unipolar Depression?," J. Affective Disorders, vol. 67: pp. 141-146 (2001).
Monti et al., "Role of Dorsal Raphe Nucleus Serotonin 5-HT1A Receptor in the Regulation of REM Sleep," Life Sciences, 66(21):1999-2012 (2000).
Monti et al., "Sleep and Waking in 5,7-DHT-Lesioned or (–)-Pindolol-Pretreated Rats After Administration of Buspirone, Ipsapirone, or Gepirone," Pharmacology Biochemistry and Behavior, 52(2):305-312 (1995).
Morrison & Boyd, Organic Chemistry, p. 627, 1974.
Mullins et al., "Effects of Antidepressants on 5-HT7 Receptor Regulation in the Rat Hypothalamus," Neuropsychopharmacology, 21(3):352-367 (1999).
Muraviev, Technology of Medicinal Agents, vol. 1, Moscow, pp. 63-78, 114, 115, 1980.
Nagai et al., "Aripiprazole Ameliorates Phencyclidine-Induced Impairment of Recognition Memory through Dopamine D1 and Serotonin 5-HT1A Receptors," Psychopharmacology, 202:315-328 (2009).
Nanzando's Medical Dictionary, 1990, 17th Ed. p. 1571.
Newman-Tancredi et al., "Clozapine is a partial agonist at cloned, human serotonin 5-HT1A receptors," Neuropharmacology, 35(1):119-121 (1996).
Newman-Tancredi et al., "Neuropharmacological Profile of Bifeprunox: Merits and Limitations in Comparison with Other Third-Generation Antipsychotics," Current Opinion in Investigational Drugs, 8(7):539-554 (2007).
Nikkiso, "Microtrac particle distribution analyzers," http://www.nikkiso-b.co.jp/product_file/product1.htm, printed Jul. 20, 2007.
Nikolic & Beak, "(R)-(+)-2-(Diphenylhydroxymethyl)pyrrolidine," Organic Syntheses, 74:23 (1997).
Notice of Appeal, Federal Court of Australia, *Apotex Ptd.* v. *Otsuka Pharmaceuticals Inc.*, dated Jun. 10, 2014, Australian Patent No. 2009233591.
Notice of Information Disclosure by Third Party issued by the Japanese Patent Office in Japanese Patent Application No. 2007-179275 on May 31, 2010.
Nousiainen, Aripiprazole—Analytical Investigation, Dec. 19, 2006.
Novelli et al., "A Molecular Investigation Suggests No Relationship Between Obsessive-Compulsive Disorder and the Dopamine D2 Receptor," Neuropsychobiology, 29:61-63 (1994).
Novelty Search Report from Hungarian Application No. P0600141, dated Feb. 19, 2008.
Oct. 14, 2003, Communication from European Patent Office regarding EP Patent Application No. 02782507.4.
Odagaki et al., "5-HT1A Receptor Agonist Properties of Antipsychotics Determined by [35S] GTPγS Binding in Rat Hippocampal Membranes," Clinical and Experimental Pharmacology and Physiology, 34:462-466 (2007).
Office Action (Ex Parte Quayle Action) in U.S. Appl. No. 12/202,201 dated Jun. 1, 2010.
Office Action (final) in U.S. Appl. No. 13/327,607 dated Jun. 11, 2013.
Office Action (Final) dated Dec. 20, 2013 in U.S. Appl. No. 13/303,265.
Office Action (Final) dated Dec. 5, 2014, in U.S. Appl. No. 13/426,886.
Office Action (Final) dated Jun. 25, 2014, in U.S. Appl. No. 13/932,385.
Office Action from Japanese Patent Office issued in Japanese Patent Application No. 2007-179275 dated Apr. 13, 2011.
Office Action from Japanese Patent Office issued in Japanese Patent Application No. 2007-179275 dated Oct. 22, 2010.
Office Action in Japanese Application No. 2002-560616 dated Nov. 13, 2007.
Office Action in Japanese Patent Application No. 2011-133032 dated Feb. 28, 2014.
Office Action in Japanese Patent Application No. 2011-133032 dated May 14, 2013.
Office Action in Japanese Patent Application No. 2011-133033 dated Aug. 19, 2014.
Office Action in Japanese Patent Application No. 2011-133033 dated Feb. 28, 2014.
Office Action in Japanese Patent Application No. 2011-133033 dated May 14, 2013.
Office Action in Taiwanese Patent Application No. 098116881 dated May 17, 2010.
Office Action in U.S. Appl. No. 10/333,244 dated Apr. 29, 2009.
Office Action in U.S. Appl. No. 10/333,244 dated Feb. 26, 2007.
Office Action in U.S. Appl. No. 10/333,244 dated Jun. 11, 2008.
Office Action in U.S. Appl. No. 10/876,605 dated Apr. 10, 2009.
Office Action in U.S. Appl. No. 10/876,605 dated Aug. 23, 2010.
Office Action in U.S. Appl. No. 10/876,605 dated Dec. 9, 2009.
Office Action in U.S. Appl. No. 10/876,605 dated Mar. 3, 2008.
Office Action in U.S. Appl. No. 10/876,605 dated May 16, 2007.
Office Action in U.S. Appl. No. 11/790,504 dated Sep. 29, 2009.
Office Action in U.S. Appl. No. 11/790,603 dated Dec. 28, 2009.
Office Action in U.S. Appl. No. 11/790,604 dated May 24, 2010.
Office Action in U.S. Appl. No. 11/790,605 dated Apr. 26, 2010.
Office Action in U.S. Appl. No. 11/790,606 dated Dec. 11, 2009.
Office Action in U.S. Appl. No. 11/797,019 dated Jan. 7, 2010.
Office Action in U.S. Appl. No. 11/797,019 dated Nov. 22, 2011.
Office Action in U.S. Appl. No. 11/797,024 dated Jan. 25, 2010.
Office Action in U.S. Appl. No. 11/797,024 dated Nov. 22, 2011.
Office Action in U.S. Appl. No. 11/797,030 dated Mar. 10, 2010.
Office Action in U.S. Appl. No. 11/932,795 dated Apr. 15, 2009.
Office Action in U.S. Appl. No. 11/932,795 dated Dec. 17, 2009.
Office Action in U.S. Appl. No. 11/932,795 dated Feb. 18, 2011.
Office Action in U.S. Appl. No. 11/932,795 dated Jun. 14, 2010.
Office Action in U.S. Appl. No. 12/202,192 dated Jan. 7, 2010.
Office Action in U.S. Appl. No. 12/202,201 dated Oct. 20, 2009.
Office Action in U.S. Appl. No. 12/202,208 dated Feb. 24, 2011.

(56) References Cited

OTHER PUBLICATIONS

Office Action in U.S. Appl. No. 12/202,208 dated Jun. 14, 2010.
Office Action in U.S. Appl. No. 12/830,740 dated May 27, 2011.
Office Action in U.S. Appl. No. 13/067,750 dated Jul. 5, 2012.
Office Action in U.S. Appl. No. 13/067,750 dated May 22, 2013.
Office Action in U.S. Appl. No. 13/067,838 dated Aug. 1, 2012.
Office Action in U.S. Appl. No. 13/067,838 dated Aug. 29, 2013.
Office Action in U.S. Appl. No. 13/067,838 dated May 21, 2013.
Office Action in U.S. Appl. No. 13/185,879 dated Apr. 30, 2012.
Office Action in U.S. Appl. No. 13/195,954 dated Aug. 13, 2012.
Office Action in U.S. Appl. No. 13/303,265 dated Aug. 20, 2012.
Office Action in U.S. Appl. No. 13/327,607 dated Jun. 1, 2012.
Office Action in U.S. Appl. No. 13/327,607 dated Nov. 8, 2012.
Office Action in U.S. Appl. No. 13/327,618 dated Jul. 9, 2013.
Office Action in U.S. Appl. No. 13/426,886 dated Apr. 3, 2014.
Office Action in U.S. Appl. No. 13/426,886 dated May 15, 2015.
Office Action in U.S. Appl. No. 13/426,886 dated May 28, 2013.
Office Action in U.S. Appl. No. 13/426,886 dated Sep. 26, 2012.
Office Action in U.S. Appl. No. 13/476,758 dated Aug. 7, 2013.
Office Action in U.S. Appl. No. 13/476,773 dated Jun. 20, 2013.
Office Action in U.S. Appl. No. 13/749,753 dated May 21, 2014.
Office Action in U.S. Appl. No. 13/932,385 dated Dec. 17, 2013.
Office Action in U.S. Appl. No. 14/049,777 dated Jul. 16, 2015.
Ohmori et al., "Late Phase II Study of Aripiprazole for Schizophrenia," JP Journal of clinical Psychopharmacology, vol. 9, No. 2, Feb. 2006.
Ongini et al., "Differential Effects of Dopamine D-1 and D-2 Receptor Antagonist Antipsychotics on Sleep-Wake Patterns in the Rat," J. Pharmaco. Exp. Therap., 266:726-731 (1993).
Ongini et al., "Effects of Remoxipride, a Dopamine D-2 Antagonist Antipsychotic, on Sleep-Waking Patterns and EEG Activity in Rats and Rabbits," Psychopharmacology, 107:236-242 (1992).
Opposition in Indian Patent Application No. IN/PCT/2002/1536 dated Jan. 8, 2010, by Torrent Pharmaceuticals Ltd., including Exhibits 1A, 3A-3C, and 5 (67 pages).
Oshiro et al.; "Novel Antipsychotic Agents with Dopamine Autoreceptor Agonist Properties: Synthesis and Pharmacology of 7-[4-(4-Phenyl-1-piperazinyhbutoxy]-3,4-dihydro-2(1H)-quinolinone Derivatives;" Journal of Med. Chemistry, 41(5):658-667, (1998).
Otsuka Pharmaceutical Co., Ltd, Additional note in support of interlocutory injunction application dated Mar. 9, 2012, in case No. NSD 121/2012 concerning Australian Patent Nos. 2002226752 and 2005201772.
Otsuka Pharmaceutical Co., Ltd, Submission in support of interlocutory injunction application dated Mar. 5, 2012, in case No. NSD 121/2012 concerning Australian Patent Nos. 2002226752 and 2005201772 (including Annexure A).
Ozdemir, "Aripiprazole Otsuka Pharmaceutical Co Ltd," Current Opinion in CPNS Investigational Drugs, 2(1):105-111 (2000).
Parada et al., "Rats Self-Inject a Dopamine Antagonist in the Lateral Hypothalamus Where It Acts to Increase Extracellular Dopamine in the Nucleus Accumbens," Pharmacology Biochemistry and Behavior, 52(1):179-187 (1995).
Partial English translation of Merck Manual 17th ed. Japanese, Nikkei BP, p. 1569-1576, 1999.
Partial English translation of Office Action in Japanese Patent Application No. 2011133032 dated May 14, 2013.
Partial English translation of Office Action in Japanese Patent Application No. 2011133033 dated May 14, 2013.
Partial English translation of submission of Sanovel Ilac Sanayi Ve Ticaret Anonim Sirketi in opposition to Turkish Patent No. TR2006/0246, dated Feb. 25, 2013.
Partial English translation of Yamada et al., "Effect of OPC-14597 on the stimulant-induced dopamine release in rat striatal slices," Japanese Journal of Psychopharmacology, vol. 16, p. 238 (1996).
Partial translation of Rinsyou Seisin Yakuri, "Aripiprazole," Japanese Journal of Clinical Psychopharmacology, 9:2503-2511 (2006).
Particulars of Invalidity in case No. NSD 121/2012 for Australian Patent Nos. 2002226752 and 2005201772, dated Feb. 10, 2012, by Generic Health Pty Ltd.

Pecknold et al., "Gepirone and the Treatment of Panic Disorder: An Open Study," Journal of Clinical Psychopharmacology 13(2):145-149 (1993).
Pérez, Experimental Report on Aripiprazole, Nov. 17, 2003.
Perry, Manual del Ingeniero Quimico, vol. 1, 3rd Edition, p. 1239 (1981).
Pessina et al., "Aripiprazole augmentation of serotonin reuptake inhibitors in treatment-resistant obsessive-compulsive disorder: a 12-week open-label preliminary study," Int. Clin. Psychopharmacol., 24:265-269 (2009).
Petition of Sanovel Ilac Sanayi Ve Ticaret A.S. regarding Turkish patent TR 2006 02467 T4, submitted to the Istanbul 3rd Civil Court of Intellectual and Industrial Property Rights on Jun. 6, 2013.
Petrie et al., "Aripiprazole, a new typical antipsychotic: Phase 2 clinical trial result," European Neuropsychopharmacology 7(Suppl 2):S227 (1997).
Petrie., "Acute and Long-Term Efficacy and Safety of Aripiprazole: A New Atypical Antipsychotic," Schizophrenia Research, 29 (1-2):155 (1998).
Pfaus et al., "Role of Dopamine in Anticipatory and Consummatory Aspects of Sexual Behavior in the Male Rat," Behavioral Neuroscience, 105:727-743 (1991 ).
Planowski et al., "Procesy i aparaty w technologii chemicznej," WNT, Warsaw (1974), p. 765-771.
Pleadings before Arbitrazh Court of Moscow case No. A40-115364/12-12-530 by Otsuka Pharmaceutical Co., Ltd. dated Nov. 20, 2012.
Poltronieri et al., "Antipanic-like Effect of Serotonin Reuptake Inhibitors in the Elevated T-maze," Behavioural Brain Research, 147:185-192 (2003).
Pomerantz, "Quinelorane (LY163502), a D2 Dopamine Receptor Agonist, Acts Centrally to Facilitate Penile Erections of Male Rhesus Monkeys," Pharmacol. Biochem. Behav., 39:123-128 (1991).
Potenza et al., "Olanzapine treatment of children, adolescents, and adults with pervasive developmental disorders: an open-label pilot study," J. Clin. Psychopharmacol., 19(1):37-44 (1999) (Abstract).
Prinssen et al., "Interactions between neuroleptics and 5-HT1A ligands in preclinical behavioral models for antipsychotic and extrapyramidal effects," Psychopharmacology, 144(1):20-29 (1999).
Privitera et al., "Clozapine in a Bipolar Depressed Patient", Am. J. Psychiatry, 150(6):986 (1993).
Puel et al., Polymorphism in Fine Organic Processes, LAGEP UMR CNRS 5007, Université Lyon 1 ESCPE. Bât. 308G, 43 Bd. du Nov. 11, 1918. F-69622 Villeurbanne, France.
Purdon,, "Long-Term Treatment With Quetiapine Improves Cognitive Function in Schizophrenia," Biol. Psychiatry, 47:42 (2000).
Rasmussen et al.,"Chapter 1. Recent Progress in Serotonin (5-HT)1 A Receptor Modulators," in Annual Reports in Medicinal Chemistry, vol. 30, pp. 1-9 (1995).
Rawla, "Basic Principles of Particle Size Analysis," published by Malvern Instruments, pp. 1-8 (printed from the European Patent Office with a timestamp of Jan. 4, 2007).
Ray, "CINP 2000—Collegium Internationale Neuro-Psychopharmacologicum 22nd Congress," Drugs, 3(9):1023-1025 (2000) (abstract).
Realmuto et al. "Clinical Effect of Buspirone in Autistic Children," J. Clin. Pyschopharmacol., 9(2):122-125 (1989).
Remington Farmacia, 1985, 17th Edition, pp. 1911-1920.
Remington Farmacia, 2000, 20th Edition, pp. 824 and 828.
Report DYC1 of Siglait Levi signed Jun. 4, 2013, submitted by Teva Pharmaceutical Industries Ltd. on Jun. 11, 2013, in opposition to EP Application No. 02782507.4/EP Patent No. 1330249.
Request for declaratory judgment on lack of infringement by Generica Ilac Sanayi Ve Tic A.S. dated Mar. 27, 2013, before the Istanbul Court on Duty for Intellectual and Industrial Rights.
Request for Re-examination of Australian Patent No. 2002226752 (dated Sep. 19, 2008).
Request for Re-examination of Australian Patent No. 200233413 (dated May 1, 2006).
Request for Re-examination of Australian Patent No. 2002334413 (dated Sep. 19, 2008).
Request for Re-examination of Australian Patent No. 2005201772 (dated Sep. 19, 2008).

(56) References Cited

OTHER PUBLICATIONS

Response dated Jun. 4, 2009, to Examiners Re-Examination Report dated Jan. 28, 2009, including Third Statement of Voluntary Amendments.
Response of Mar. 26, 2009, to Re-Examination Report of Australian Patent No. 2002334413 dated Jan. 28, 2009, including Second Statement of Voluntary Amendments.
Response of Nov. 23, 2006, to Examiners Re-examination Report of Australian Patent No. 2002334413 dated Oct. 10, 2006, including First Statement of Voluntary Amendments.
Revised European Patent Office Submission of Teva Pharmaceutical Industries Ltd. in Opposition to European Patent No. 1330249B1, dated Apr. 27, 2009.
Reynolds, "The new antipsychotics—Some pharmacological aspects of their problems and potential," Expert Opinion on Pharmacotherapy 1(2):181-185 (2000).
Rhodes, Introduction to Particle Technology, John Wiley & Sons, Chichester, 1998, pp. 69-70.
Rinsyou Seisin Yakuri, "Aripiprazole," Japanese Journal of Clinical Psychopharmacology, 9:2503-2511 (2006).
Rivas-Vazquez et al., "Atypical Antipsychotic Medications: Pharmacological Profiles and Psychological Implications," Professional Psychology: Research and Practice, 31(6):628-640 (2000).
Robinson et al., "Clinical Effects of the 5HT1A Partial Agonists in Depression: A Composite Analysis of Buspirone in the Treatment of Depression," J. Clin. Psychopharmacol., 10(3 Suppl):67S-76S (1990).
Rosenheck et al., "A Comparison of Clozapine and Haloperidol in Hospitalized Patients with Refractory Schizophrenia," The New England Journal of Medicine, 337(12):809-815 (1997).
Rund, BR., "How Do Neuroleptics Affect Cognitive Dysfunctions in Schizophrenia?," Nord. J. Psychiatry 53(2):121-125 (1999).
Rusk et al., "Profile of the Selective Dopamine D-2 Receptor Agonist N-0437: Its Effect on Palatability-and Deprivation-Induced Feeding, and Operant Responding for Food," Physiology & Behavior, 44:545-553 (1988).
Russian Patent Office Submission of Egis Gyógyszergyár Nyrt in Opposition to Russian Patent No. 2259366 (Application No. 2003101334), including Enclosure 1, transmitted Oct. 5, 2011.
Sachs et al., "The Expert Consensus Guideline Series, Medication Treatment of Bipolar Disorder 2000," A Postgraduate Medicine Special Report, pp. 1-20, Apr. 2000.
Saha et al., "Safety and Efficacy Profile of Aripiprazole, a Novel Antipsychotic," Schizophr. Res, 36(1-3):295 (1999).
Sasa et al., "Unique Pharmacological Profile of a Novel Antipyschotic Drug, Aripiprazole (OPC-14597)", CNS Drug Reviews, 3(1):24-33 (1997).
Schafer et al., "Effects of parkinsonian medication on sleep," J Neurol, 247(Suppl 4):IV/24-IV/27 (2000).
Schechter et al., "The potential utility of 5-HT1A receptor antagonists in the treatment of cognitive dysfunction associated with Alzheimer's disease," Curr. Pharm. Des., vol. 8, No. 2, pp. 139-145 (2002) (Abstract).
Schmidt, Aripiprazol Experimental Report and Attachments I and II, Dec. 23, 2006.
Scrip News Letter 2000 No. 2580, p. 11 (Oct. 4, 2000).
Seidl et al., "Serotonin (5-HT) in brains of adult patients with Down Syndrome," J. Neural Transm., 57(supp):221-232 (1999).
Seifritz et al., "The 5-HT1A agonist ipsapirone enhances EEG slow wave activity in human sleep and produces a power spectrum similar to 5-HT2 blockade," Neuroscience Letters 209:41-44 (1996).
Serper et al., "Novel Neuroleptics Improve Attentional Functioning in Schizophrenic Patients: Ziprasidone and Aripiprazole," CNS Spectrums, 2(8): 56-59 (1997).
Shapiro et al., "Aripiprazole, A Novel Atypical Antipsychotic Drug with a Unique and Robust Pharmacology," Neuropsychopharmacology, vol. 28, pp. 1400-1411 (2003).
Sharma et al., "The Cognitive Efficacy of atypical antipsychotics in schizophrenia," J. of Clinical Psychopharm., vol. 18, pp. 12S-19S (1998).
Sheehan et al., "The Relative Efficacy of High-dose Buspirone and Alprazolam in the Treatment of Panic Disorder: A Double-blind Placebo-controlled Study," Acta Psychiatr. Scand., 88(1):1-11 (1993).
Shiah et al., "Cortisol, Hypothermic, and Behavioral Responses to Ipsapirone in Patients with Bipolar Depression and Normal Controls," Neuropsychobiology, 38:6-12 (1998).
Shin-Shiah et al., "Cortisol, Hypothermic, and Behavioral Responses to Ipsapirone in Patients with Bipolar Depression and Normal Controls," Neuropsychobiology, vol. 38(6): pp. 6-12 (1998).
Specification for the thermogravimetric analyzer SDT Q-600, printed on Jul. 18, 2011.
Stahl et al., "Effectiveness of ipsapirone, a 5-HT-1A partial agonist, in major depressive disorder: support for the role of 5-HT-1A receptors in the mechanism of action of serotonergic antidepressants," International Journal of Neuropsychopharmacology 1:11-18 (1998).
Stahl et al., "Stahl's Illustrated Antipsychotics: Treating Psychosis, Mania and Depression," Cambridge University Press (2nd ed. 2010).
Stahl, "Dopamine System Stabilizers, Aripiprazole, and the Next Generation of Antipsychotics, Part 1—'Goldilocks' Actions at Dopamine Receptors," J. Clin. Psychiatry 62(11):841-842 (2001).
Stahl, "Dopamine System Stabilizers, Aripiprazole, and the Next Generation of Antipsychotics, Part 2—Illustrating Their Mechanism of Action," J. Clin. Psychiatry 62(12):923-924 (2001).
Stahl, Essential Psychopharmacology of Depression and Bipolar Disorder, Ed. 1, Cambridge University Press, p. 148, 2000.
Stam et al., "Human Serotonin 5-HT7 Receptor: Cloning and Pharmacological Characterisation of Two Receptor Variants," FEBS Letters 412, pp. 489-494 (1997).
Statement of Claims before the Arbitrazh Court of Moscow of Egish Died'Jserdiar Nail'Jvanoshan Mukede Resven'Jtarshashag on recognition of the decision of the Federal Service on intellectual property of May 17, 2012 (referenced in Pleadings before Arbitrazh Court of Moscow case No. A40-115364/12-12-530 by Otsuka Pharmaceutical Co., Ltd. dated Nov. 20, 2012).
Statement of Grounds and Particulars by Apotex Pty Ltd in opposition Australian Patent Application No. 2009233591, dated Feb. 21, 2013.
Statement of Grounds and Particulars dated Apr. 20, 2012, for Australian Patent Application No. 2009233591 by Apotex Pty. Ltd.
Statement of Grounds of Opposition dated Apr. 20, 2012, for Australian Patent Application No. 2009233591 by Alphapharm Pty. Limited.
Statement of Grounds of Opposition filed on Dec. 17, 2010, for Australian Patent No. 2007201701 by Alphapharm Pty. Ltd.
Statutory Declaration by James Ellsmore filed in support of the Amended Statement of Grounds of Opposition filed Mar. 17, 2011, for Australian Patent No. 2007201701 by Alphapharm Pty. Ltd (including exhibits JE1-JE8).
Statutory Declaration by Julian Parmegiani filed in support of the Amended Statement of Grounds of Opposition filed Mar. 17, 2011, for Australian Patent No. 2007201701 by Alphapharm Pty. Ltd (including exhibits JE1-JE17).
Statutory Declaration of Bruce Sugriv Singh dated Aug. 21, 2013, concerning opposition to Australian Patent Application No. 2009233591.
Statutory Declaration of Bruce Sugriv Singh dated Mar. 14, 2012, concerning the opposition to Australian Patent Application No. 2007201701 (including Exhibits BSS-3 to BSS-8).
Statutory Declaration of Jayashri Kulkarni dated Nov. 21, 2013, concerning the opposition to Australian Patent Application No. 2009233591, including Exhibit JK-7.
Statutory Declaration of Paula de Bruyn dated Aug. 21, 2013, concerning opposition to Australian Patent Application No. 2009233591.
Stellman, Encyclopedia of Occupational Health and Safety, 4th Ed., p. 7811, 1998.
Stigler et al., "Case Report: Aripiprazole for Maladaptive Behavior in Pervasive Development Disorders," J. Child and Adolescent Psychopharmacology, 14(3):455-463 (2004).
Striegel, Aripiprazol Experimental Report, Dec. 21, 2006.
Submission of Opponent (Egis) regarding Opposition to European Patent No. 1330249 (Results of water uptake measurements), dated Oct. 30, 2014.

(56) References Cited

OTHER PUBLICATIONS

Submission of Opponent (Egis) regarding Opposition to European Patent No. 1330249 (Solid state characterization of aripiprazole samples), dated Nov. 26, 2014.
Submission of Opponent (Egis) regarding Opposition to European Patent No. 1330249 (Summary of laboratory experiments on crystallization and drying of aripiprazole), dated Mar. 11, 2014.
Submission of questions to experts of Sanovel Ilac Sanayi Ve Ticaret A.S. dated Oct. 21, 2013, to the Office of the Honorable Judge of Istanbul 3rd Civil Court for Intellectual and Industrial Property Rights in File No. 2012/200E.
Submission of Ratiopharm GMBH dated Jun. 11, 2013 regarding opposition to EP Application No. 02782507.4/EP Patent No. 1330249.
Submission of Sanovel Ilac Sanayi Ve Ticaret A.S. dated Dec. 29, 2014, to the Office of the Honorable Judge of Istanbul 3rd Civil Court for Intellectual and Industrial Property Rights in File No. 2012/200E, regarding Patent No. TR 2006/02467 T4.
Submission of Sanovel Ilac Sanayi Ve Ticaret A.S. dated Nov. 21, 2013, to the Office of the Honorable Judge of Istanbul 3rd Civil Court for Intellectual and Industrial Property Rights in File No. 2012/200E.
Submission of Sanovel Ilac Sanayi Ve Ticaret Anonim Sirketi in opposition to Turkish Patent No. TR2006/0236, dated Feb. 25, 2013.
Submission of Sanovel Ilac Sanayi Ve Ticaret Anonim Sirketi to the Office of the Honorable Judge of Istanbul 4th Civil Court for Intellectual and Industrial Property Rights in respect of the invalidation of the patent with No. TR 2006/02467 T4, dated Aug. 2, 2012.
Submission of Teva Pharmaceutical Industries Ltd. dated Jun. 11, 2013, regarding opposition to EP Application No. 02782507.4/EP Patent No. 1330249.
Sumiyoshi et al., "Effect of adjunctive treatment with serotonion-1a agonist tandospirone on memory functions in schizophrenia," J. Clin. Pharmacol., vol. 20, pp. 386-388 (2000).
Sumiyoshi et al., "Tandospirone, a serotonin-1A agonist, added to neuroleptic treatment enhances cognitive performance in schizophrenia," Database accession No. PREV200200022926, Society for Nueroscience Abstracts (2001).
Summons to Attend Oral Proceedings from European Patent Office, regarding European Patent Application No. 06015782.3 (European Patent No. 1712225), dated Apr. 12, 2010.
TA Instruments, "Thermal Analysis Application Brief: Kinetics of Drying by Thermogravimetric Analysis," No. TA-134.
Tamai et al., "The Clinical Efficacy of a 5-HT1A Agonist, SM-3997, In the Treatment of Bulimia," International Journal of Obesity, 14:289-292 (1990).
Tamminga & Lahti, "Treatments for chronic psychosis," Dialogues in Clinical Neuroscience, 3(4):281-291 (2001).
Tanninen, Test Report on Aripiprazole, Dec. 19, 2006.
Taylor et al., "Treatment of acute mania or hypomania," The South London and Maudsley NHS Trust 2001 Prescribing Guidelines, 6th Edition (2001).
Test Report No. 32 of the X-Ray Diffraction Laboratory of the National Commission of Atomic Energy, Argentina.
Test Report No. 33 of the X-Ray Diffraction Laboratory of the National Commission of Atomic Energy, Argentina, dated Aug. 25, 2003.
The Merck Index—Aripiprazole, 2001.
The Merck Manual, 17th Ed., 1999, pp. 2233-2236.
The United States Pharmacopeia (USP) 29, pp. 2788-2789, (2006).
Tohen & Zarate, "Antipsychotic Agents and Bipolar Disorder," J. Clin. Psychiatry, 59(suppl. 1):38-48 (1998).
Tohen et al., "Effect of Olanzapine in Acute Bipolar Mania," Arch. Gen. Psychiatry, vol. 57 (9): pp. 841-849 (2000).
Tramontina et al., "Aripiprazole in Juvenile Bipolar Disorder Comorbid with Attention-Deficit/Hyperactivity Disorder: An Open Clinical Trial," CNS Spectr., 12(10):758-762 (2007).
Translation of Opposition Brief as submitted to the European Patent Office by patent attorneys Maiwald Patentanwaltsgesellschaft mbH, dated Feb. 25, 2008.
Trunko et al., "Aripiprazole in Anorexia Nervosa and Low-Weight Bulimia Nervosa: Case Reports," International Journal of Eating Disorders, vol. 44, No. 3, pp. 269-275, 2011.
Tunnicliff, "Molecular Basis of Buspirone's Anxiolytic Action," Pharmacology & Toxicology, 69:149-156 (1991).
U.S. Pharmacopeia, "X-Ray Diffraction," Section 941: 2088-2089 (2002).
Vieta et al., "Effectiveness of Aripiprazole v. Haloperidol in Acute Bipolar Mania, Double-blind, Randomised, Comparative 12-week Trial," British Journal of Psychiatry, 187:235-242 (2005).
Vippagunta et al., "Crystalline Solids," Advanced Drug Delivery Reviews 48:3-26 (2001).
Vogel, Vogel's Textbook of Practical Organic Chemistry, Including Qualitative Organic Analysis (Longman Scientific & Technical, 4th revised ed.), 1987, pp. 110-125.
Wade & Weller., Handbook of Pharmaceutical Excipients, American Pharmaceutical Association, Washington, and the Pharmaceutical Press, London, 1994, 2nd Ed., pp. 1-2.
Wang et al., The Effect of Physical Environment of Crystallization Process on the Polymorph of Ciprofloxacin Hydrochloride, School of Chemical Engineering and Technology, Tianjin University, Tianjin, 300072, P. R. China, 15th International Symposium onIndustrial Crystallization 1(2):623-628 (2002).
Ward et al., "Forebrain serotonin depletion facilitates the acquisition and performance of a conditional visual discrimination task in rats," Behavioral Brain Research, 100:51-65 (1999).
Wedd, "Determination of Particle Size Distribution Using Laser Diffraction," Educ. Reso. for Part. Techn., 032Q-Wedd (2003).
Wickremaratch & Morris, "Aripiprazole Associated with Severe Exacerbation of Parkinson's Disease," Movement Disorders, 21(9):1538-1539 (2006).
Wolff et al., "Effects of a 5-HT receptor agonist on acute and delayed 1A cyclophosphamide-induced vomiting," Euro J. of Pharmacology, vol. 340, pp. 217-220 (1997).
Wolfgang Beckmann, "Seeding the Desired Polymorph: Background, Possibilities, Limitations, and Case Studies," Chemical Engineering Department, Chemical Development, Schering AG, 13342 Berlin, Jul. 6, 2000.
Yamada et al., "Effect of OPC-14597 on the stimulant-induced dopamine release in rat striatal slices," Japanese Journal of Psychopharmacology, vol. 16, p. 238 (1996).
Yamada et al., Society of Neuroscience Abstracts 26 (1-2), No. - 871.7 (2000).
Yau, "Impact of Adrenalectomy on 5-HT6 and 5-HT7 Receptor Gene Expression in the Rat Hippocampus," Molecular Brain Research 45:182-186 (1997).
Yeung et al., "Efficacy of aripiprazole, a novel antipsychotic, in schizophrenia and schizoaffective disorder: Results of a placebo-controlled trial with risperidone," Eur. Neuropsychopharm. 11(Suppl. 3): S259 (2001).
York, "The design of dosage forms," in Pharmaceutics: The Science of Dosage Form Design (Aulton ed., Churchill Livingston), 1988, pp. 1-13.
Zakrzewsk & Marek, Solid State Characterization of Pharmaceuticals, 2006, pp. 134-135 and 152.
Zhang, "Regulation of the Central Opioidergic Nervous System on the Emotional State of Anxiety and its Possible Mechanisms," Sheng Li Ke Xue Jin Zhan, 28(1):41-44 (1997).
Aulton, Pharmaceutics: The Science of Dosage Form Design, Churchill Livingstone Press, p. 237 (1988).
Communication from the European Patent Office, dated Aug. 24, 2015, Observations filed by a third party, regarding Application No. EP08000358.3.
Byrn, "Pharmaceutical Solids: A Strategic Approach to Regulatory Considerations," Pharmaceutical Research, 12 (7): 945-954 (1995).
Communication from the European Patent Office, dated Jul. 22, 2015, regarding EP1330249, Appeal No. T0777/15-3.3.02.
Notice of Appeal, submitted by Dowa, dated 2015, Trial Brief regarding Korean Patent No. 10-0763288.

(56) References Cited

OTHER PUBLICATIONS

Notice of Appeal, submitted by Eishin, dated 2015, Trial Brief regarding Korean Patent No. 763288.
Fonyo et al., "Basic Chemical Operations," National Textbook Publisher Budapest, pp. 901-902 (1998).
English translation of Fonyo et al., "Basic Chemical Operations," National Textbook Publisher Budapest, pp. 901-902 (1998).
Letter of Appeal by Polpharma, regarding Opposition to EP1330249, dated Jul. 2, 2015.
Letter of Appeal by Fermion, regarding Opposition to EP1330249, dated Jun. 17, 2015.
European Pharmacopoeia 5.4: Residual Solvents, pp. 507-515.
Gennaro, Remington: The Science and Practice of Pharmacy, 20th Edition, Lippincott Williams & Wilkins, pp. 656-657 (2001).
Lachman et al., The Theory and Practice of Industrial Pharmacy, 3rd Edition, Lea & Febiger, pp. 181-182 (1986).
Wolff et al., "Comparison of the Antiemetic Effects of a 5HT1A Agonist, LY228729, and 5HT3 Antagonists in the Pigeon," Pharm. Biochem. and Behavior, vol. 52, pp. 571-575 (1995).
Office Action in U.S. Appl. No. 13/426,886, dated Oct. 26, 2016.
Office Action in U.S. Appl. No. 15/149,522, dated Oct. 6, 2016.
Submission by Daewoong Pharma. Co. regarding Invalidation action of Korean Patent No. 10-0490222, dated Oct. 5, 2016.
English translation of submission by Daewoong Pharma. Co. regarding Invalidation action of Korean Patent No. 10-0490222, mailed Oct. 5, 2016.
Submission in Invalidation Trial of JP 5683010, dated Nov. 19, 2016.
English translation of submission in Invalidation Trial of JP 5683010, dated Nov. 19, 2016.
EPO communication, regarding Opposition to EP1330249, dated Nov. 9, 2016.
English translation of Decision in Invalidation Action of Korean Patent No. 763288, dated Oct. 28, 2016.
EPO communication, regarding Opposition to EP1330249, dated Feb. 2, 2017.
EPO communication, regarding Opposition to EP1330249, dated Mar. 2, 2017.
English translation of Plaintiffs Brief (Youngjin) in Invalidation Trial of Korean Patent No. 10-763288, dated Dec. 15, 2016.
EPO communication, Notice of Opposition to EP1925308, dated Apr. 18, 2017.
Submission of Opponent (Polpharma) in Opposition to EP 1925308, dated Apr. 10, 2017.
"Guidance for Industry: Dissolution Testing of Immediate Release Solid Oral Dosage Forms," U.S. dept. Health Human Serv. FDA CDER, Aug. 1997.
Experimental Report by Pharmaceutical Works Polpharma S.A., submitted in Opposition to EP 1925308, dated Mar. 2017.
Experimental Report by Pharmaceutical Works Polpharma S.A., submitted in Opposition to EP 1925308, dated Dec. 2016.
Bandelin, "Compressed Tablets by Wet Granulation," in Lieberman et al (eds), Pharmaceutical Dosage Forms (Marcel Dekker Inc, 2nd revised ed.), pp. 131-193 (1989).
Rucinic, "Oral Solid Dosage Forms," in Remington: The Science and Practice of Pharmacy, 20th Edition, Gennaro (Ed.), Lippincott Williams & Wilkins, Chapter 45, pp. 858-893 (2000).
Arnt, J. et. al. "Do Novel Antipsychotics Have Similar Pharmacological Characteristics? A Review of the Evidence," Neuropsychopharmacology, vol. 18, No. 2, pp. 63-101 (1998).
Meneses, A. et. al. "A Pharmacological Analysis of Serotonergic Receptors: Effects of Their Activation of Blockage in Learning," Prog, Neuropsychopharmacol. Biol. Psychiatry, vol. 21 (Feb) (2), pp. 273-296 (1997).
Meltzer H. et. al. "The Role of Serotonin in Antipsychotic Drug Action," Neuropsychopharmacology, vol. 21, No. 2S, p. 106S-117S (1999).
Pre-Grant Opposition Decision for Indian Patent Application No. IN/PCT/2002/1536, dated Feb. 20, 2018.

KR Invalidation Trial Against Patent No. 0490222, Trail Case No. 2016 Dang5, Petitioner's Brief received on Dec. 20, 2017 (Korean).
KR Invalidation Trial Against Patent No. 0490222, Trail Case No. 2016 Dang5, Petitioner's Brief received on Dec. 20, 2017 (English).
KR Invalidation Trial Against Patent No. 0490222, Trail Case No. 2016 Dang5, Otsuka's Technical Presentation Material, filed on Jan. 17, 2018 (Korean).
KR Invalidation Trial Against Patent No. 0490222, Trail Case No. 2016 Dang5, Otsuka's Technical Presentation Material, filed on Jan. 17, 2018 (English).
KR Invalidation Trial Against Patent No. 0490222, Trail Case No. 2016 Dang5, Petitioner's Technical Presentation dated Jan. 17, 2018 (Korean).
KR Invalidation Trial Against Patent No. 0490222, Trail Case No. 2016 Dang5, Petitioner's Technical Presentation (cover) dated Jan. 17, 2018.
KR Invalidation Trial Against Patent No. 0490222, Trail Case No. 2016 Dang5, Petitioner's Technical Presentation dated Jan. 17, 2018.
KR Invalidation Trial Against Patent No. 0490222, Trail Case No. 2016 Dang5, Petitioner's Brief received on Jan. 31, 2018 (filed on 29).
Reference 7 (The USFDA, 'Clinical Pharmacology and Biopharmaceutics Review(s) regarding original aripiprazole Center for Drug Evaluation and Research, Application No. 21-436, Clinical Pharmacology and Biopharmaceutics Review(s), pp. 1-4) of KR Invalidation Trial Against Patent No. 0490222, Trail Case No. 2016 Dang5, Petitioner's Brief received on Jan. 31, 2018 (filed on 29).
Reference 8 (Khadka, P., et al. "Pharmaceutical particle technologies: An approach to improve drug solubility, dissolution and bioavailability," Asian Journal of Pharmaceutical Sciences, 9 (2014) pp. 304-316) of KR Invalidation Trial Against Patent No. 0490222, Trail Case No. 2016 Dang5, Petitioner's Brief received on Jan. 31, 2018 (filed on 29).
Reference 9 (Korean Patent Publication No. 1981-0000956) of KR Invalidation Trial Against Patent No. 0490222, Trail Case No. 2016 Dang5, Petitioner's Brief received on Jan. 31, 2018 (filed on 29).
Reference 10 (Korean Patent Publication No. 1989-0005303) of KR Invalidation Trial Against Patent No. 0490222, Trail Case No. 2016 Dang5, Petitioner's Brief received on Jan. 31, 2018 (filed on 29).
Reference 11 (Korean Patent No. 045249) of KR Invalidation Trial Against Patent No. 0490222, Trail Case No. 2016 Dang5, Petitioner's Brief received on Jan. 31, 2018 (filed on 29).
KR Invalidation Trial Against Patent No. 0490222, Trail Case No. 2016 Dang5, Petitioner's Brief received on Jan. 31, 2018 (filed on 30).
Reference 12 (The booklet 'Methods for Dissolution Test,' published by the Ministry of Food and Drug Safety (2012)) from KR Invalidation Trial Against Patent No. 0490222, Trail Case No. 2016 Dang5, Petitioner's Brief received on Jan. 31, 2018 (filed on 30).
KR Invalidation Trial Against Patent No. 0490222, Trail Case No. 2016 Dang5, Otsuka's Brief filed Jan. 29, 2018 (Korean).
KR Invalidation Trial Against Patent No. 0490222, Trail Case No. 2016 Dang5, Otsuka's Brief filed Jan. 29, 2018 (English).
Exhibit E-5 (Aripiprazole Type-II Heat at 135 deg C., p. 1) of KR Invalidation Trial Against Patent No. 0490222, Trail Case No. 2016 Dang5, Otsuka's Brief filed Jan. 29, 2018.
Exhibit E-5-1 (Translation of Exhibit E-5) of KR Invalidation Trial Against Patent No. 0490222, Trail Case No. 2016 Dang5, Otsuka's Brief filed Jan. 29, 2018.
Exhibit E-10 (Remington, The Science and Practice of Pharmacy, 21st Edition, 2006, pp. 672-673, 1027, 1039, 1040) of KR Invalidation Trial Against Patent No. 0490222, Trail Case No. 2016 Dang5, Otsuka's Brief filed Jan. 29, 2018.
Exhibit E-10-1 (Excerpted translation of Exhibit E-10) of KR Invalidation Trial Against Patent No. 0490222, Trail Case No. 2016 Dang5, Otsuka's Brief filed Jan. 29, 2018.
Exhibit E-11 (edited by Min-Hwa Lee, Young-Soon Ku, New Pharmaceutical Science, pp. 614-617) of KR Invalidation Trial Against Patent No. 0490222, Trail Case No. 2016 Dang5, Otsuka's Brief filed Jan. 29, 2018.

(56) References Cited

OTHER PUBLICATIONS

Exhibit E-12 (Korean Pharmacopeia, general experimental methods, 42. Dissolution test) of KR Invalidation Trial Against Patent No. 0490222, Trail Case No. 2016 Dang5, Otsuka's Brief filed Jan. 29, 2018.
Exhibit E-13 (Aripiprazole Tablets, Revision Bulletin, dated Oct. 1, 2017, pp. 1-4) of KR Invalidation Trial Against Patent No. 0490222, Trail Case No. 2016 Dang5, Otsuka's Brief filed Jan. 29, 2018.
Exhibit E-13-1 (Excerpted translation of Exhibit E-13) of KR Invalidation Trial Against Patent No. 0490222, Trail Case No. 2016 Dang5, Otsuka's Brief filed Jan. 29, 2018.
Exhibit E-14 (Applicant's Reply to EPO Communication from the Examining Division, dated Sep. 8, 2008, pp. 1-6, European patent application (No. 04 002 427.5)) of KR Invalidation Trial Against Patent No. 0490222, Trail Case No. 2016 Dang5, Otsuka's Brief filed Jan. 29, 2018.
Exhibit E-14-1 (Excerpted translation of Exhibit E-14) of KR Invalidation Trial Against Patent No. 0490222, Trail Case No. 2016 Dang5, Otsuka's Brief filed Jan. 29, 2018.
Exhibit E-15 (Comparative XRD data Type I, Type 2, and Crystal C) of KR Invalidation Trial Against Patent No. 0490222, Trail Case No. 2016 Dang5, Otsuka's Brief filed Jan. 29, 2018.
Dunn et al, "A prospective, open label study of Aripiprazole mono- and adjuntive treatment in acute bipolar depression," Journal of Affective Disorders, 110 (2008) pp. 70-74.
Mazza, "Beneficial acute antidepressant effects of aripiprazole as an adjunctive treatment or monotherapy in bipolar patients unresponsive to mood stabilizers: results form a 16-week open-label trial," Expert Opinion on Pharmacotherapy, vol. 9, No. 18, (2008), pp. 3145-3149.
Office Action dated Mar. 9, 2018, U.S. Appl. No. 15/494,877.
Reference 3 from the KR Invalidation Trial Against Patent No. 0490222, Trail Case No. 2016 Dang5, Otsuka's Technical Presentation Material, filed on Jan. 17, 2018 (Korean).
KR Invalidation Trial Against Patent No. 0490222, Trail Case No. 2016 Dang5, Otsuka's Brief, filed on Feb. 14, 2018.

\* cited by examiner

LOW HYGROSCOPIC ARIPIPRAZOLE DRUG SUBSTANCE AND PROCESSES FOR THE PREPARATION THEREOF

RELATED APPLICATIONS

This application is a continuation of application Ser. No. 13/749,753, filed Jan. 25, 2013, which is a continuation of application Ser. No. 11/790,604, filed Apr. 26, 2007, now U.S. Pat. No. 8,399,469, issued Mar. 19, 2013, which is a division of application Ser. No. 10/333,244, now abandoned, which is a §371 of International Application No. PCT/JP02/09858, filed Sep. 25, 2002, which claims priority of Japanese Application Nos. JP 2001-290645, filed Sep. 25, 2001, and JP 2001-348276, filed Nov. 14, 2001, and of Canadian Application No. CA 2379005, filed Mar. 27, 2002, the contents of all of which are incorporated by reference.

DETAILED DESCRIPTION OF THE INVENTION

Field of the Invention

The present invention relates to an improved form of aripiprazole having reduced hygroscopicity and processes for the preparation of this improved form.

Background of the Invention

Aripiprazole, 7-{4-[4-(2,3-dichlorophenyl)-1-piperazinyl]-butoxy}-3,4-dihydro carbostyril or 7-{4-[4-(2,3-dichlorophenyl)-1-piperazinyl]-butoxy}-3,4-dihydro-2(1H)-quinolinone, is an atypical antipsychotic agent useful for the treatment of schizophrenia (U.S. Pat. No. 4,734,416 and U.S. Pat. No. 5,006,528). Schizophrenia is a common type of psychosis characterized by delusions, hallucinations and extensive withdrawal from others. Onset of schizophrenia typically occurs between the age of 16 and 25 and affects 1 in 100 individuals worldwide. It is more prevalent than Alzheimer's disease, multiple sclerosis, insulin-dependent diabetes and muscular dystrophy. Early diagnosis and treatment can lead to significantly improved recovery and outcome. Moreover, early therapeutic intervention can avert costly hospitalization.

According to Example 1 of Japanese Unexamined Patent Publication No. 191256/1990, anhydrous aripiprazole crystals are manufactured for example by reacting 7-(4-bromobutoxy)-3,4-dihydrocarbostyril with 1-(2,3-dichlorophenylpiperadine and recrystallizing the resulting raw anhydrous aripiprazole with ethanol. Also, according to the Proceedings of the 4th Japanese-Korean Symposium on Separation Technology (Oct. 6-8, 1996), anhydrous aripiprazole crystals are manufactured by heating aripiprazole hydrate at 80° C. However, the anhydrous aripiprazole crystals obtained by the aforementioned methods have the disadvantage of being significantly hygroscopic.

The hygroscopicity of these crystals makes them difficult to handle since costly and burdensome measures must be taken in order ensure they are not exposed to moisture during process and formulation. Exposed to moisture, the anhydrous form can take on water and convert to a hydrous form. This presents several disadvantages. First, the hydrous forms of aripiprazole have the disadvantage of being less bioavailable and less dissoluble than the anhydrous forms of aripiprazole. Second, the variation in the amount of hydrous versus anhydrous aripiprazole drug substance from batch to batch could fail to meet specifications set by drug regulatory agencies. Third, the milling may cause the drug substance, Conventional Anhydrous Aripiprazole, to adhere to manufacturing equipment which may further result in processing delay, increased operator involvement, increased cost, increased maintenance and lower production yield. Fourth, in addition to problems caused by introduction of moisture during the processing of these hygroscopic crystals, the potential for absorbance of moisture during storage and handling would adversely affect the dissolubility of aripiprazole drug substance. Thus shelf-life of the product could be significantly decreased and/or packaging costs could be significantly increased. It would be highly desirable to discover a form of aripiprazole that possessed low hygroscopicity thereby facilitating pharmaceutical processing and formulation operations required for producing dosage units of an aripiprazole medicinal product having improved shelf-life, suitable dissolubility and suitable bioavailability.

Also, Proceedings of the 4th Japanese-Korean Symposium on Separation Technology (Oct. 6-8, 1996) state that, anhydrous aripiprazole crystals exist as type-I crystals and type-II crystals; the type-I crystals of anhydrous aripiprazole can be prepared by recrystallizing from an ethanol solution of aripiprazole, or by heating aripiprazole hydrate at 80° C.; and the type-II crystals of anhydrous aripiprazole can be prepared by heating the type-I crystals of anhydrous aripiprazole at 130 to 140° C. for hours.

By the aforementioned methods, anhydrous aripiprazole type-II crystals having high purity can not be easily prepared in an industrial scale with good repeatability.

SUMMARY OF THE INVENTION

Thus according to the present invention is provided a form of aripiprazole having reduced hygroscopicity and which is more amenable to pharmaceutical processing and formulation. The inventors of the present invention have discovered that this reduced-hygroscopic form of Aripiprazole is a crystalline substance defined herein as Anhydrous Aripiprazole Crystals B. A particular process for the preparation of this anhydrous crystalline substance has also been discovered and comprises yet another aspect of the present invention. Particularly, it was discovered as part of the present invention that in order to produce Anhydrous Aripiprazole Crystals B having the desired pharmaceutical properties and utilizing the most efficient process, Hydrate A, as defined herein, would have to serve as the intermediate. It was also discovered that a particular sequence of processing had to be implemented in order to form Hydrate A. It was discovered that the preparation of Hydrate A required milling what is defined herein as Conventional Hydrate. Then, Hydrate A can be transformed into Anhydrous Aripiprazole Crystals B through suitable heating as defined herein. Surprisingly, if the Conventional Hydrate is first heated and then milled, serious agglomeration sets in rendering the processing commercially unsuitable.

An object of the present invention is to provide novel anhydrous aripiprazole crystals.

Moreover, another object of the present invention is to provide anhydrous aripiprazole crystals which neither easily convert into hydrates nor substantially decrease the original solubility, even when a pharmaceutical composition comprising anhydrous aripiprazole is stored for a long period of time.

Further object of the present invention is to provide preparation methods, in order to obtain anhydrous aripiprazole crystals having high purity in an industrial scale with good repeatability.

The present inventors have conducted research works aimed to attain the aforementioned objects. In the course of the research, they have found that the desired anhydrous aripiprazole crystals can be obtained when a well-known anhydrous aripiprazole is heated at the specific temperature. Further, the present inventors have found that the desired anhydrous aripiprazole crystals can be obtained from recrystallization of a well-known anhydrous aripiprazole by using the specific solvents. Moreover, the present inventors found that the desired anhydrous aripiprazole crystals can be obtained by suspending a well-known anhydrous aripiprazole in the specific solvent, and heating thus obtained suspension.

The present invention thus completed on the basis of these findings and knowledge.

DETAILED DESCRIPTION OF THE INVENTION

Figure 3:
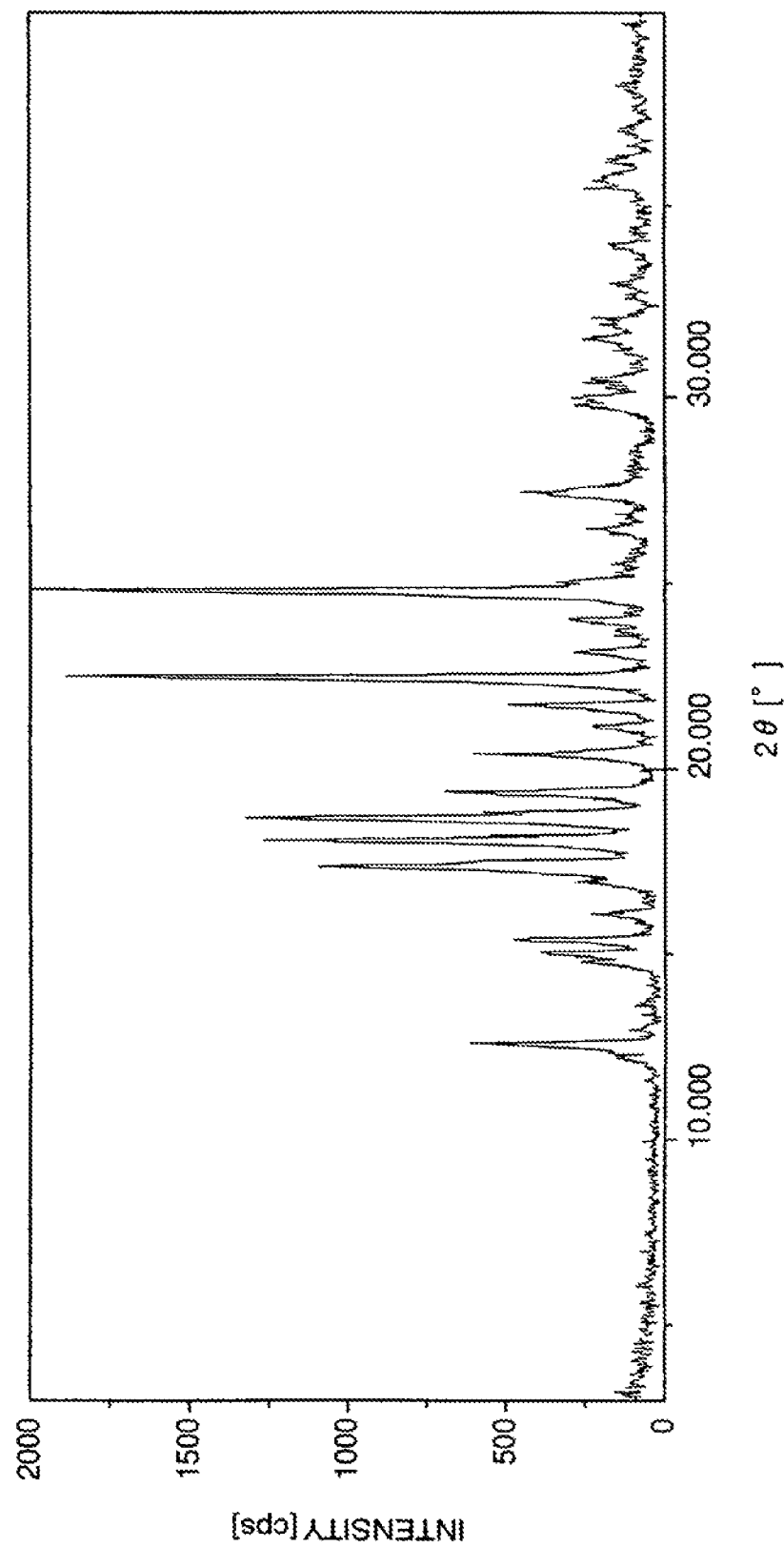
FIG. 3 is a powder x-ray diffraction diagram of the Aripiprazole Hydrate A obtained in Example 1.

According to first embodiment of the first aspect of the present invention is provided Hydrate A of aripiprazole wherein said Hydrate has a powder x-ray diffraction spectrum which is substantially the same as the powder x-ray diffraction spectrum shown in FIG. 3.

According to another embodiment of the first aspect of the present invention is provided Hydrate A of aripiprazole wherein said Hydrate has powder x-ray diffraction characteristic peaks at 2θ=12.6°, 15.4°, 17.3°, 18.0°, 18.6°, 22.50 and 24.8°.

According to another embodiment of the first aspect of the present invention is provided Hydrate A of aripiprazole wherein said Hydrate has particular infrared absorption bands at 2951, 2822, 1692, 1577, 1447, 1378, 1187, 963 and 784 cm$^{-1}$ on the IR (KBr) spectrum.

Figure 2:
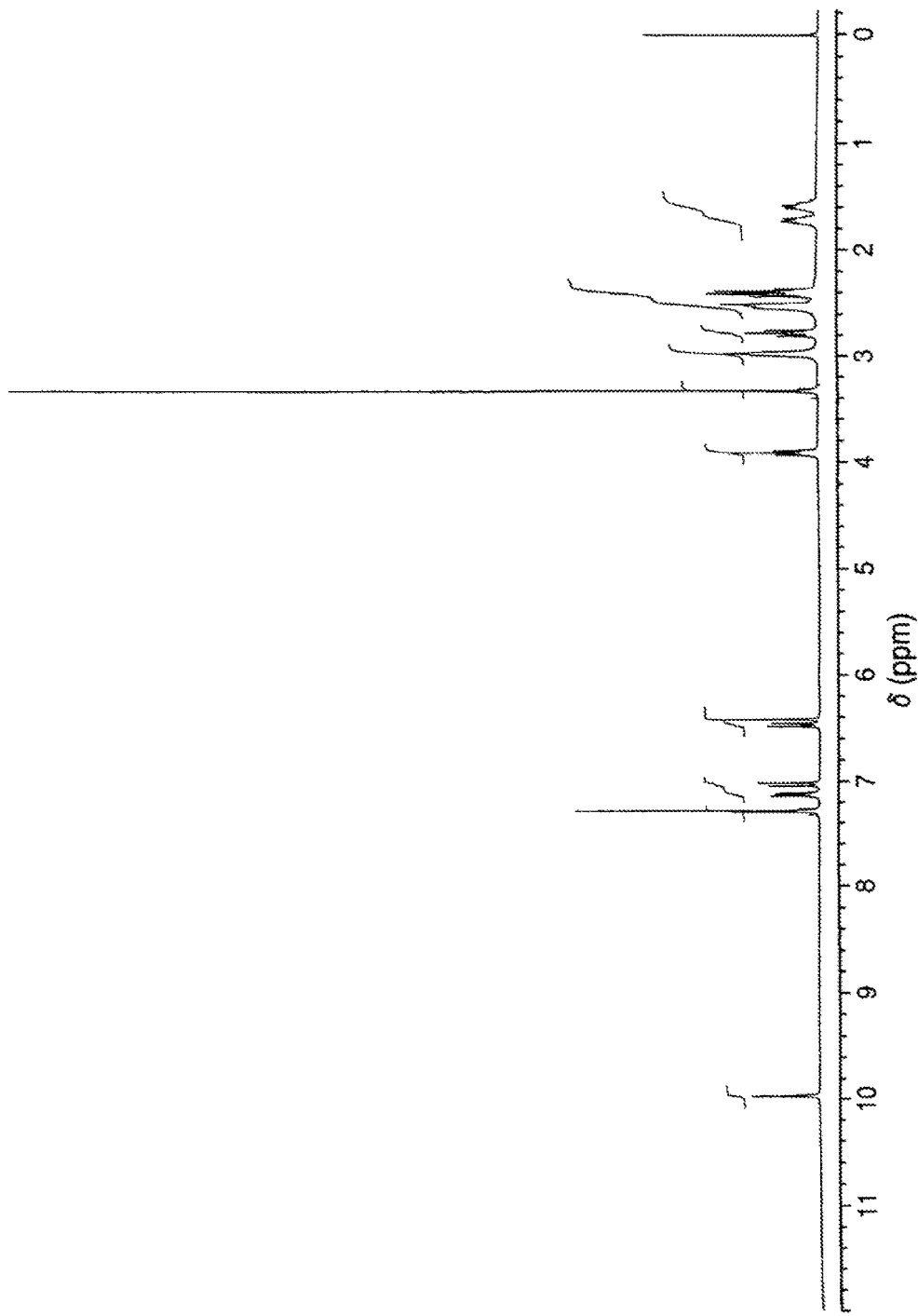
FIG. 2 shows the $^1$H-NMR spectrum (DMSO-de, TMS) of the Aripiprazole Hydrate A obtained in Example 1.

According to another embodiment of the first aspect of the present invention is provided Hydrate A of aripiprazole wherein said Hydrate has an $^1$H-NMR spectrum which is substantially the same as the $^1$H-NMR spectrum (DMSO-$d_6$, TMS) shown in FIG. 2.

According to another embodiment of the first aspect of the present invention is provided Hydrate A of aripiprazole wherein said Hydrate has an $^1$H-NMR spectrum (DMSO-$d_6$, TMS) having characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 1:
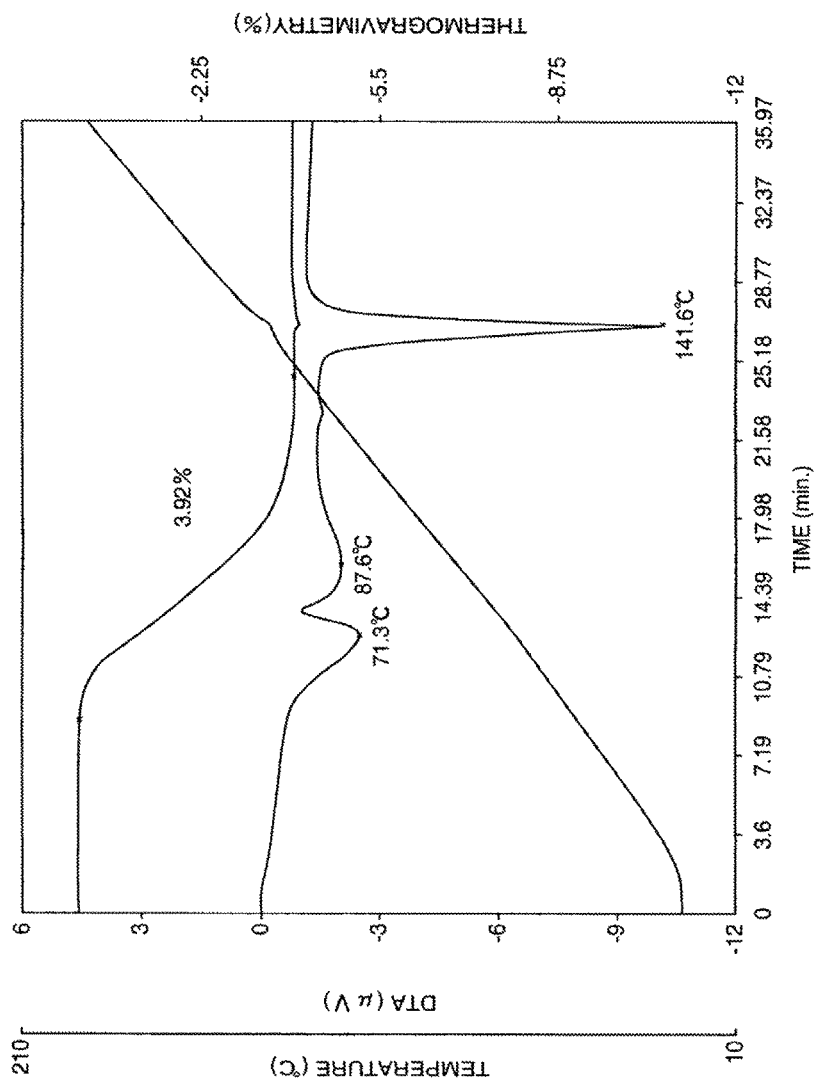
FIG. 1 is a thermogravimetric/differential thermogram of the Aripiprazole Hydrate A obtained in Example 1.

According to another embodiment of the first aspect of the present invention is provided Hydrate A of aripiprazole wherein said Hydrate has an endothermic curve which is substantially the same as the thermogravimetric/differential thermal analysis (heating rate 5° C./min) endothermic curve shown in FIG. 1.

According to another embodiment of the first aspect of the present invention is provided Hydrate A of aripiprazole wherein said Hydrate has a mean particle size of 50 μm or less.

According to another embodiment of the first aspect of the present invention is provided Hydrate A of aripiprazole wherein said Hydrate has a mean particle size of 40 μm or less.

According to another embodiment of the first aspect of the present invention is provided Hydrate A of aripiprazole wherein said Hydrate has a mean particle size of 35 μm or less.

According to another embodiment of the first aspect of the present invention is provided Hydrate A of aripiprazole wherein said Hydrate has a mean particle size of 30 μm or less.

According to another embodiment of the first aspect of the present invention is provided Hydrate A of aripiprazole wherein said Hydrate has a mean particle size of 25 μm or less.

According to another embodiment of the first aspect of the present invention is provided Hydrate A of aripiprazole wherein said Hydrate has a mean particle size of 20 μm or less.

According to another embodiment of the first aspect of the present invention is provided Hydrate A of aripiprazole wherein said Hydrate has a mean particle size range of 40 to 10 μm.

According to another embodiment of the first aspect of the present invention is provided Hydrate A of aripiprazole wherein said Hydrate has a mean particle size range of 36 to 14 μm.

According to a second aspect of the present invention is provided a process for the preparation of Hydrate A wherein said process comprises the steps of milling Conventional Hydrate.

According to a first embodiment of the second aspect of the present invention is provided a process for the preparation of Hydrate A comprising the steps of milling Conventional Hydrate wherein said milling is performed by a milling machine.

According to another embodiment of the second aspect of the present invention is provided a process for the preparation of Hydrate A comprising the steps of milling Conventional Hydrate wherein said milling machine is an atomizer, pin mill, jet mill or ball mill.

According to another embodiment of the second aspect of the present invention is provided a process for the preparation of Hydrate A comprising the steps of milling Conventional Hydrate wherein said milling machine is an atomizer.

According to another embodiment of the second aspect of the present invention is provided a process for the preparation of Hydrate A comprising the steps of milling Conventional Hydrate wherein said milling machine is an atomizer using a rotational speed of 5000-15000 rpm for the main axis, a feed rotation of 10-30 rpm and a screen hole size of 1-5 mm.

According to various embodiments of a third aspect of the present invention is provided Hydrate A defined according to one or more of the embodiments described herein wherein said Hydrate is made by a process as described herein.

According to a fourth aspect of the present invention is provided aripiprazole drug substance of low hygroscopicity.

According to a first embodiment of the fourth aspect of the present invention is provided aripiprazole drug substance of low hygroscopicity wherein said low hygroscopicity is a moisture content of 0.5% or less after placing said drug substance for 24 hours in a dessicator maintained at a temperature of 60° C. and a humidity level of 100%.

According to a first embodiment of the fourth aspect of the present invention is provided aripiprazole drug substance of low hygroscopicity wherein said low hygroscopicity is a moisture content of 0.4% or less after placing said drug substance for 24 hours in a dessicator maintained at a temperature of 60° C. and a humidity level of 100%.

According to another embodiment of the fourth aspect of the present invention is provided aripiprazole drug substance of low hygroscopicity wherein said low hygroscopicity is a moisture content of 0.25% or less after placing said drug substance for 24 hours in a dessicator maintained at a temperature of 60° C. and a humidity level of 100%.

According to another embodiment of the fourth aspect of the present invention is provided aripiprazole drug substance of low hygroscopicity wherein said low hygroscopicity is a moisture content of 0.15% or less after placing said drug substance for 24 hours in a dessicator maintained at a temperature of 60° C. and a humidity level of 100%.

According to another embodiment of the fourth aspect of the present invention is provided aripiprazole drug substance of low hygroscopicity wherein said low hygroscopicity is a moisture content of 0.10% or less after placing said drug substance for 24 hours in a dessicator maintained at a temperature of 60° C. and a humidity level of 100%.

According to another embodiment of the fourth aspect of the present invention is provided aripiprazole drug substance of low hygroscopicity wherein said low hygroscopicity is a moisture content of 0.05% or less after placing said drug substance for 24 hours in a dessicator maintained at a temperature of 60° C. and a humidity level of 100%.

According to another embodiment of the fourth aspect of the present invention is provided aripiprazole drug substance of low hygroscopicity wherein said low hygroscopicity is a moisture content of 0.04% or less after placing said drug substance for 24 hours in a dessicator maintained at a temperature of 60° C. and a humidity level of 100%.

According to another embodiment of the fourth aspect of the present invention is provided aripiprazole drug substance of low hygroscopicity wherein said drug substance is Anhydrous Aripiprazole Crystals B as defined herein.

Figure 5:
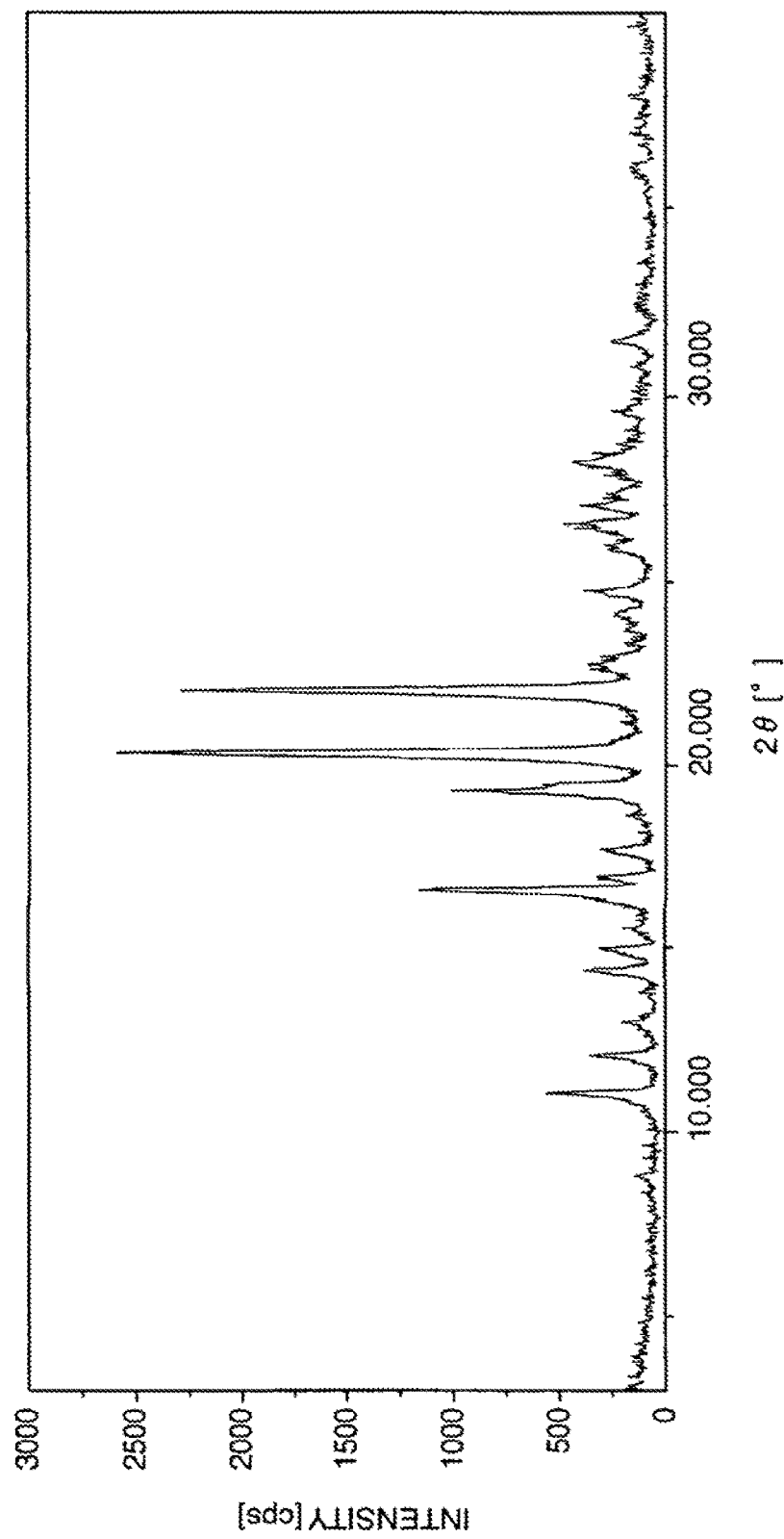
FIG. 5 is a powder x-ray diffraction diagram of the Anhydrous Aripiprazole Crystals B obtained in Example 2.

According to another embodiment of the fourth aspect of the present invention is provided aripiprazole drug substance of low hygroscopicity wherein said drug substance has a powder x-ray diffraction spectrum which is substantially the same as the powder x-ray diffraction spectrum shown in FIG. 5.

According to another embodiment of the fourth aspect of the present invention is provided aripiprazole drug substance of low hygroscopicity wherein said drug substance has a powder x-ray diffraction spectrum having characteristic peaks at 2θ=11.0°, 16.6°, 19.3°, 20.3° and 22.1°.

According to another embodiment of the fourth aspect of the present invention is provided aripiprazole drug substance of low hygroscopicity wherein said drug substance has particular infrared absorption bands at 2945, 2812, 1678, 1627, 1448, 1377, 1173, 960 and 779 $cm^{-1}$ on the IR (KBr) spectrum.

Figure 4:
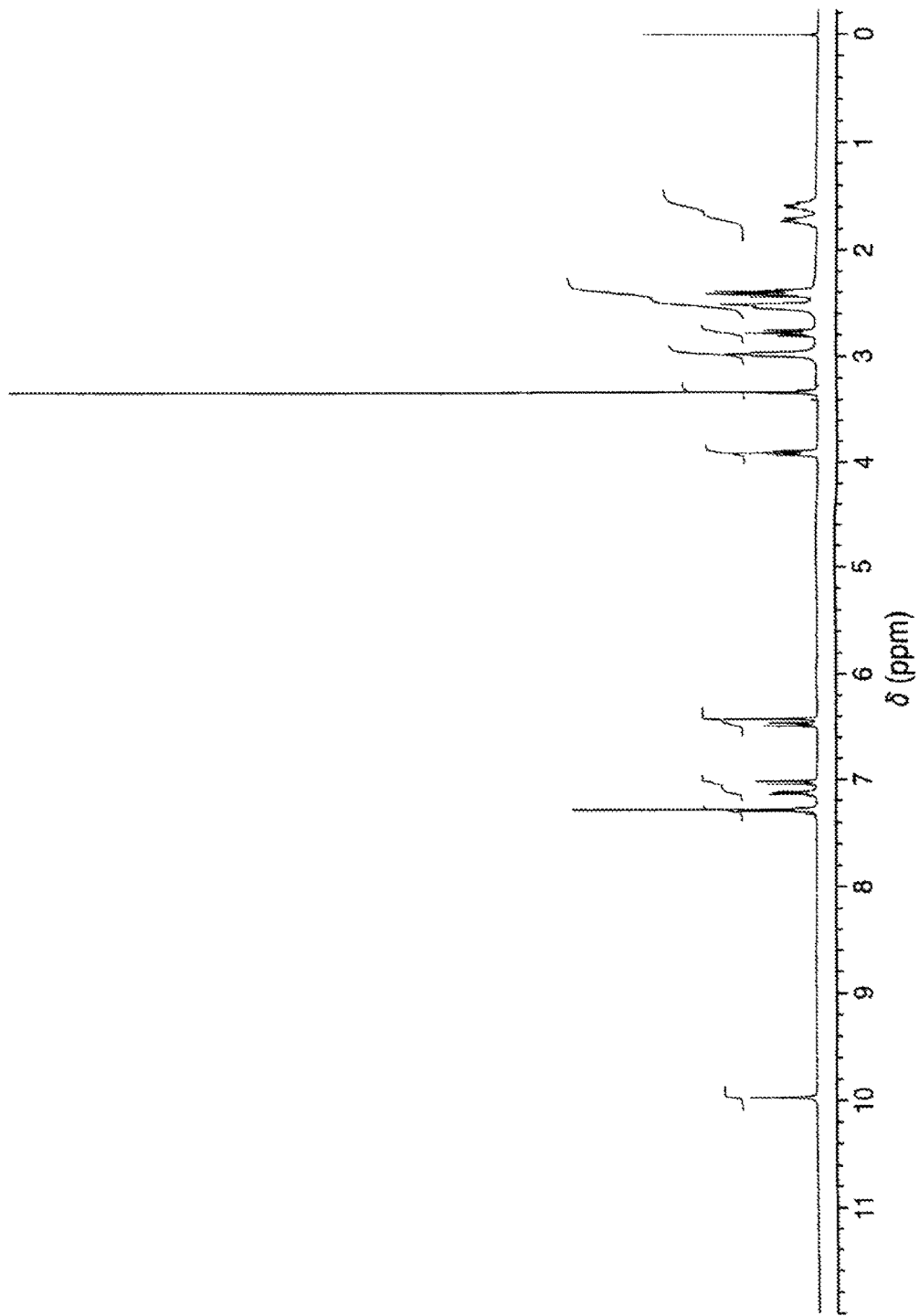
FIG. 4 shows the $^1$H-NMR spectrum (DMSO-$d_6$, TMS) of the Anhydrous Aripiprazole Crystals B obtained in Example 2.

According to another embodiment of the fourth aspect of the present invention is provided aripiprazole drug substance of low hygroscopicity wherein said drug substance has an ¹H-NMR spectrum which is substantially the same as the ¹H-NMR spectrum (DMSO-d₆, TMS) shown in FIG. 4.

According to another embodiment of the fourth aspect of the present invention is provided aripiprazole drug substance of low hygroscopicity wherein said drug substance has an ¹H-NMR spectrum (DMSO-d₆, TMS) having characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 1.0.00 ppm (s, 1H).

According to another embodiment of the fourth aspect of the present invention is provided aripiprazole drug substance of low hygroscopicity wherein said drug substance exhibits an endothermic peak near about 141.5° C. in thermogravimetric/differential thermal analysis (heating rate 5° C./min).

According to another embodiment of the fourth aspect of the present invention is provided aripiprazole drug substance of low hygroscopicity wherein said drug substance exhibits an endothermic peak near about 140.7° C. in differential scanning calorimetry (heating rate 5° C./min).

According to another embodiment of the fourth aspect of the present invention is provided aripiprazole drug substance of low hygroscopicity wherein said drug substance is Anhydrous Aripiprazole Crystals B and will not substantially convert to a hydrous form of aripiprazole when properly stored even for an extended period. For instance, said Anhydrous Aripiprazole Crystals B can be stored under a relative humidity (RH) of 60% and at a temperature of 25° C., even for a period not less than 1 year.

According to another embodiment of the fourth aspect of the present invention is provided aripiprazole drug substance of low hygroscopicity wherein said drug substance is Anhydrous Aripiprazole Crystals B and will not substantially convert to a hydrous form of aripiprazole when properly stored even for an extended period. For instance, said Anhydrous Aripiprazole Crystals B can be stored under a relative humidity (RH) of 60% and at a temperature of 25° C., even for a period not less than 4 years.

According to another embodiment of the fourth aspect of the present invention is provided aripiprazole drug substance of low hygroscopicity wherein said drug substance is Anhydrous Aripiprazole Crystals B and will not substantially convert to a hydrous form of aripiprazole when properly stored even for a period not less than 0.5 year under a relative humidity (RH) of 75% and at a temperature of 40° C.

According to another embodiment of the fourth aspect of the present invention is provided aripiprazole drug substance of low hygroscopicity wherein said drug substance has a mean size of 50 μm or less when small particle size is required for the formulation such as Tablet and other solid dose formulations including for example flashmelt formulations.

According to another embodiment of the fourth aspect of the present invention is provided aripiprazole drug substance of low hygroscopicity wherein said drug substance has a mean size of 40 μm or less if small particle size is required for the formulation such as Tablet and other solid dose formulations including for example flashmelt formulations.

According to another embodiment of the fourth aspect of the present invention is provided aripiprazole drug substance of low hygroscopicity wherein said drug substance has a mean size of 30 μm or less if small particle size is required for formulation such as Tablet and other solid dose formulations including for example flashmelt formulations.

According to a fifth aspect of the present invention is provided a process for the preparation of Anhydrous Aripiprazole Crystals B.

According to a first embodiment of the fifth aspect of the present invention is provided a process for the preparation of Anhydrous Aripiprazole Crystals B wherein said process comprises heating Aripiprazole Hydrate A.

According to a first embodiment of the fifth aspect of the present invention is provided a process for the preparation of Anhydrous Aripiprazole Crystals B wherein said process comprises heating Aripiprazole Hydrate A at 90-125° C. for about 3-50 hours.

According to another embodiment of the fifth aspect of the present invention is provided a process for the preparation of Anhydrous Aripiprazole Crystals B wherein said process comprises heating Aripiprazole Hydrate A at 100° C. for about 18 hours.

According to another embodiment of the fifth aspect of the present invention is provided a process for the preparation of Anhydrous Aripiprazole Crystals B wherein said process comprises heating Aripiprazole Hydrate A at 100° C. for about 24 hours.

According to another embodiment of the fifth aspect of the present invention is provided a process for the preparation of Anhydrous Aripiprazole Crystals B wherein said process comprises heating Aripiprazole Hydrate A at 120° C. for about 3 hours.

According to another embodiment of the fifth aspect of the present invention is provided a process for the preparation of Anhydrous Aripiprazole Crystals B wherein said process comprises heating Aripiprazole Hydrate A for about 18 hours at 100° C. followed by additional heating for about 3 hours at 120° C.

According to a sixth aspect of the present invention is provided Anhydrous Aripiprazole Crystals B defined according to one or more of the embodiments described herein and made by a process as provided herein.

According to a seventh aspect of the present invention is provided Anhydrous Aripiprazole Crystals B formulated with one or more pharmaceutically acceptable carriers.

Other embodiments of the present invention may comprise suitable combinations of two or more of the embodiments and/or aspects disclosed herein.

Yet other embodiments and aspects of the invention will be apparent according to the description provided below.

Yet another aspect of the present invention comprised discovering that when aripiprazole hydrate (Conventional Hydrate as defined herein) is milled, it converts to an aripiprazole hydrate (Hydrate A as defined herein) with a different powder x-ray diffraction spectrum by different peak intensities. Moreover, it was found that Hydrate A loses the sharp dehydration endothermic peak of 123.5° C. which characterizes unmilled Conventional Hydrate in thermogravimetric/differential thermal analysis. Thus, the Conventional Hydrate is transformed into Hydrate A after milling Conventional Hydrate and exhibits a gradual dehydration endothermic peak between about 60° C. and 120° C. with a weak peak at about 71° C.

Yet another aspect of the invention comprised discovering that when heated to a specific temperature of 90-125° C. for 3-50 hr, this novel aripiprazole hydrate dehydrates gradually avoiding the aggregation phenomenon thought to be caused in conventional aripiprazole hydrate by rapid dehydration, and that anhydrous aripiprazole crystals obtained by heating of the novel aripiprazole hydrate to a specific temperature are anhydrous aripiprazole crystals with the desired properties.

Characterization of Hydrate A

Particles of "Hydrate A" as used herein have the physicochemical properties given in (1)-(5) below:

(1) It has an endothermic curve which is substantially the same as the thermogravimetric/differential thermal analysis (heating rate 5° C./min) endothermic curve shown in FIG. 1. Specifically, it is characterized by the appearance of a small peak at about 71° C. and a gradual endothermic peak around 60° C. to 120° C.

(2) It has an $^1$H-NMR spectrum which is substantially the same as the $^1$H-NMR spectrum (DMSO-$d_6$, TMS) shown in FIG. 2. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.1.7 ppm (m, 1H), 7.28-7.32 ppm (m, 2H) and 10.00 ppm (s, 1H).

(3) It has a powder z-ray diffraction spectrum which is substantially the same as the powder x-ray diffraction spectrum shown in FIG. 3. Specifically, it has characteristic peaks at 2θ=12.6°, 15.4°, 17.3°, 18.0°, 18.6°, 22.5° and 24.8°.

(4) It has clear infrared absorption bands at 2951, 2822, 1692, 1577, 1447, 1378, 1187, 963 and 784 cm$^{-1}$, on the IR (KBr) spectrum.

(5) It has a mean particle size of 50 nm or less.

Process for Manufacturing Hydrate A

Hydrate A is manufactured by milling Conventional Hydrate. Conventional milling methods can be used to mill Conventional Hydrate. For example, Conventional Hydrate can be milled in a milling machine. A widely used milling machine can be used, such as an atomizer, pin mill, jet mill or ball mill. Of these, the atomizer is preferred.

Regarding the specific milling conditions when using an atomizer, a rotational speed of 5000-15000 rpm could be used for the main axis, for example, with a feed rotation of 10-30 rpm and a screen hole size of 1-5 mm.

The mean particle size of the Aripiprazole Hydrate A obtained by milling should normally be 50 μm or less, preferably 30 μm or less. Mean particle size can be ascertained by the particle size measurement method described hereinafter.

Characterization of Anhydrous Aripiprazole Crystals B

"Anhydrous Aripiprazole Crystals B" of the present invention as used herein have the physicochemical properties given in (6)-(12) below.

(6) They have an $^1$H-NMR spectrum which is substantially the same as the $^1$H-NMR spectrum (DMSO-$d_6$, TMS) shown in FIG. 4. Specifically, they have characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

(7) They have a powder x-ray diffraction spectrum which is substantially the same as the powder x-ray diffraction spectrum shown in FIG. 5. Specifically, they have characteristic peaks at 2θ=11.0°, 16.6°, 19.3°, 20.3° and 22.1°.

(8) They have clear infrared absorption bands at 2945, 2812, 1678, 1627, 1448, 1377, 1173, 960 and 779 cm$^{-1}$ on the IR (KBr) spectrum.

(9) They exhibit an endothermic peak near about 141.5° C. in thermogravimetric/differential thermal analysis (heating rate 5° C./min).

(10) They exhibit an endothermic peak near about 140.7° C. in differential scanning calorimetry (heating rate 5° C./min).

(11) Anhydrous Aripiprazole Crystals B of the present invention have low hygroscopicity. For example, Anhydrous Aripiprazole Crystals B of the present invention maintain a water content of 0.4% or less after 24 hours inside a dessicator set at a temperature of 60° C. and a humidity of 100%. Well-known methods of measuring water content can be used as long as they are methods commonly used for measuring the water content of crystals. For example, a method such as the Karl Fischer method can be used.

(12) When the small particle size is required for the formulation such as tablet and other solid dose formulations including for example flashmelt formulations, the mean particle size is preferably 50 μm or less.

Process for Manufacturing Anhydrous Aripiprazole Crystals B

In case of the formulation for which small particle size (less than 50 μm) is required, the milling is necessary for the preparation. However, when a large amount of Conventional Anhydrous Aripiprazole or Anhydrous Aripiprazole Crystals B having large particle size is milled, the milled substances adhere with each other in the milling machine. Accordingly, there is a disadvantage that it is difficult to industrially prepare Anhydrous Aripiprazole Crystals B having small particle size.

Under the circumstances, the inventors of the present invention have found that Conventional hydrate can be easily milled, and Anhydrous Aripiprazole Crystals B having small particle size can be obtained in high yield with good-operability by heating the milled hydrate A thus obtained.

The Anhydrous Aripiprazole Crystals B of the present invention are prepared for example by heating the aforementioned Aripiprazole Hydrate A at 90-125° C. The heating time is generally about 3-50 hours, but cannot be stated unconditionally since it differs depending on heating temperature. The heating time and heating temperature are inversely related, so that for example the heating time will be longer the lower the heating temperature, and shorter the higher the heating temperature. Specifically, if the heating temperature of Aripiprazole Hydrate A is 100° C., the heating time should normally be 18 hours or more or preferably about 24 hours. If the heating temperature of Aripiprazole Hydrate A is 120° C., on the other hand, the heating time can be about 3 hours. The Anhydrous Aripiprazole Crystals B of the present invention can be prepared with certainty by heating Aripiprazole Hydrate A for about 1.8 hours at 100° C., and then heating it for about 3 hours at 120° C. The Anhydrous Aripiprazole Crystals B of the present invention can also be obtained if the heating time is extended still further, but this may not be economical.

When small particle size is not required for the formulation, e.g., when drug substance is being manufactured for injectable or oral solution formulations, Anhydrous Aripiprazole Crystal B can be also obtained the following process.

The inventors also discovered that it is possible to obtain anhydrous aripiprazole crystals by heating conventional aripiprazole hydrate or conventional anhydrous aripiprazole crystals to a specific temperature but this process does not yield Anhydrous Aripiprazole Crystal B crystalline substance suitable for commercial use in the formulation of solid oral dose formulations.

Furthermore, the Anhydrous Aripiprazole Crystals 8 of the present invention are prepared for example by heating conventional anhydrous aripiprazole crystals at 90-125° C. The heating time is generally about 3-50 hours, but cannot be stated unconditionally since it differs depending on heating temperature. The heating time and heating temperature are inversely related, so that for example the heating time will be longer the lower the heating temperature, and shorter the higher the heating temperature.

Specifically, if the heating temperature of the anhydrous aripiprazole crystals is 100° C., the heating time can be about 4 hours, and if the heating temperature is 120° C. the heating time can be about 3 hours.

In addition to Aripiprazole Hydrate A and Anhydrous Aripiprazole Crystals B mentioned above, the present invention provides Anhydrous Aripiprazole Crystals C to G as follows.

Figure 8:
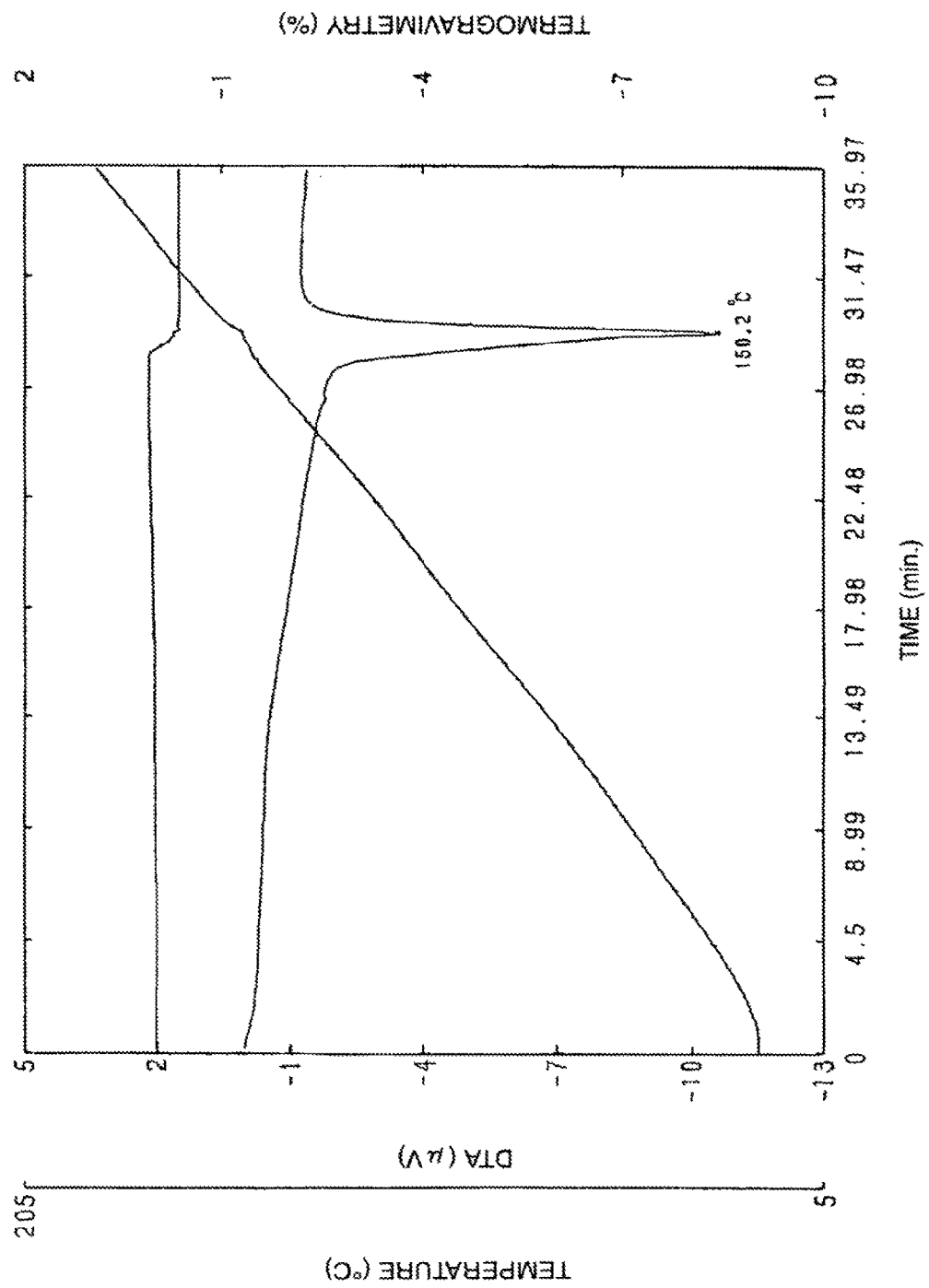
FIG. 8 shows thermogravimetric/differential thermal analysis endothermic curve of the type C crystals of anhydrous aripiprazole obtained in Example 11.
Figure 9:
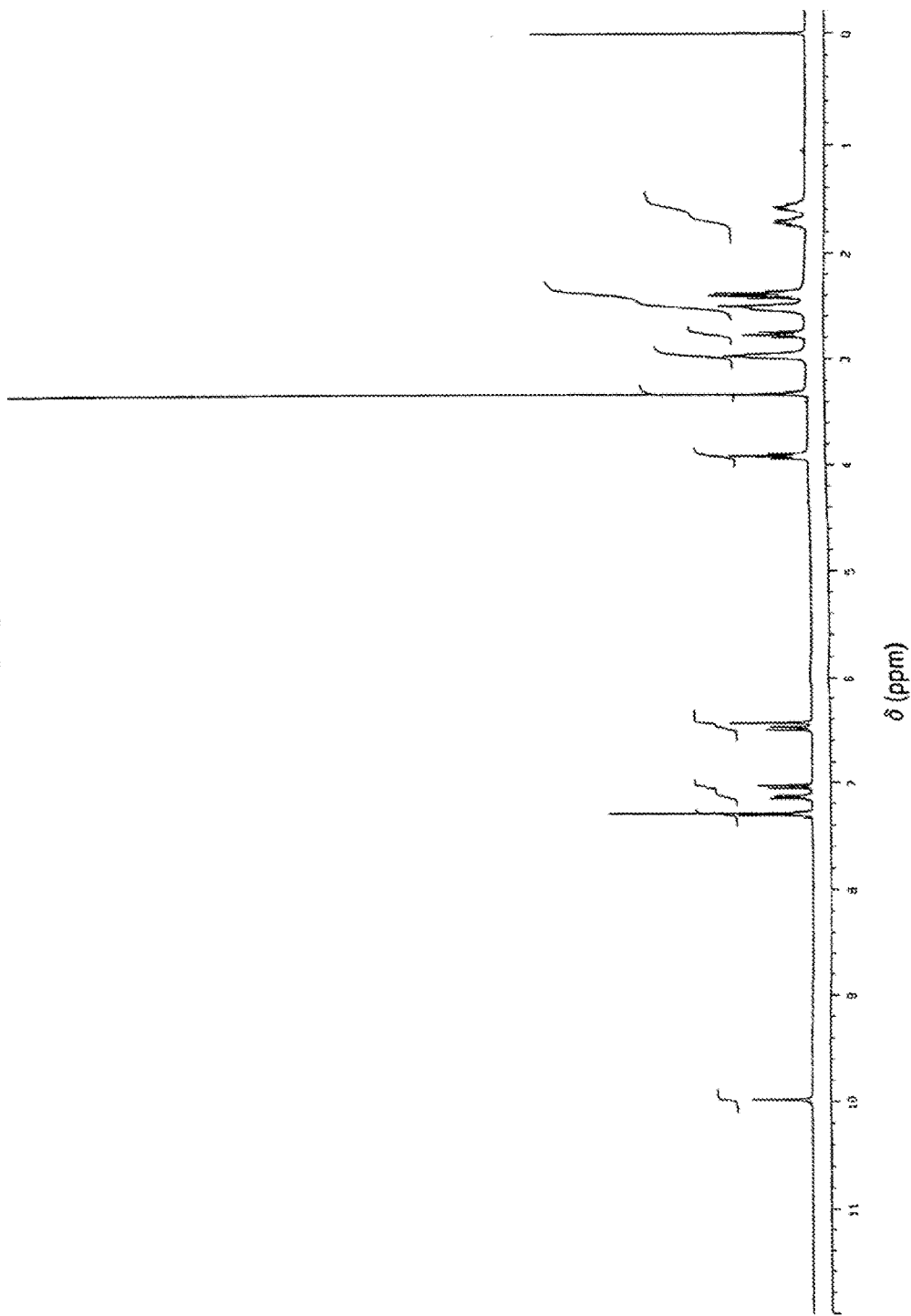
FIG. 9 shows an $^1$H-NMR spectrum (DMSO-$d_6$, TMS) of the type C crystals of anhydrous aripiprazole obtained in Example 11.
Figure 10:
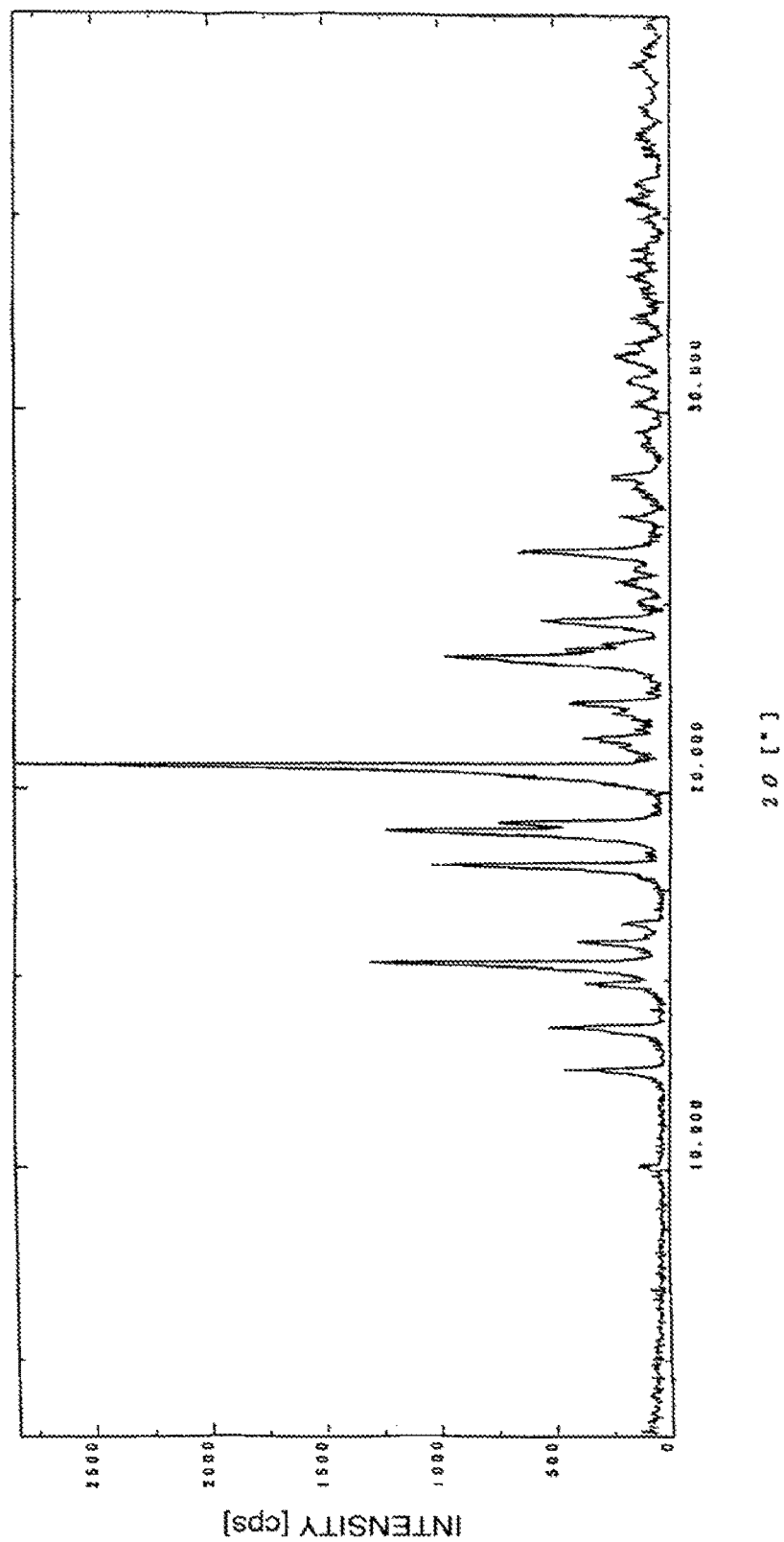
FIG. 10 shows a powder X-ray diffraction spectrum of the type C crystals of anhydrous aripiprazole obtained in Example 11.
Figure 11:
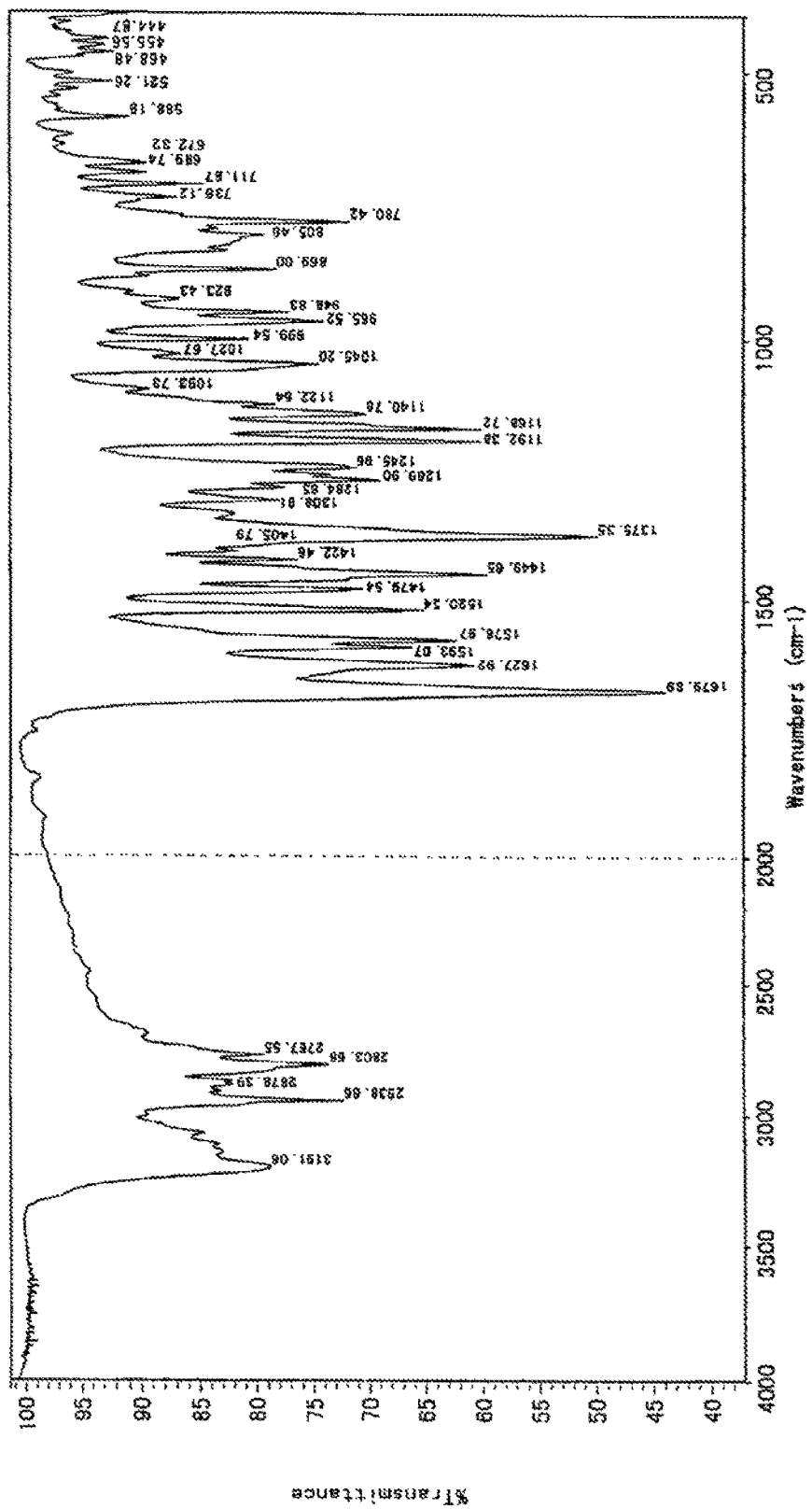
FIG. 11 shows an IR spectrum of the type C crystals of anhydrous aripiprazole obtained in Example 11.
Figure 12:
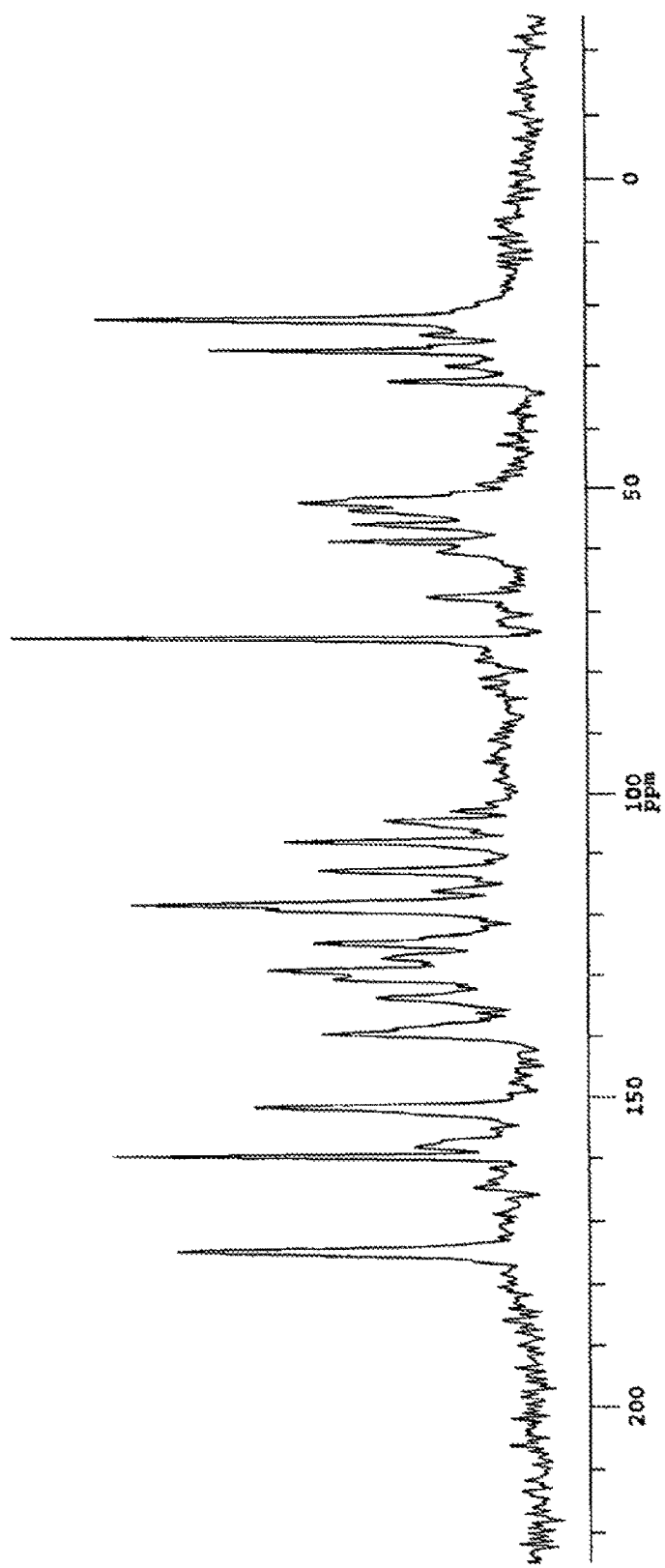
FIG. 12 shows a solid $^{13}$C-NMR spectrum of the type C crystals of anhydrous aripiprazole obtained in Example 11.

1. The present invention relates to anhydrous aripiprazole crystals (hereinafter referred to as "type C crystals of anhydrous aripiprazole") having the following physicochemical properties (1) to (5):

(1) an endothermic curve which is substantially identical to the thermogravimetric/differential thermal analysis (heating rate: 5° C./min.) endothermic curve shown in FIG. 8;

(2) an $^1$H-NMR spectrum which is substantially identical to the $^1$H-NMR spectrum (DMSO-di, TMS) shown in FIG. 9;

(3) a powder X-ray diffraction spectrum which is substantially identical to the powder X-ray diffraction spectrum shown in FIG. 10;

(4) an IR spectrum which is substantially identical to the IR (KBr) shown in FIG. 11; and (5) a solid $^{13}$C-NMR spectrum which is substantially identical to the solid $^{13}$C-NMR spectrum shown in FIG. 12.

Figure 13:
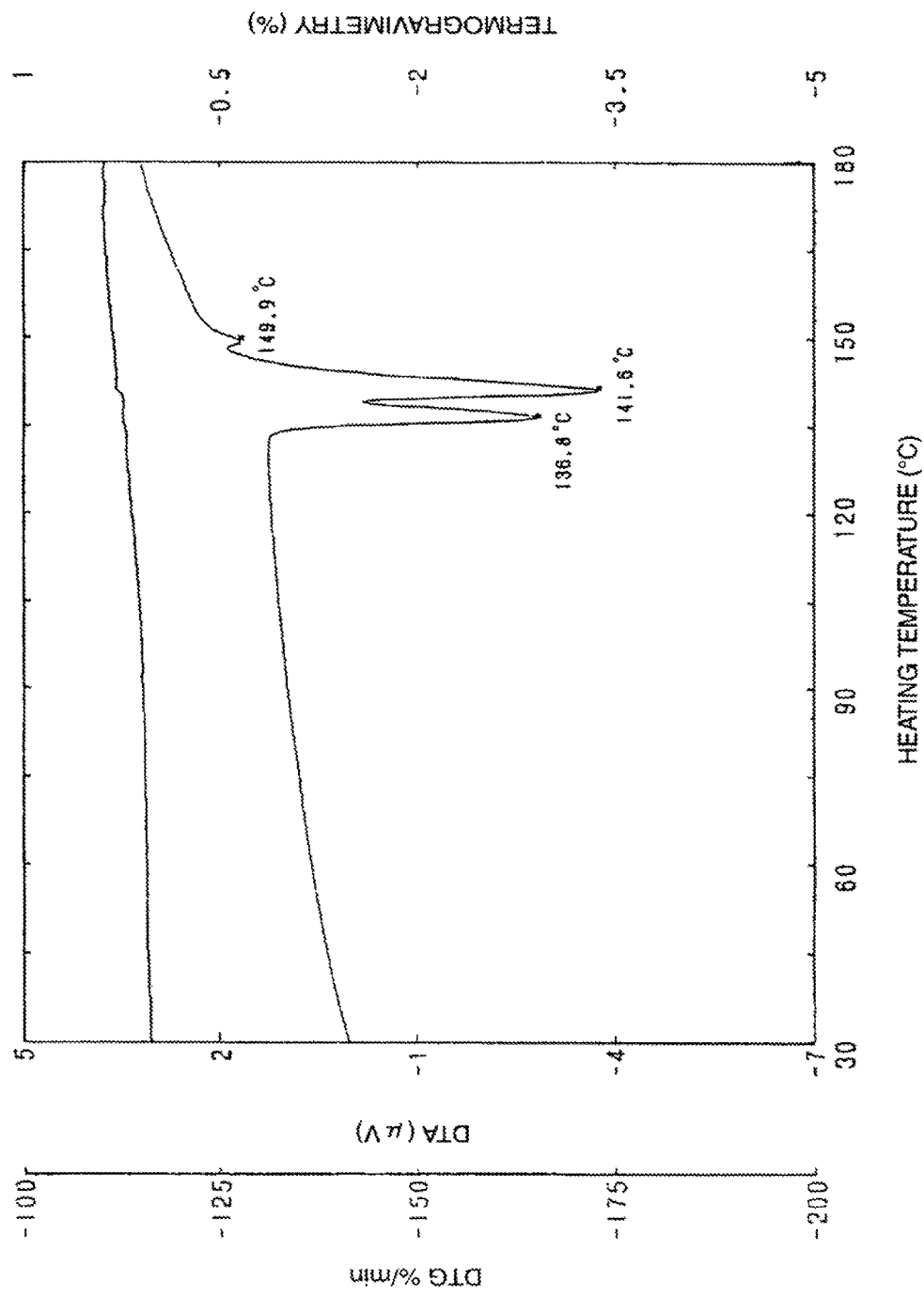
FIG. 13 shows a thermogravimetric/differential thermal analysis endothermic curve of the type D crystals of anhydrous aripiprazole obtained in Example 12 or Example 13.
Figure 14:
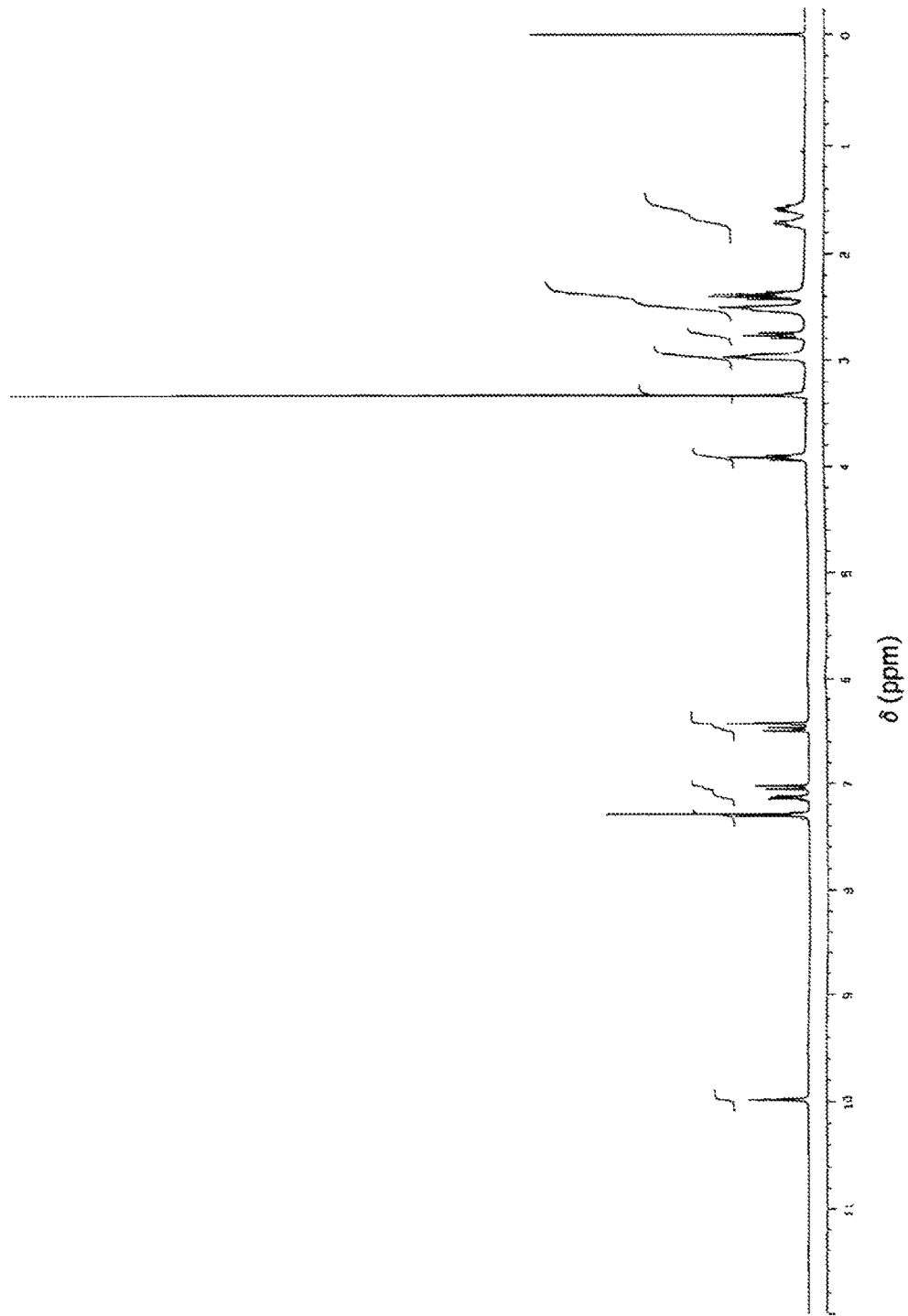
FIG. 14 shows an $^1$H-NMR spectrum (DMSO-$d_6$, TMS) of the type D crystals of anhydrous aripiprazole obtained in Example 12 or Example 13.
Figure 15:
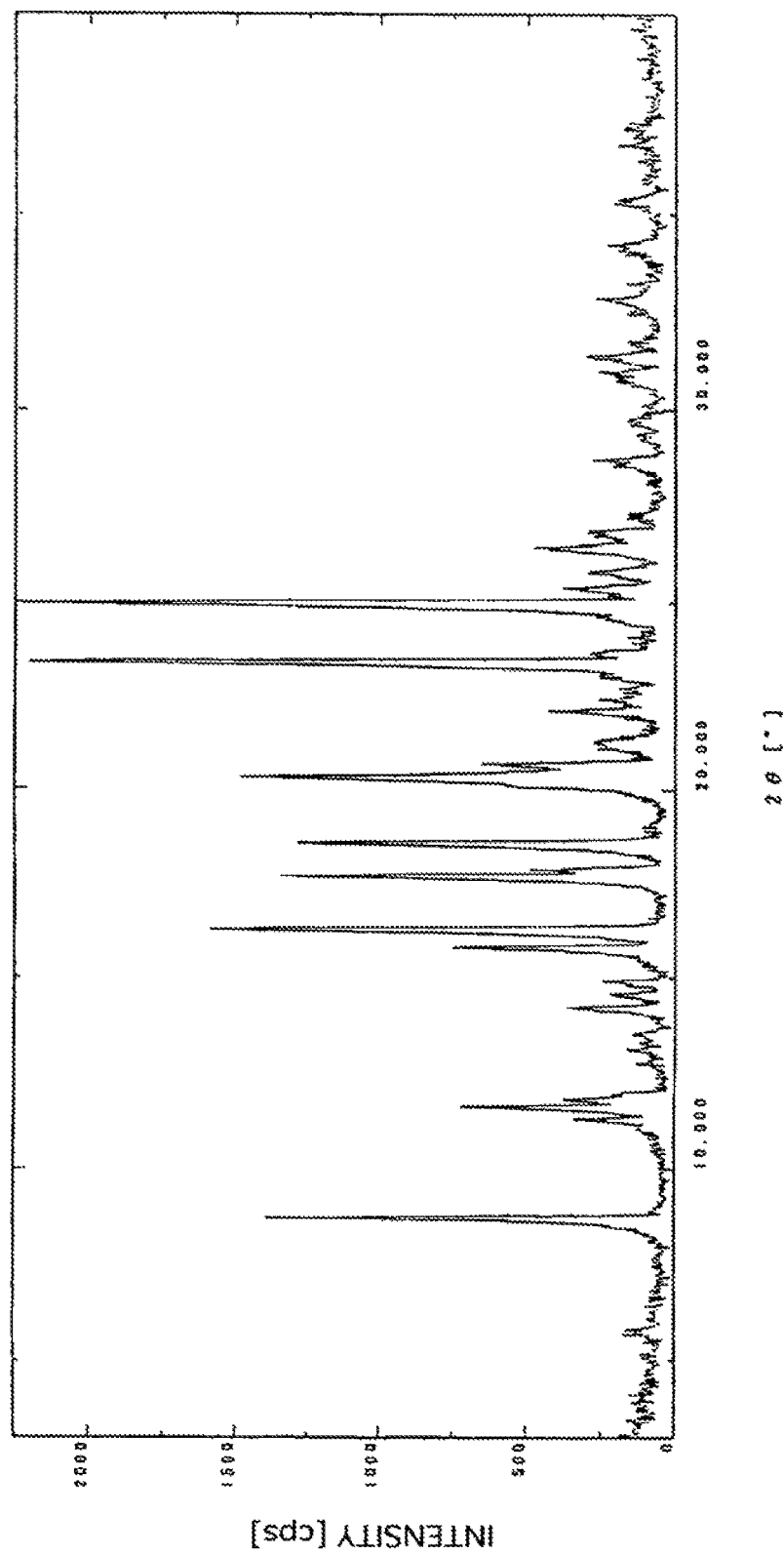
FIG. 15 shows a powder X-ray diffraction spectrum of the type D crystals of anhydrous aripiprazole obtained in Example 12 or Example 13.
Figure 16:
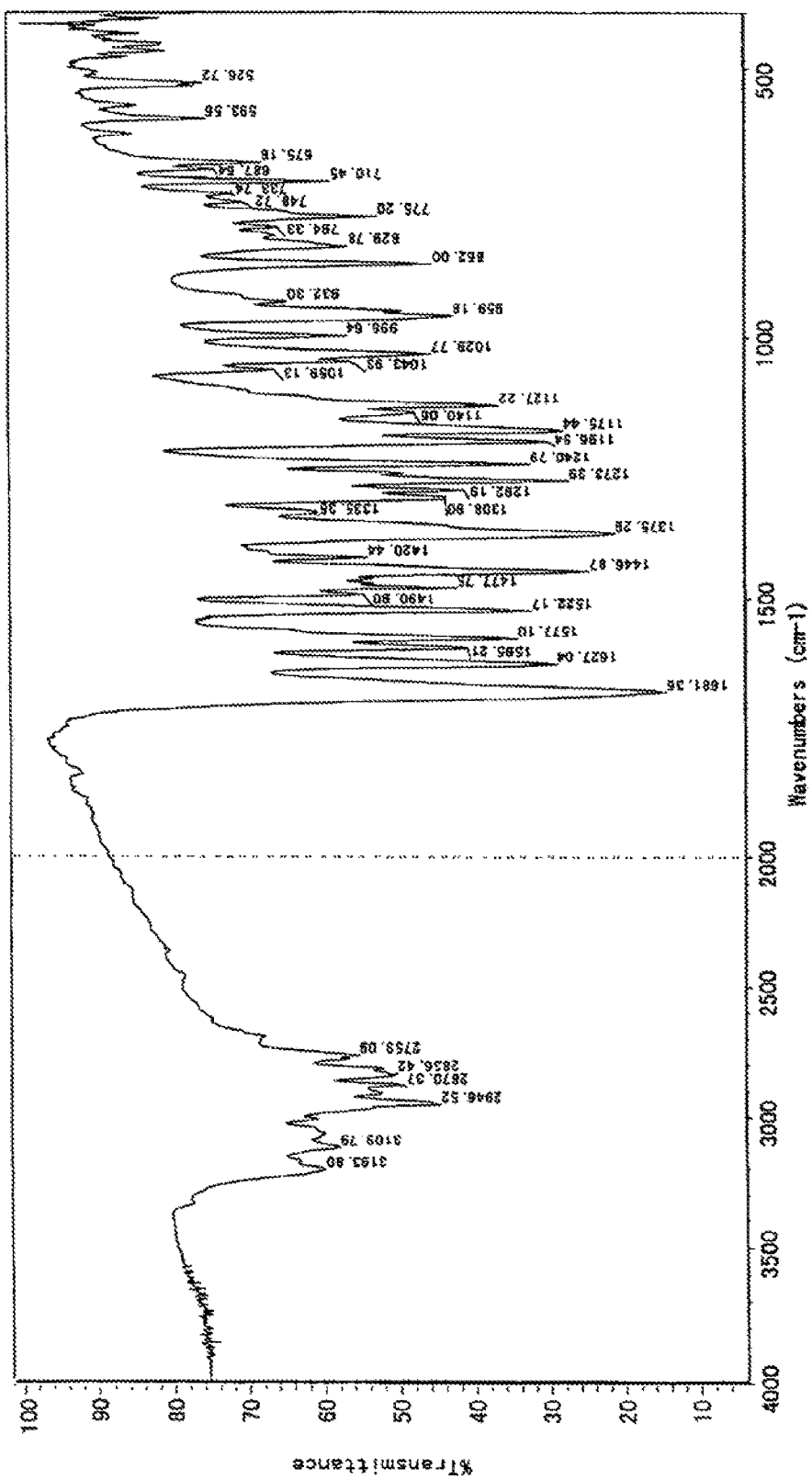
FIG. 16 shows an IR spectrum of the type D crystals of anhydrous aripiprazole obtained in Example 12 or Example 13.

2. The present invention relates to anhydrous aripiprazole crystals (hereinafter referred to as "type D crystals of anhydrous aripiprazole") having the following physicochemical properties (6) to (10):

(6) an endothermic curve which is substantially identical to the thermogravimetric/differential thermal analysis (heating rate: 5° C./min.) endothermic curve shown in FIG. 13;

(7) an $^1$H-NMR spectrum which is substantially identical to the $^1$H-NMR spectrum (DMSO-$d_6$, TMS) shown in FIG. 14;

(8) a powder X-ray diffraction spectrum which is substantially identical to the powder X-ray diffraction spectrum shown in FIG. 15;

(9) an IR spectrum which is substantially identical to the IR (KBr) shown in FIG. 16; and

Figure 17:
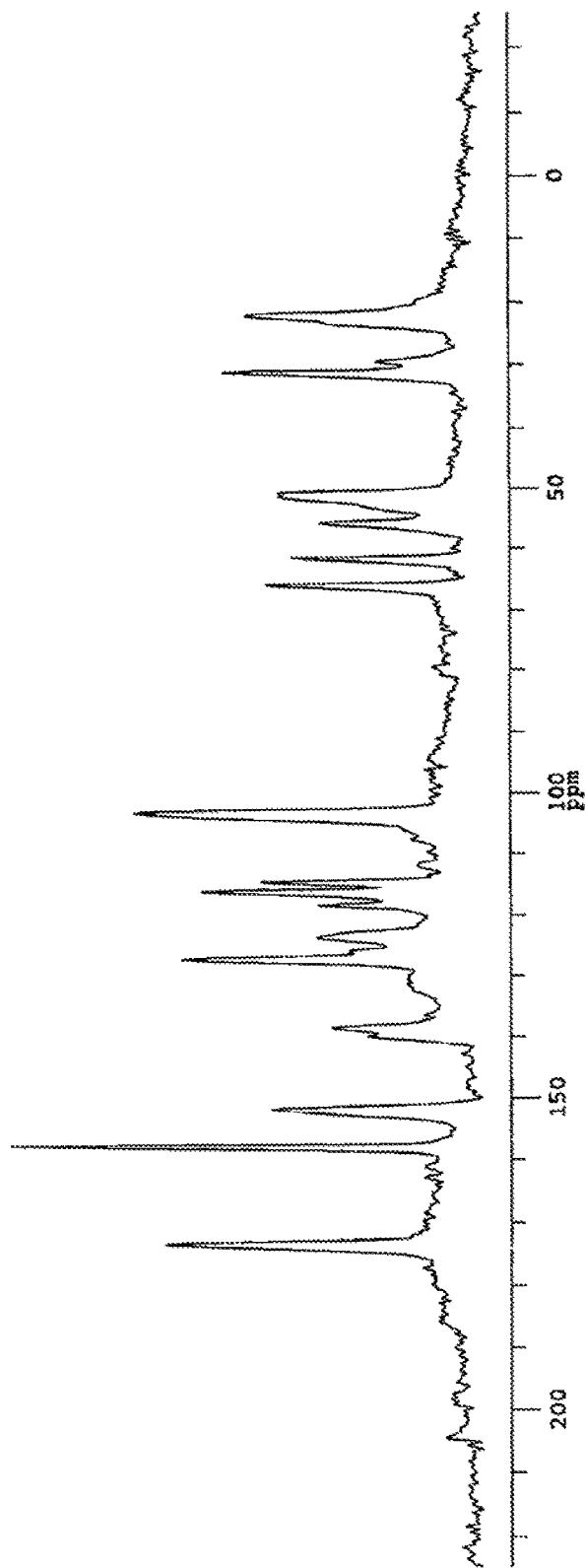
FIG. 17 shows a solid $^{13}$C-NMR spectrum of the type D crystals of anhydrous aripiprazole obtained in Example 12 or Example 13.

(10) a solid $^{13}$C-NMR spectrum which is substantially identical to the $^{13}$C-NMR spectrum shown in FIG. 17.

Figure 18:
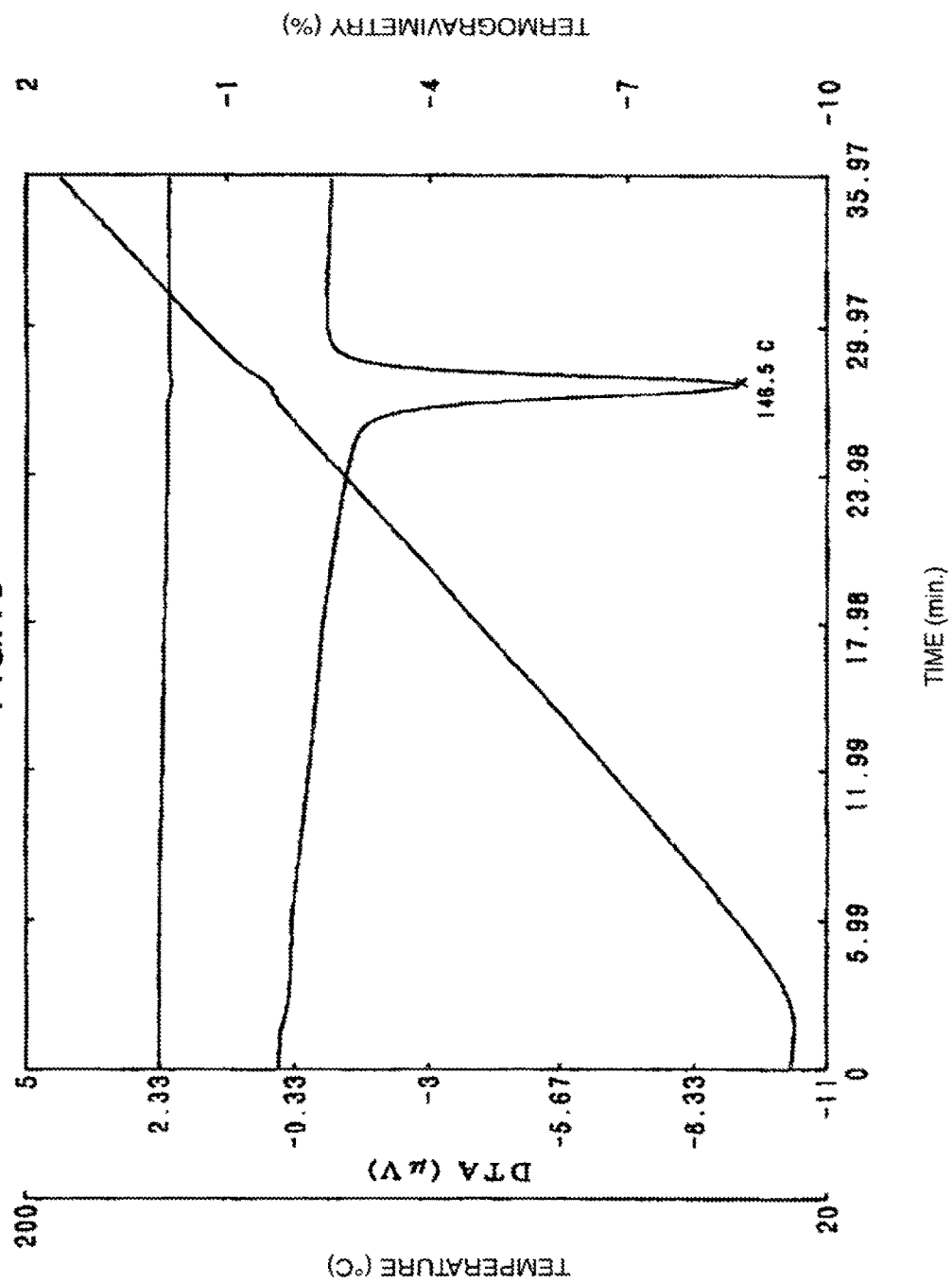
FIG. 18 shows a thermogravimetric/differential thermal analysis endothermic curve of the type E crystals of anhydrous aripiprazole obtained in Example 14.
Figure 19:
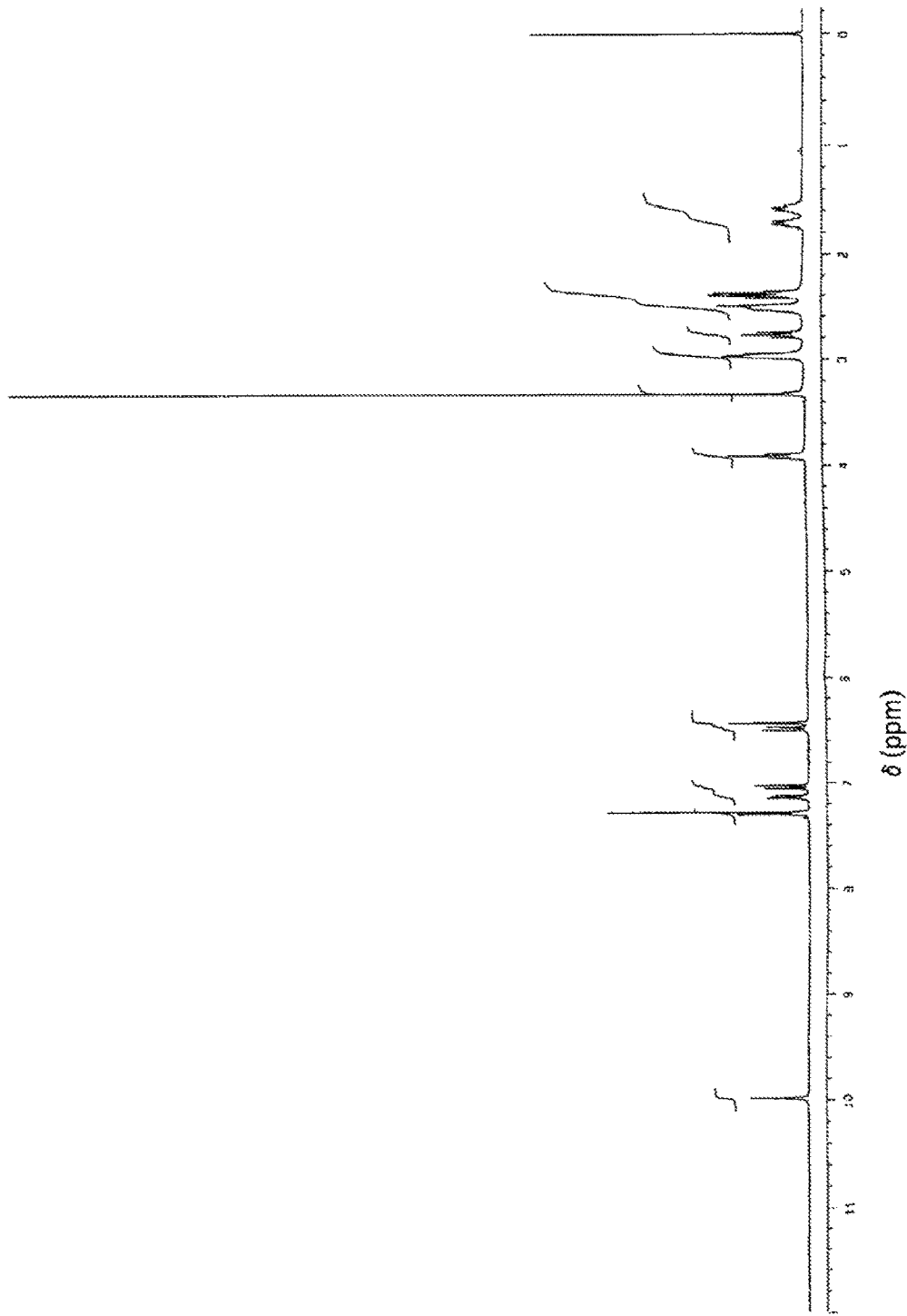
FIG. 19 shows an $^1$H-NMR spectrum (DMSO-$d_6$, TMS) of the type E crystals of anhydrous aripiprazole obtained in Example 14.
Figure 20:
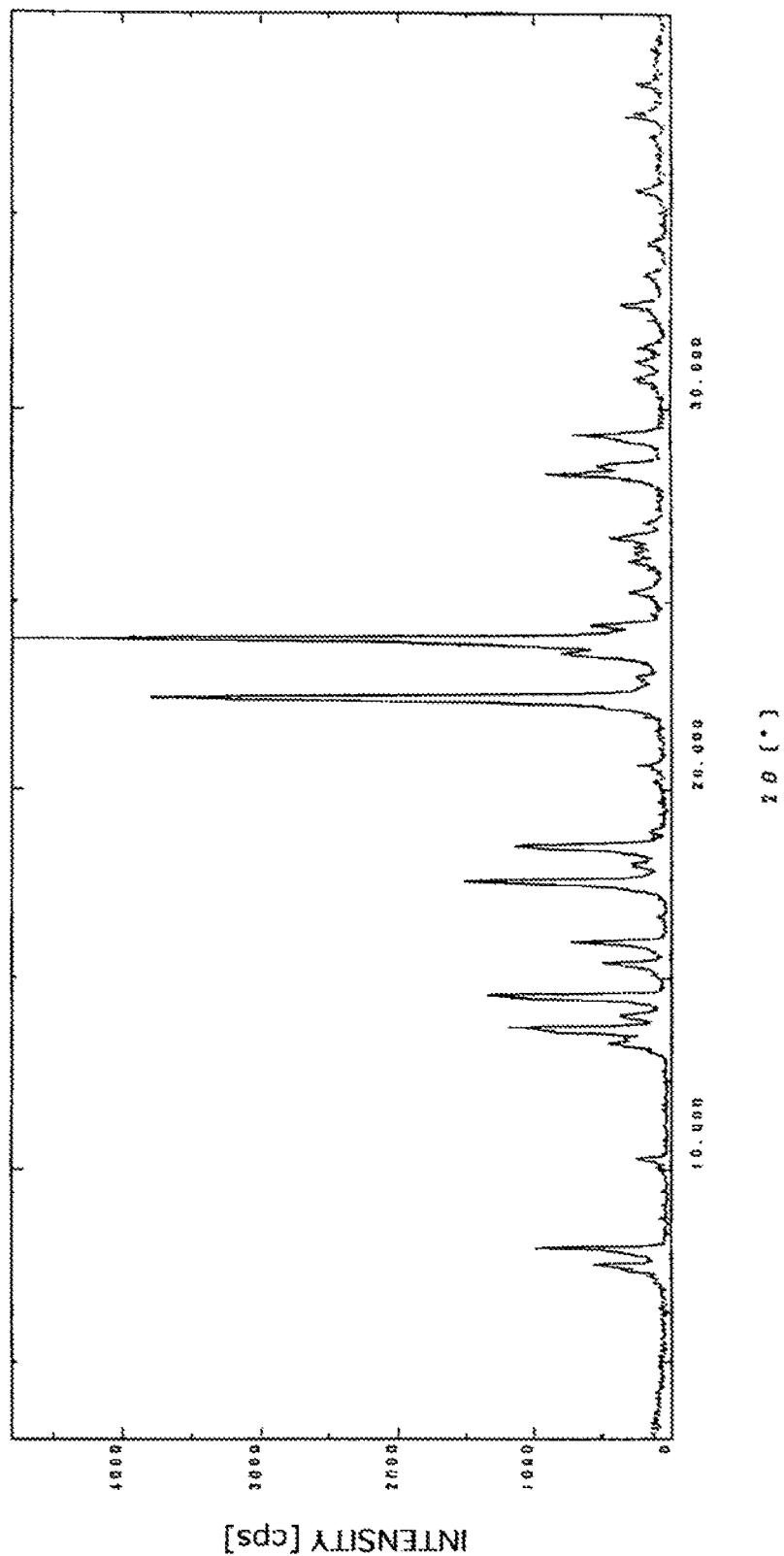
FIG. 20 shows a powder X-ray diffraction spectrum of the type E crystals of anhydrous aripiprazole obtained in Example 14.

3. The present invention relates to anhydrous aripiprazole crystals (hereinafter referred to as "type E crystals of anhydrous aripiprazole") having the following physicochemical properties (11) to (14):

(11) an endothermic curve which is substantially identical to the thermogravimetric/differential thermal analysis (heating rate: 5° C./min.) endothermic curve shown in FIG. 18;

(12) an $^1$H-NMR spectrum which is substantially identical to the $^1$H-NMR spectrum (DMSO-$d_6$, TMS) shown in FIG. 19;

(13) a powder X-ray diffraction spectrum which is substantially identical to the powder X-ray diffraction spectrum shown in FIG. 20; and

Figure 21:
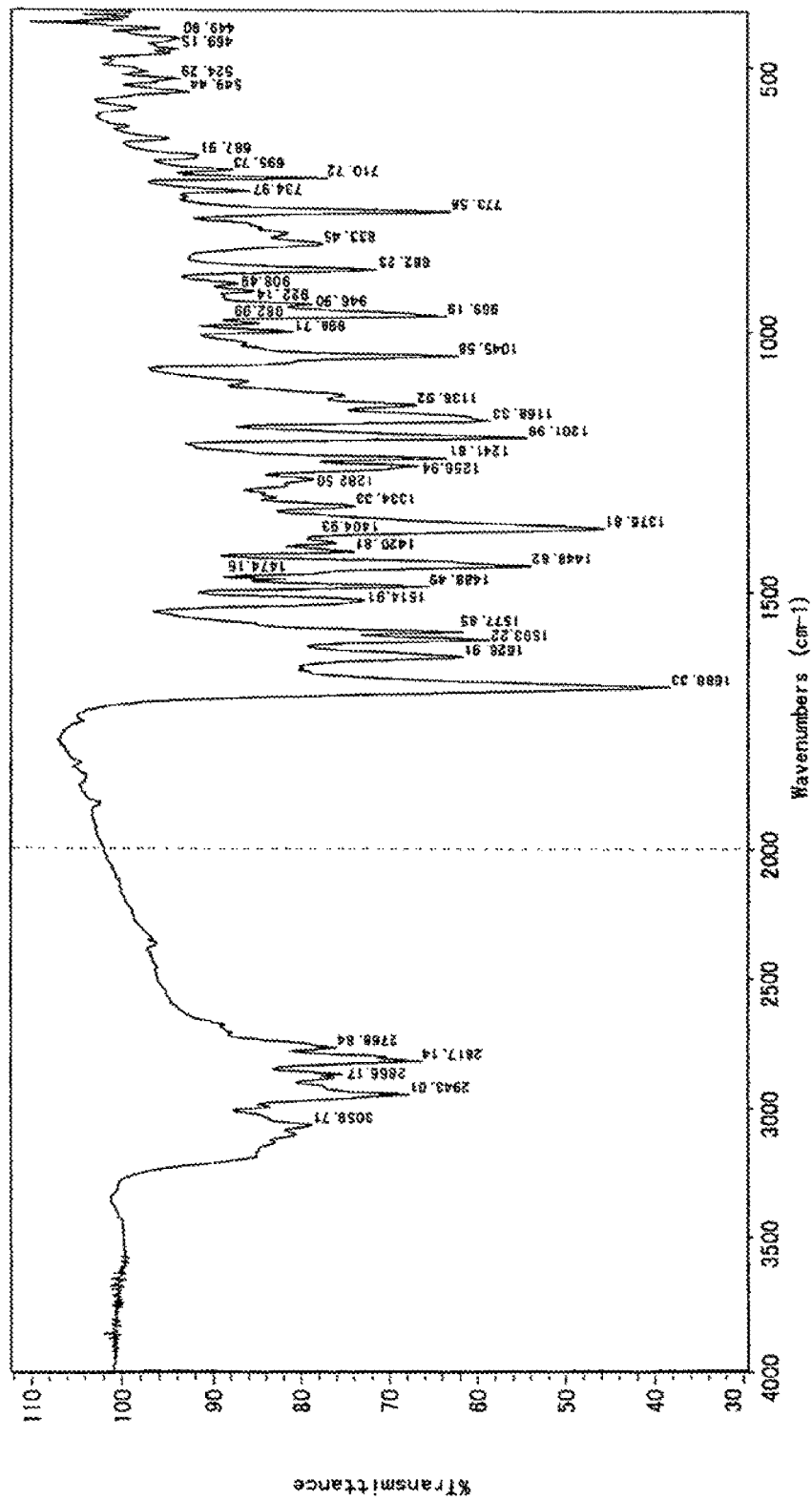
FIG. 21 shows an IR spectrum of the type E crystals of anhydrous aripiprazole obtained in Example 14.

(14) an IR spectrum which is substantially identical to the IR (KBr) shown in FIG. 21.

Figure 22:
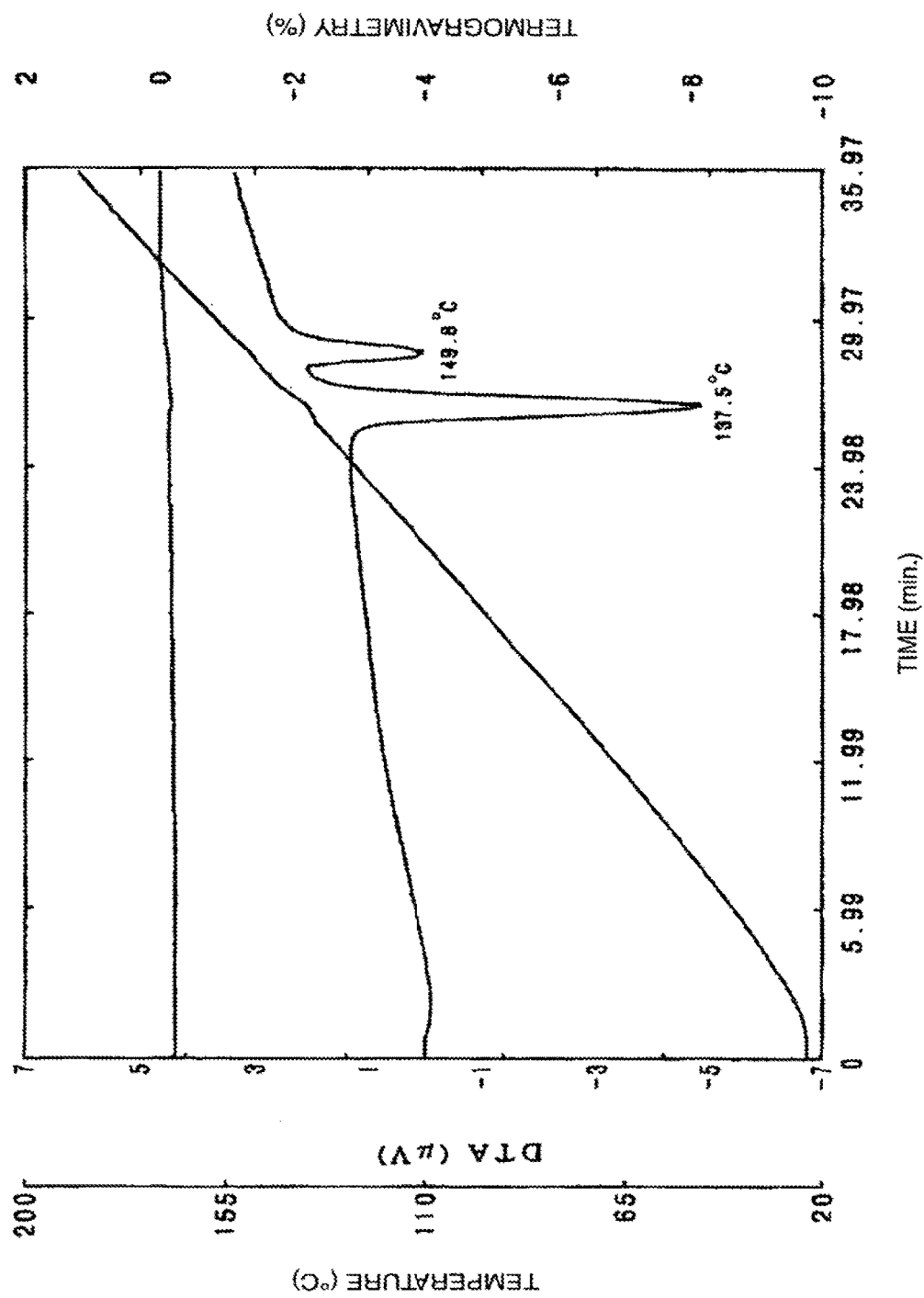
FIG. 22 shows a thermogravimetric/differential thermal analysis endothermic curve of the type F crystals of anhydrous aripiprazole obtained in Example 15.
Figure 23:
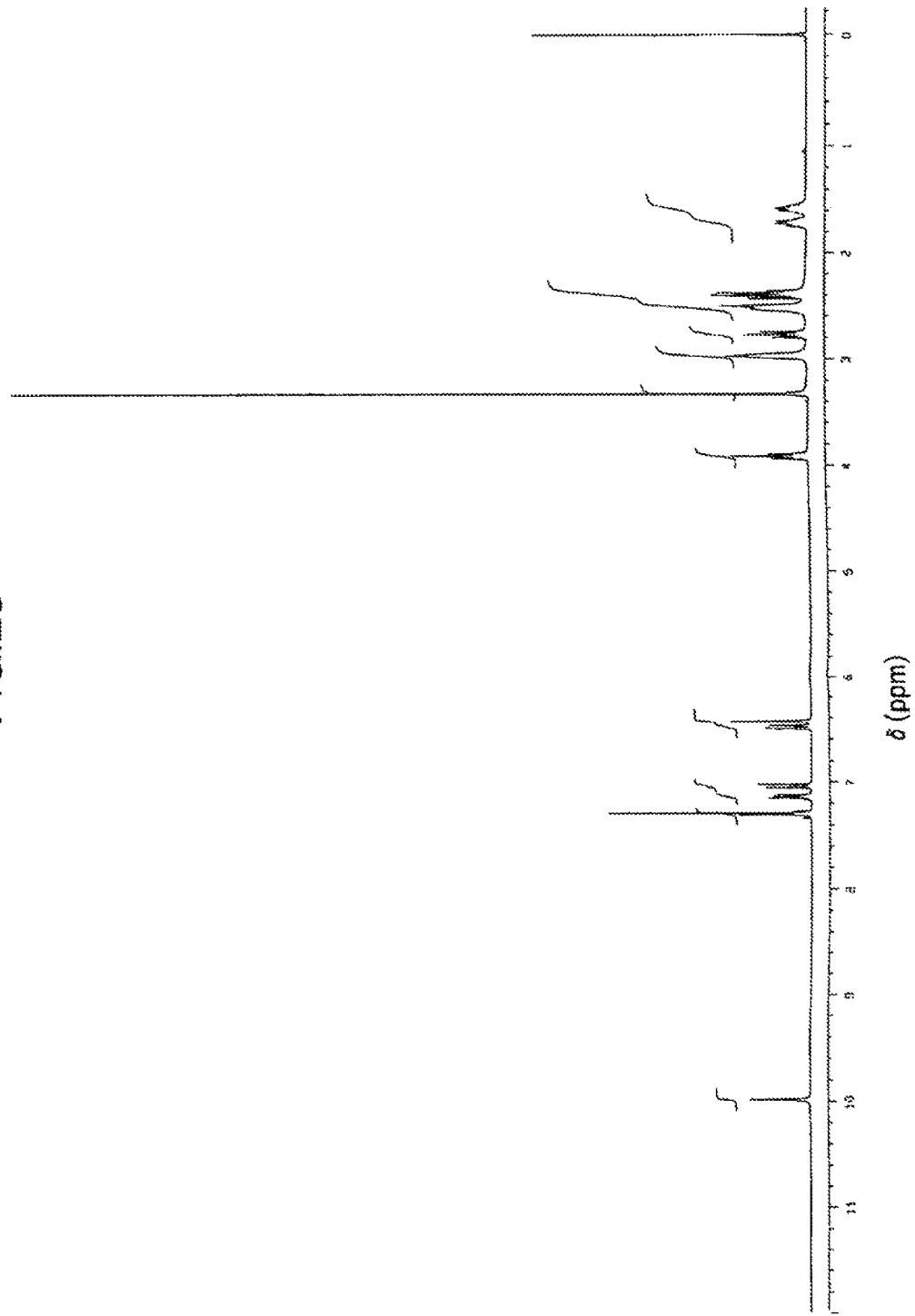
FIG. 23 shows an $^1$H-NMR spectrum (DMSO-$d_6$, TMS) of the type F crystals of anhydrous aripiprazole obtained in Example 15.
Figure 24:
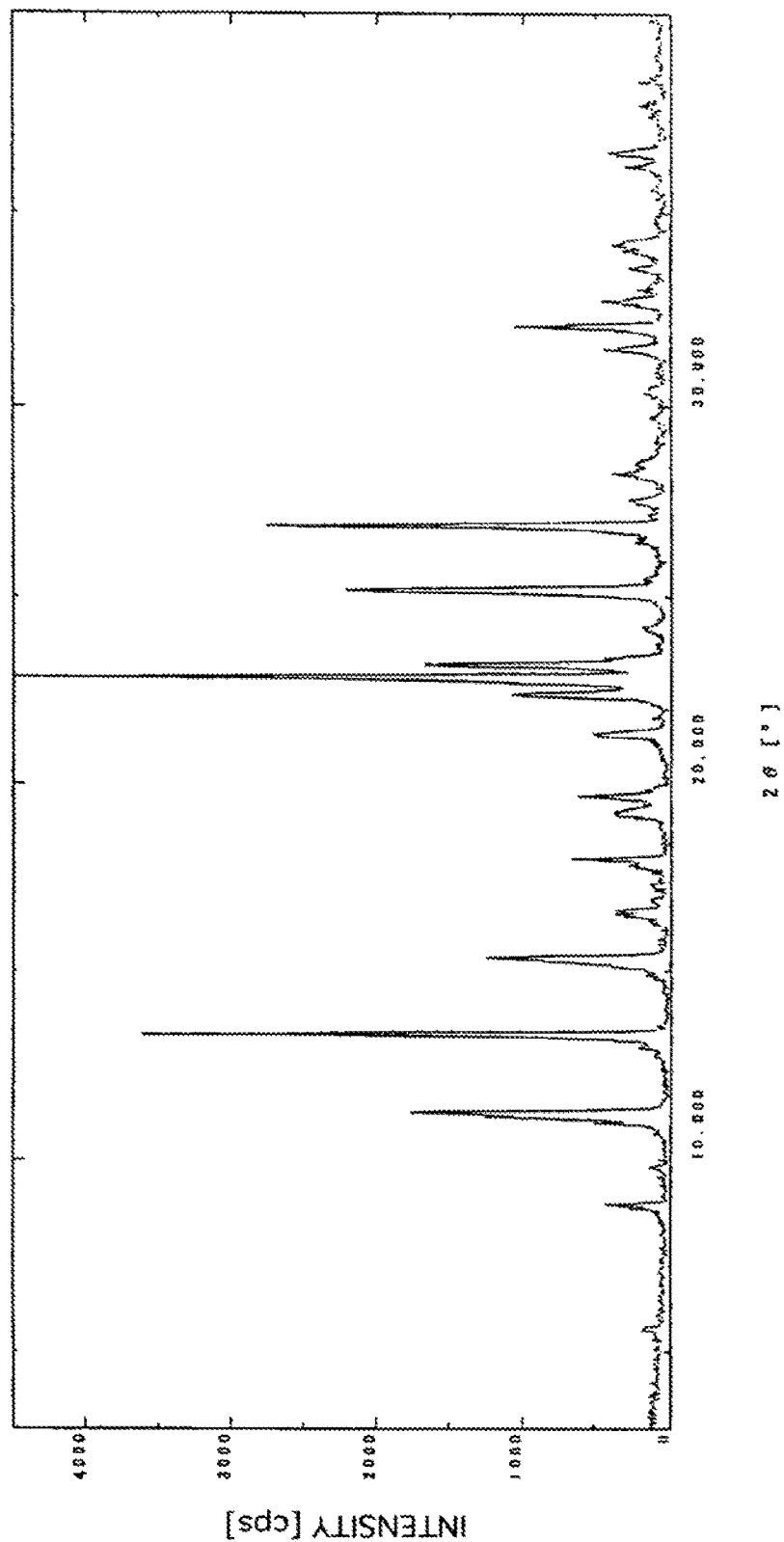
FIG. 24 shows a powder X-ray diffraction spectrum of the type F crystals of anhydrous aripiprazole obtained in Example 15.

4. The present invention relates to anhydrous aripiprazole crystals (hereinafter referred to as "type F crystals of anhydrous aripiprazole") having the following physicochemical properties (15) to (18):

(15) an endothermic curve which is substantially identical to the thermogravimetric/differential thermal analysis (heating rate: 5° C./min.) endothermic curve shown in FIG. 22;

(16) an $^1$H-NMR spectrum which is substantially identical to the $^1$H-NMR spectrum (DMSO-$d_6$, TMS) shown in FIG. 23;

(17) a powder X-ray diffraction spectrum which is substantially identical to the powder X-ray diffraction spectrum shown in FIG. 24; and

Figure 25:
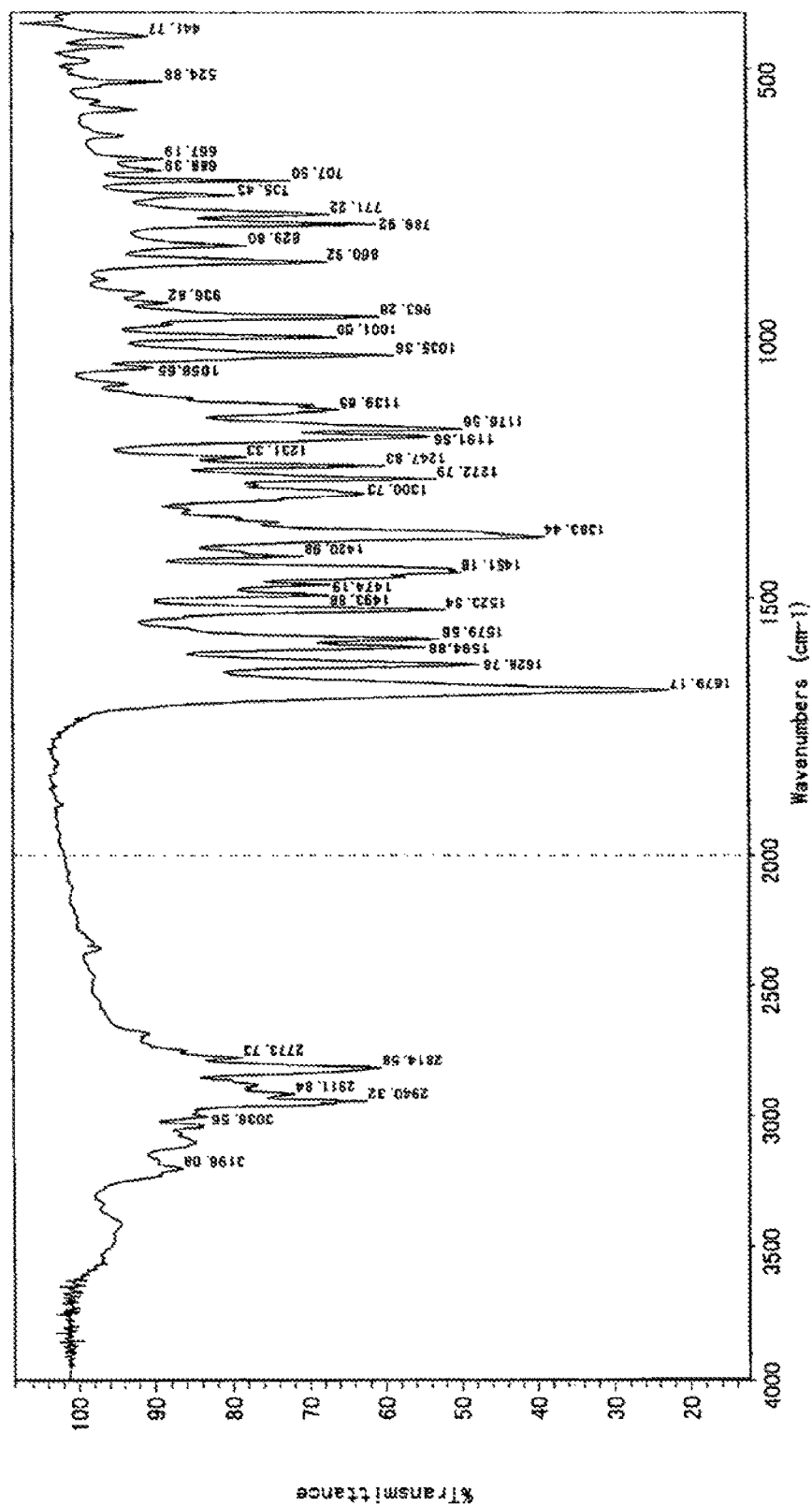
FIG. 25 shows an IR spectrum of the type F crystals of anhydrous aripiprazole obtained in Example 15.

(18) an IR spectrum which is substantially identical to the IR (KBr) shown in FIG. 25.

5. The present invention relates a process for preparing anhydrous aripiprazole crystals stated in the aforementioned item 1, characterized by heating anhydrous aripiprazole crystals at a temperature being higher than 140° C. and lower than 150° C.

6. The present invention relates a process for preparing anhydrous aripiprazole crystals stated in the aforementioned item 2, characterized by recrystallizing from toluene.

7. The present invention relates to a process for preparing anhydrous aripiprazole crystals stated in the aforementioned item 3, characterized by heating and dissolving anhydrous aripiprazole crystals in acetonitrile, and cooling it.

8. The present invention relates to a process for preparing anhydrous aripiprazole crystals stated in the aforementioned item 4, characterized by heating a suspension of anhydrous aripiprazole crystals in acetone.

9. The present invention relates to a pharmaceutical composition containing at least one anhydrous aripiprazole crystals selected from the group consisting of the anhydrous aripiprazole crystals stated in the aforementioned item 1, the anhydrous aripiprazole crystals stated in the aforementioned item 2, the anhydrous aripiprazole crystals stated in the aforementioned item 3, the anhydrous aripiprazole crystals stated in the aforementioned item 4, and the anhydrous aripiprazole crystals stated in the after-mentioned item 10, together with pharmaceutically acceptable carriers.

Figure 26:
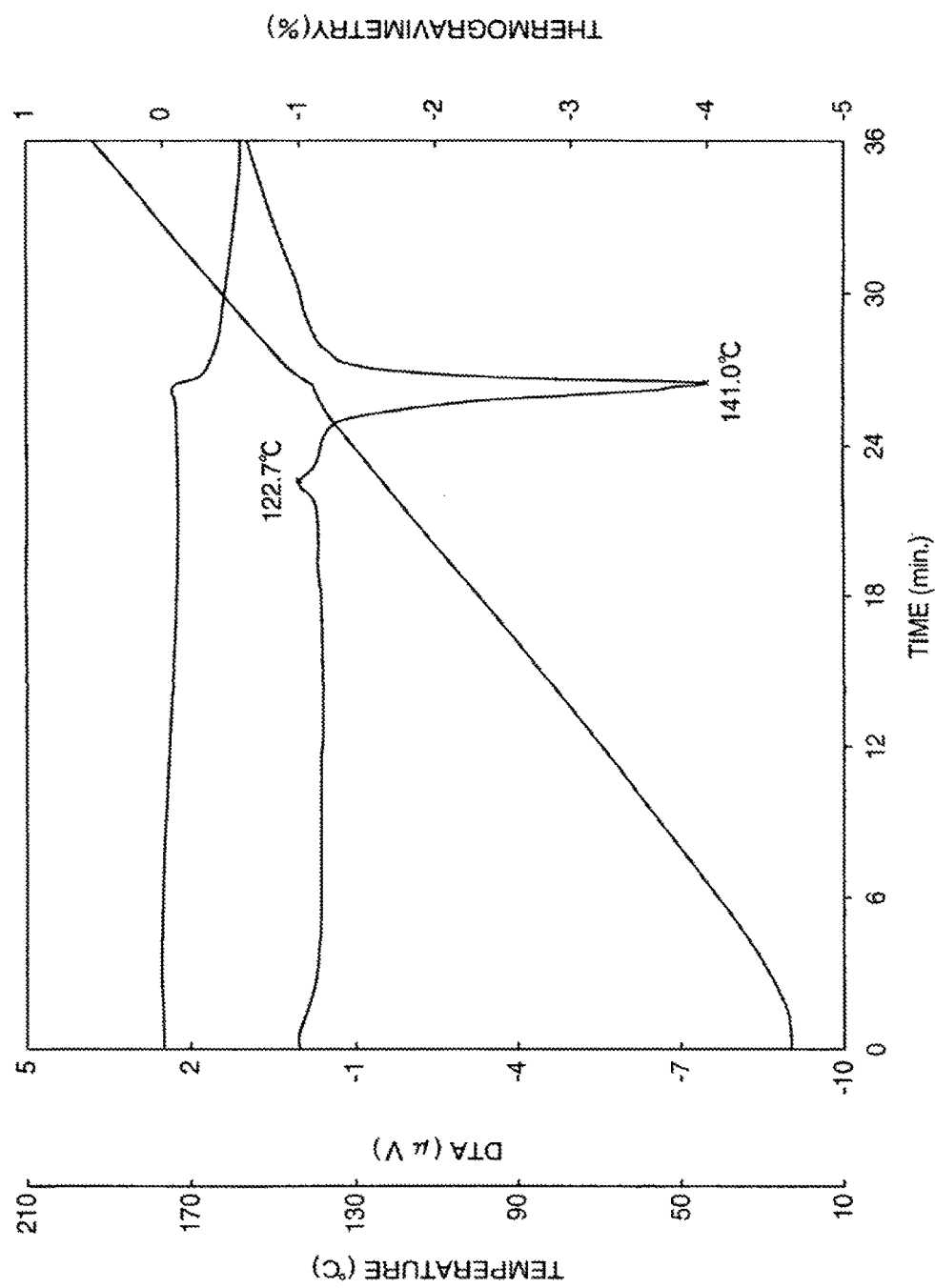
FIG. 26 shows thermogravimetric/differential thermal analysis endothermic curve of the type G crystals of anhydrous aripiprazole obtained in Example 16-b).

10. The present invention relates to anhydrous aripiprazole crystals (hereinafter referred to as "type G crystals of anhydrous aripiprazole") having the following physicochemical properties (19) to (22):

(19) an endothermic curve which is substantially identical to the thermogravimetric/differential thermal analysis (heating rate; 5° C./min.) endothermic curve shown FIG. 26.

Figure 27:
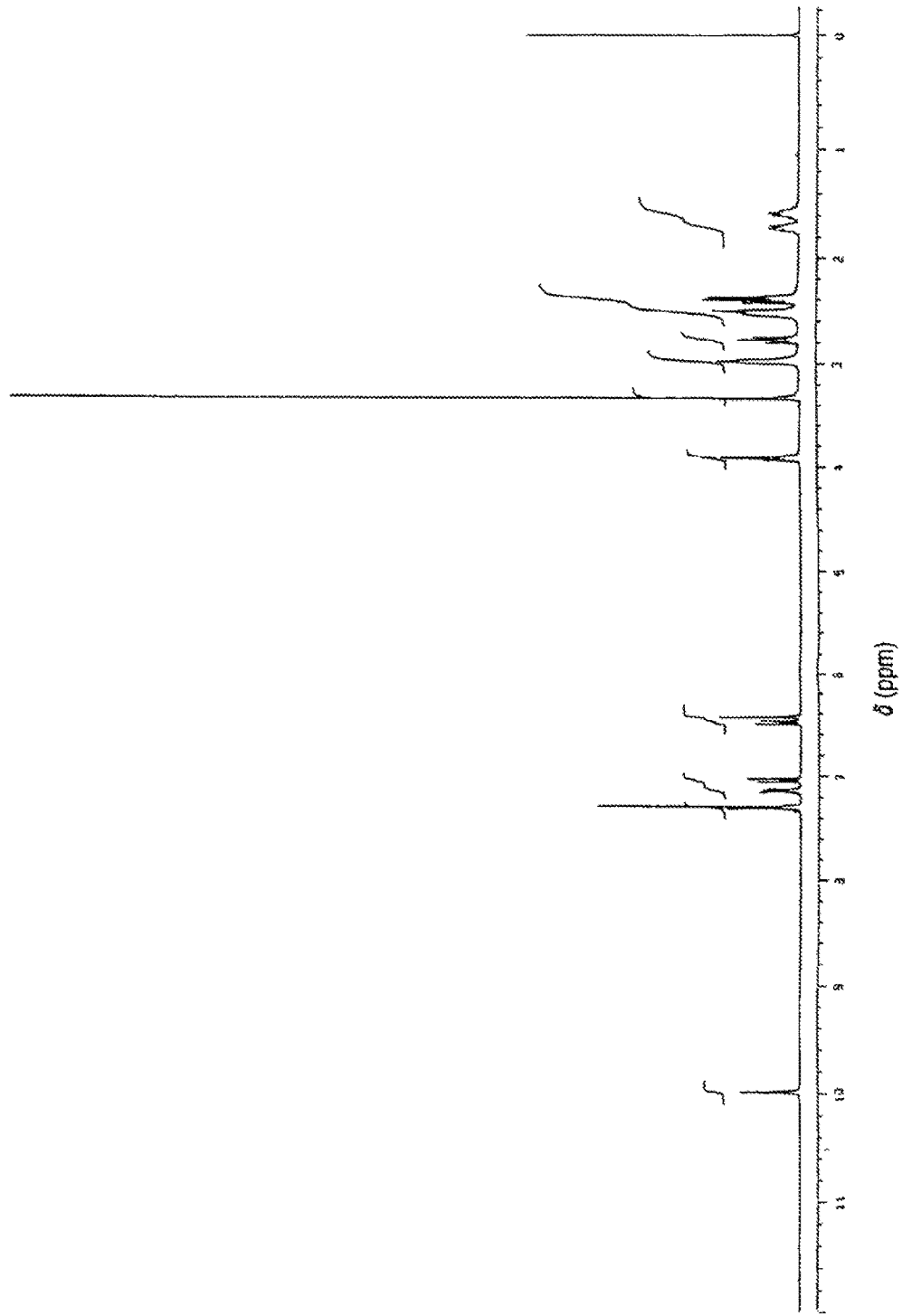
FIG. 27 shows an $^1$H-NMR spectrum (DMSO-dg, TMS) of the type G crystals of anhydrous aripiprazole obtained in Example 16-b).

(20) an $^1$H-NMR spectrum which is substantially identical to the $^1$H-NMR spectrum (DMSO-$d_6$, TMS) shown in FIG. 27.

Figure 28:
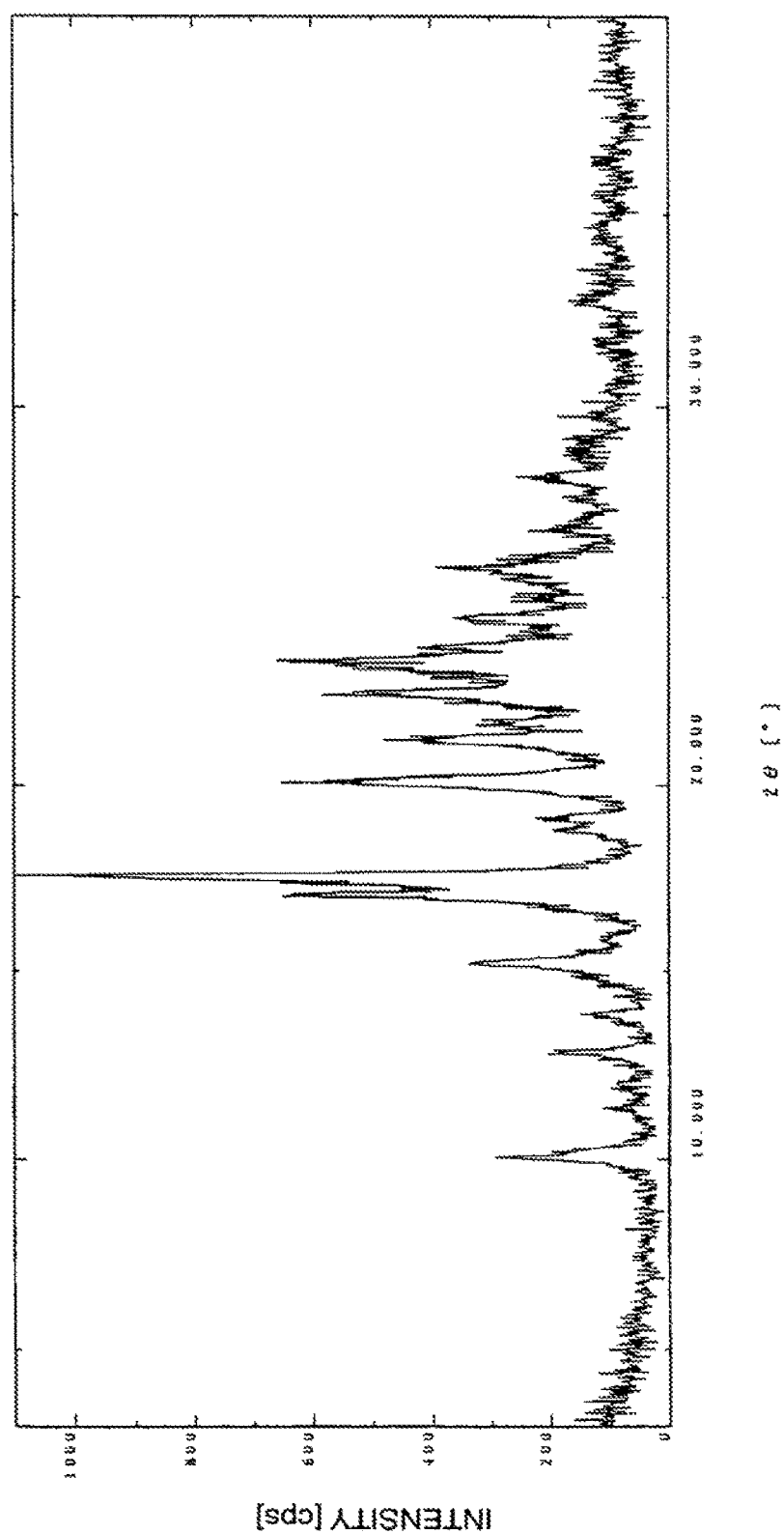
FIG. 28 shows a powder X-ray diffraction spectrum of the type G crystals of anhydrous aripiprazole obtained in Example 16-b).

(21) a power X-ray diffraction spectrum which is substantially identical to the power X-ray diffraction spectrum shown in FIG. 28; and

Figure 29:
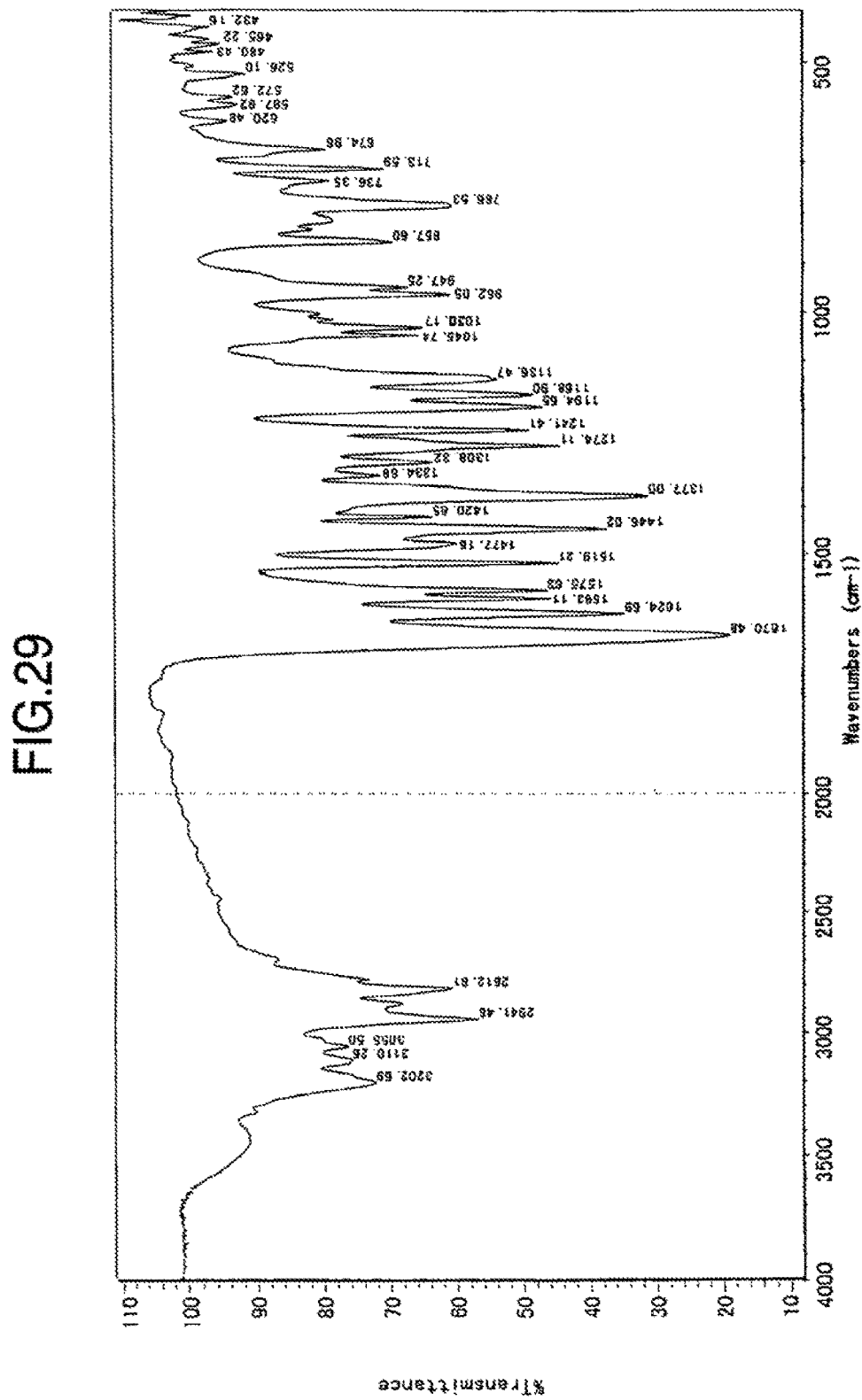
FIG. 29 shows an IR spectrum of the type G crystals of anhydrous aripiprazole obtained in Example 16-b).

(22) an IR spectrum which is substantially identical to the IR (Kbr) shown in FIG. 29.

11. The present invention relates to a process for preparing anhydrous aripiprazole crystals stated in the aforementioned item 10, characterized by putting glassy state of Anhydrous Aripiprazole in a sealed vessel and keeping it at room temperature for at least 2 weeks.

12. The present invention relates to a process for the preparation of granules, characterized by wet granulating conventional Anhydrous Aripiprazole Crystals or Anhydrous Aripiprazole Crystals B, C, D, E, F or G, drying the obtained granules at 70 to 100° C. and sizing it, then drying the sized granules at 70 to 100° C. again.

13. The present invention relates to a process for the pharmaceutical solid oral preparation, characterized by drying a pharmaceutical solid oral preparation comprising conventional Anhydrous Aripiprazole Crystals or Anhydrous Aripiprazole Crystals B, C, D, E, F or G, and one or more pharmaceutically acceptable carriers at 70 to 100° C.

14. The present invention relates to a pharmaceutical solid oral preparation comprising Anhydrous Aripiprazole Crystals B, C, D, E, F or G and one or more pharmaceutically acceptable carriers, wherein said pharmaceutical solid oral preparation has at least one dissolution rate selected from the group consisting 60% or more at pH 4.5 after 30 minutes, 70% or more at pH 4.5 after 60 minutes, and 55% or more at pH 5.0 after 60 minutes.

15. The present invention relates to a pharmaceutical solid oral preparation having at least one dissolution rate selected from the group consisting 60% or more at pH 4.5 after 30 minutes, 70% or more at pH 4.5 after 60 minutes, and 55% or more at pH 5.0 after 60 minutes.

16. The present invention relates to a pharmaceutical solid oral preparation obtained by wet granulating conventional Anhydrous Aripiprazole Crystals, drying the obtained granules at 70 to 100° C. and sizing it, then drying the sized granules at 70 to 100° C. again, and the pharmaceutical solid oral preparation has at least one dissolution rate selected from the group consisting 60% or more at pH 4.5 after 30 minutes, 70, or more at pH 4.5 after 60 minutes, and 55% or more at pH 5.0 after 60 minutes.

17. The present invention relates to a pharmaceutical solid oral preparation obtained by drying a pharmaceutical solid oral preparation comprising conventional Anhydrous Aripiprazole Crystals and one or more pharmaceutically acceptable carriers at 70 to 100° C., and the pharmaceutical solid oral preparation has at least one dissolution rate selected from the group consisting 60% or more at pH 4.5 after 30 minutes, 70% or more at pH 4.5 after 60 minutes, and 55% or more at pH 5.0 after 60 minutes.

18. The present invention relates to a process for the preparation of granules, characterized by wet granulating conventional Aripiprazole Hydrate Crystals, drying the obtained granules at 70 to 100° C. and sizing it, then drying the sized granules at 70 to 100° C. again.

19. The present invention relates to a process for the pharmaceutical solid oral preparation, characterized by drying a pharmaceutical solid oral preparation comprising conventional Aripiprazole Hydrate Crystals and one or more pharmaceutically acceptable carriers at 70 to 100° C.

20. The present invention relates to a pharmaceutical solid oral preparation obtained by wet granulating conventional Aripiprazole Hydrate Crystals, drying the obtained granules at 70 to 100° C. and sizing it, then drying the sized granules at 70 to 100° C. again, and the pharmaceutical solid oral preparation has at least one dissolution rate selected from the group consisting 60% or more at pH 4.5 after 30 minutes, 70% or more at pH 4.5 after 60 minutes, and 55% or more at pH 5.0 after 60 minutes.

21. The present invention relates to a pharmaceutical solid oral preparation obtained by drying a pharmaceutical solid oral preparation comprising conventional Aripiprazole Hydrate Crystals and one or more pharmaceutically acceptable carriers at 70 to 100° C., and the pharmaceutical solid oral preparation has at least one dissolution rate selected from the group consisting 60% or more at pH 4.5 after 30 minutes, 70% or more at pH 4.5 after 60 minutes, and 55% or more at pH 5.0 after 60 minutes.

The Type C to F crystals of anhydrous aripiprazole of the present invention correspond to the Type-III to VI crystals of anhydrous aripiprazole disclosed in JP-2001-348276.

Type C Crystals of Anhydrous Aripiprazole

Type C crystals of anhydrous aripiprazole of the present invention have the following physicochemical properties (1) to (5):

(1) an endothermic curve which is substantially identical to the thermogravimetric/differential thermal analysis (heating rate: 5° C./min.) endothermic curve shown in FIG. 8, more particularly, it has an endothermic peak around 150.2° C.;

(2) an $^1$H-NMR spectrum which is substantially identical to the $^1$H-NMR spectrum (DMSO-di, TMS) shown in FIG. 9. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7, 4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H);

(3) a powder X-ray diffraction spectrum which is substantially identical to the powder X-ray diffraction spectrum shown in FIG. 10. Specifically, it has characteristic peaks at 2θ=12.6°, 13.7°, 15.4°, 18.1°, 19.0°, 20.6°, 23.5° and 26.4°;

(4) an IR spectrum which is substantially identical to the IR (KBr) spectrum shown in FIG. 11. Specifically, it has clear infrared absorption bands at 2939, 2804, 1680, 1375 and 780 cm$^{-1}$; and (5) a solid $^{13}$C-NMR spectrum which is substantially identical to the solid $^{13}$C-NMR spectrum shown in FIG. 12, specifically, it has characteristic peaks at 32.8 ppm, 60.8 ppm, 74.9 ppm, 104.9 ppm, 152.2 ppm, 159.9 ppm and 1.75.2 ppm.

Preparation Method of Type C Crystals of Anhydrous Aripiprazole

Type C crystals of anhydrous aripiprazole of the present invention is prepared, for example by heating an anhydrous aripiprazole at a temperature of higher than 140° C. and lower than 150° C.

Anhydrous aripiprazole used as the raw material may be conventional anhydrous aripiprazole crystals, for example, type-I crystals of anhydrous aripiprazole, type-II crystals of anhydrous aripiprazole crystals and the like, and these anhydrous aripiprazoles may be either purified products or crude materials. Alternatively, type B crystals of anhydrous aripiprazole, type D crystals of anhydrous aripiprazole, type E crystals of anhydrous aripiprazole, type E crystals of anhydrous aripiprazole, or type G crystals of anhydrous aripiprazole being prepared in the present invention can be used as the raw material of anhydrous aripiprazole. These anhydrous aripiprazoles can be used singly or in combination of at least 2 kinds thereof.

Heating temperature is generally higher than 140° C. and lower than 150° C., preferably at 142-148° C., and heating time is generally for 15 minutes to 3 hours, preferably for 30 minutes to 1 hour.

When, an anhydrous aripiprazole is heated at the above-mentioned temperature, then type C crystals of anhydrous aripiprazole are formed.

Thus obtained type C crystals of anhydrous aripiprazole can be isolated and purified by well-known methods. For example, after heating the anhydrous aripiprazole at the above-mentioned temperature, and by cooling to a room temperature, then type C crystals of anhydrous aripiprazole, having 100% of purity can be obtained.

Type D Crystals of Anhydrous Aripiprazole

Type D crystals of anhydrous aripiprazole of the present invention have the following physicochemical properties (6) to (10):

(6) an endothermic curve which is substantially identical to the thermogravimetric/differential thermal analysis (heating rate: 5° C./min.) endothermic curve shown in FIG. 13; more particularly, it has an endothermic peak around 136.8° C. and 141.6° C.;

(7) an $^1$H-NMR spectrum which is substantially identical to the $^1$H-NMR spectrum (DMSO-$d_6$, TMS) shown in FIG. 14. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7, 4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H);

(8) a powder X-ray diffraction spectrum which is substantially identical to the powder X-ray diffraction spectrum shown in FIG. 15. Specifically, it has characteristic peaks at 2θ=8.7°, 11.6°, 16.3, 17.7°, 18.6°, 20.3°, 23.4° and 25.0°;

(9) an IR spectrum which is substantially identical to the IR (KBr) spectrum shown in FIG. 16. Specifically, it has clear infrared absorption bands at 2946, 1681, 1375, 1273, 1175 and 862 $cm^{-1}$; and

(10) a solid $^{13}$C-NMR spectrum which is substantially identical to the solid $^{13}$C-NMR spectrum shown in FIG. 17, specifically, it has characteristic peaks at 32.1 ppm, 62.2 ppm, 66.6 ppm, 104.1 ppm, 152.4 ppm, 158.4 ppm, and 174.1 ppm.

Preparation Method of Type D Crystals of Anhydrous Aripiprazole

Type D crystals of anhydrous aripiprazole of the present invention is prepared, for example, by recrystallization of anhydrous aripiprazole from toluene. Specifically, an anhydrous aripiprazole is added to toluene, further heated and dissolved, then thus obtained solution is cooled. By such procedures, type D crystals of anhydrous aripiprazole of the present invention is separated out as crystals in toluene.

Anhydrous aripiprazole to be used as the raw materials may be conventional anhydrous aripiprazole, for example type-I crystals of anhydrous aripiprazole, type-II crystals of anhydrous aripiprazole and the like, and these anhydrous aripiprazoles may be either purified products or crude materials. Alternatively, type B crystals of anhydrous aripiprazole, type C crystals of anhydrous aripiprazole, type E crystals of anhydrous aripiprazole, type F crystals of anhydrous aripiprazole, or type G crystals of anhydrous aripiprazole being prepared in the present invention can be used as the raw material for anhydrous aripiprazoles. These anhydrous aripiprazoles can be used singly or in combination of at least 2 kinds thereof.

When the solution obtained by heating and dissolving is cooled, type D crystals of anhydrous aripiprazole may be added as a seed crystal to said solution. Further, the seed crystal may be formed by cooling gradually said solution being obtained by heating and dissolving. In the presence of the seed crystal, type D crystals of anhydrous aripiprazole may be separated out.

Thus separated out type D crystals of anhydrous aripiprazole can be isolated and purified in accordance with well-known methods. By such procedures, type D crystals of anhydrous aripiprazole, having the purity of 100% can be obtained.

Type E Crystals of Anhydrous Aripiprazole

Type E crystals of anhydrous aripiprazole of the present invention have the following physicochemical properties (11) to (14):

(11) an endothermic curve which is substantially identical to the thermogravimetric/differential thermal analysis (heating rate: 5° C./min.) endothermic curve shown in FIG. 18, specifically, it has an endothermic peak around 146.5° C.;

(12) an $^1$H-NMR spectrum which is substantially identical to the $^1$H-NMR spectrum (DMSO-$d_6$, TMS) shown in FIG. 19. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7, 4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H);

(13) a powder X-ray diffraction spectrum which is substantially identical to the powder X-ray diffraction spectrum shown in FIG. 20. Specifically, it has characteristic peaks at 2θ=8.0°, 13.7°, 14.6°, 17.6°, 22.5° and 24.0°; and

(14) an IR spectrum which is substantially identical to the IR (KBr) spectrum shown in FIG. 21. Specifically, it has clear infrared absorption bands at 2943, 2817, 1686, 1377, 1202, 969 and 774 $cm^{-1}$.

Preparation Method of Type E Crystals of Anhydrous Aripiprazole

Type E crystals of anhydrous aripiprazole of the present invention is prepared, for example by recrystallization of the anhydrous aripiprazole from acetonitrile. Specifically, by adding a well-known anhydrous aripiprazole to acetonitrile, heating and dissolving, then the solution thus obtained may be cooled. In accordance with such procedures, type E crystals of anhydrous aripiprazole of the present invention are separated out in the acetonitrile.

When a conventional anhydrous aripiprazole is added to acetonitrile, type-I crystals of anhydrous aripiprazole, type-II crystals of anhydrous aripiprazole and type D crystals of anhydrous aripiprazole are separated out, other than type E crystals of anhydrous aripiprazole. Plate crystals being separated out from the acetonitrile solution at 70° C. are type-I crystals, type-II crystals and type D crystals, while type E crystals are precipitated out as needle crystals. When the acetonitrile solution after separated out of these crystals is heated again (for example, heated at over 75° C.), the plate crystals (type-I crystals, type-II crystals and type D crystals) are quickly dissolved, on the contrary, the needle form crystals (type E crystals) do not dissolved. Additionally, when the acetonitrile solution is cooled again, then needle form crystals (type E crystals) are further separated out around the needle form crystals (type E crystals) previously precipitated as the seed crystals. Thus, type E crystals of anhydrous aripiprazole can be precipitated in the acetonitrile solution.

Anhydrous aripiprazoles used as the raw materials may be conventional anhydrous aripiprazoles, for example any one of type-I crystals of anhydrous aripiprazole and type-II crystals of anhydrous aripiprazole and the like, and these anhydrous aripiprazoles may be either purified products or crude materials. Alternatively, type B crystals of anhydrous aripiprazole, type C crystals of anhydrous aripiprazole, type D crystals of anhydrous aripiprazole, type F crystals of anhydrous aripiprazole, or type G crystals of anhydrous aripiprazole can be used as the raw materials for anhydrous aripiprazoles. These anhydrous aripiprazoles can be used singly or in combination of at least 2 kinds thereof.

When the acetonitrile solution obtained by heating (heating and dissolving) is cooled, the type E crystals of aripiprazole may be added as a seed crystal to said solution. Further, the seed crystal may be formed by cooling gradually said acetonitrile solution which was obtained by heating.

Thus separated out type E crystals of anhydrous aripiprazole can be isolated and purified in accordance with well-known methods. By such procedures, type E crystals of anhydrous aripiprazole, having the purity of 100% can be obtained.

Type F Crystals of Anhydrous Aripiprazole

Type F crystals of anhydrous aripiprazole of the present invention have the following physicochemical properties (15) to (18):

(15) an endothermic curve which is substantially identical to the thermogravimetric/differential thermal analysis (heating rate: 5° C./min.) endothermic curve shown in FIG. 22, specifically, it has an endothermic peaks around 137.5° C. and 149.8° C.;

(16) an $^1$H-NMR spectrum which is substantially identical to the $^1$H-NMR spectrum (DMSO-$d_6$, TMS) shown in FIG. 23. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7, 4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H);

(17) a powder X-ray diffraction spectrum which is substantially identical to the powder X-ray diffraction spectrum shown in FIG. 24. Specifically, it has characteristic peaks at 2θ=11.3, 13.3°, 15.4°, 22.8°, 25.2° and 26.9°, and

(18) Having an IR spectrum which is substantially identical to the IR (KBr) spectrum shown in FIG. 25. Specifically, it has clear infrared absorption bands at 2940, 2815, 1679, 1383, 1273, 1177, 1035, 963 and 790 cm$^{-1}$.

Preparation Method of Type F Crystals of Anhydrous Aripiprazole

Type F crystals of anhydrous aripiprazole of the present invention is prepared, for example by suspending an anhydrous aripiprazole in acetone, and thus obtained acetone suspension is heated.

Anhydrous aripiprazoles used as the raw materials may be conventional anhydrous aripiprazole, for example any one of type-I crystals of anhydrous aripiprazole and type-II crystals of anhydrous aripiprazole and the like, and these anhydrous aripiprazoles may be either purified products or crude materials. Alternatively, type B crystals of anhydrous aripiprazole, type C crystals of anhydrous aripiprazole, type D crystals of anhydrous aripiprazole, type E crystals of anhydrous aripiprazole, or type G crystals of anhydrous aripiprazole prepared in the present invention can be used as the raw materials for anhydrous aripiprazoles. These anhydrous aripiprazoles can be used singly or in combination of at least 2 kinds thereof.

Heating temperature of the acetone suspension may be generally about the boiling point of acetone, and heating time is generally 5 to 10 hours. When the acetone suspension is heated about the boiling point of acetone, then type F crystals of anhydrous aripiprazole is formed, the crystals are isolated by filtration with heating. Isolation of the crystals may be carried out in accordance with well-known methods. By such procedures, type F crystals of anhydrous aripiprazole, having the purity of 100% can be obtained.

Type G Crystals of Anhydrous Aripiprazole

Type G crystals of anhydrous aripiprazole of the present invention have the following physicochemical properties (19) to (22):

(19) an endothermic curve which is substantially identical to the thermogravimetric/differential thermal analysis (heating rate: 5° C./min.) endothermic curve shown in FIG. 26, more particularly, it has an endothermic peak around 141.0° C. and an exothermic peak around 122.7° C.;

(20) an $^1$H-NMR spectrum which is substantially identical to the $^1$H-NMR spectrum (DMSO-$d_6$, TMS) shown in FIG. 27. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 6.49 ppm (dd, J=8.4 Hz, J=2.4 Hz, 1H), 7.04 ppm (d, J=8.1 Hz, 18), 7.11-7.17 ppm (m, 18), 7.28-7.32 ppm (m, 2H) and 10.00 ppm (s, 1H);

(21) a powder X-ray diffraction spectrum which is substantially identical to the powder X-ray diffraction spectrum shown in FIG. 28. Specifically, it has characteristic peaks at 2θ=10.1°, 12.8°, 0.5.2°, 17.0°, 17.5°, 19.1°, 20.1°, 21.2°, 22.4°, 23.3°, 24.5° and 25.8°; and

(22) an IR spectrum which is substantially identical to the IR (KBr) spectrum shown in FIG. 29. Specifically, it has clear infrared absorption bands at 2942, 2813, 1670, 1625, 1377, 1195, 962 and 787 cm$^{-1}$.

Preparation Method of Type G Crystals of Anhydrous Aripiprazole

Type G crystals of anhydrous aripiprazole of the present invention can be prepared, for example by putting glassy state of anhydrous aripiprazole in a sealed vessel and leaving to stand it at room temperature for at least two weeks, preferably two weeks to six months. Further, glassy state of anhydrous aripiprazole as starting material can be obtained by heating and melting anhydrous aripiprazole at around 170° C., then cooling it to room temperature.

Anhydrous aripiprazole used as the raw material may be well-known anhydrous aripiprazole crystals, for example, any one of type-I crystals of anhydrous aripiprazole and type-II crystals of anhydrous aripiprazole and the like, and these anhydrous aripiprazoles may be either purified products or crude materials. Alternatively, type B crystals of anhydrous aripiprazole, type C crystals of anhydrous aripiprazole, type D crystals of anhydrous aripiprazole, type E crystals of anhydrous aripiprazole, or type F crystals of anhydrous aripiprazole being prepared in the present invention can be used as the raw material of anhydrous aripiprazoles. These anhydrous aripiprazoles can be used singly or in combination of at least 2 kinds thereof.

Thus obtained type G crystals of anhydrous aripiprazole can be isolated and purified by well-known methods. For example, glassy state of anhydrous aripiprazole leave to stand according to the above-mentioned method, then type G crystals of anhydrous aripiprazole, having 100% of purity can be obtained.

Type C crystals of anhydrous aripiprazole, type D crystals of anhydrous aripiprazole, type E crystals of anhydrous aripiprazole, type F crystals of anhydrous aripiprazole and type G crystals of anhydrous aripiprazole of the present invention neither easily convert into hydrates thereof, nor substantially decrease the original solubility, even when they are stored for a long period of time.

In accordance with the present invention, methods for preparing anhydrous aripiprazole crystals having high purity, which can apply in an industrial scale with a good repeatability is provided.

In accordance with the present invention, pharmaceutical compositions comprising anhydrous aripiprazole crystals are provided, of which the solubility does not decrease, and of which the stability can keep excellent, even if they are stored for long time.

The anhydrous aripiprazole crystals which are the raw material for preparing the Anhydrous Aripiprazole Crystals B to G of the present invention are prepared for example by Method a or b below.

"Method a": Process for Preparing Crude Aripiprazole Crystals

Conventional Anhydrous Aripiprazole crystals are prepared by well-known methods, as described in Example 1 of Japanese Unexamined Patent Publication No. 191256/1990.

A suspension of 47 g of 7-(4-bromobutoxy)-3,4-dihydrocarbostyril, 35 g of sodium iodide with 600 ml of acetonitrile was refluxed for 30 minutes. To this suspension was added 40 g of 1-(2,3-dichlorophenyl)piperazine and 33 ml of triethylamine and the whole mixture was further refluxed for 3 hours. After the solvent was removed by evaporation, the residue thus obtained was dissolved in chloroform, washed with water then dried with anhydrous magnesium sulfate. The solvent was removed by evaporation, and the residue thus obtained was recrystallized from ethanol twice, to yield 57.1 g of 7-(4-[4-(2,3-dichlorophenyl)-1-piperazinyl]butoxy)-3,4-dihydrocarbostyril.

Colorless flake crystals

Melting point: 139.0-139.5° C.

"Method b": Process for Preparing Conventional Anhydrous Aripiprazole

The Method b is described in the Proceedings of the 4th Japanese-Korean Symposium on Separation Technology (Oct. 6-8, 1996).

Furthermore, the Anhydrous Aripiprazole Crystals B of the present invention are prepared for example by heating conventional aripiprazole hydrate at 90-125° C. The heating time is generally about 3-50 hours, but cannot be stated unconditionally since it differs depending on heating temperature. The heating time and heating temperature are inversely related, so that for example the heating time will be longer the lower the heating temperature, and shorter the higher the heating temperature. Specifically, if the heating temperature of the aripiprazole hydrate is 100° C., the heating time can be about 24 hours, while if the heating temperature is 120° C., the heating time can be about 3 hours.

The aripiprazole hydrate which is the raw material for preparing the Anhydrous Aripiprazole Crystals B of the present invention is prepared for example by Method c below.

"Method c": Process for Preparing Conventional Hydrate

Aripiprazole hydrate is easily obtained by dissolving the anhydrous aripiprazole crystals obtained by Method a above in a hydrous solvent, and heating and then cooling the resulting solution. Using this method, aripiprazole hydrate is precipitated as crystals in the hydrous solvent.

An organic solvent containing water is usually used as the hydrous solvent. The organic solvent should be one which is miscible with water, such as for example an alcohol such as methanol, ethanol, propanol or isopropanol, a ketone such as acetone, an ether such as tetrahydrofuran, dimethylformamide, or a mixture thereof, with ethanol being particularly desirable. The amount of water in the hydrous solvent can be 10-25% by volume of the solvent, or preferably close to 20% by volume.

Medicinal Composition

A medicinal composition of the present invention will contain Anhydrous Aripiprazole Crystals B, C, D, E, F and G in a pharmaceutically acceptable carrier or combination of carriers.

Carriers which are pharmaceutically acceptable include diluents and excipients generally used in pharmaceuticals, such as fillers, extenders, binders, moisturizers, disintegrators, surfactants, and lubricants.

The medicinal composition of the present invention may be formulated as an ordinary medicinal preparation, for example in the form of tablets, flashmelt tablets, pills, powder, liquid, suspension, emulsion, granules, capsules, suppositories or as an injection (liquid, suspension, etc.).

When a tablet formulation is used, a wide variety of carriers that are known in the field can be used. Examples include lactose, saccharose, sodium chloride, glucose, xylitol, mannitol, erythritol, sorbitol, urea, starch, calcium carbonate, kaolin, crystal cellulose, silic acid and other excipients; water, ethanol, propanol, simple syrup, glucose liquid, starch liquid, gelatin solution, carboxymethyl cellulose, shellac, methyl cellulose, potassium phosphate, polyvinyl pyrolidone and other binders; dried starch, sodium alginate, agar powder, laminaran powder, sodium bicarbonate, calcium carbonate, polyoxyethylene sorbitan fatty acid esters, sodium lauryl sulfate, monoglyceride stearate, starch, lactose and other disintegrators; saccharose, stearin, cacao butter, hydrogenated oil and other disintegration inhibitors; quaternary ammonium salt, sodium lauryl sulfate and other absorption promoters; glycerine, starch and other moisture retainers; starch, lactose, kaolin, bentonite, colloidal silic acid and other adsorbents; and refined talc, stearate, boric acid powder, polyethylene glycol and other lubricants and the like. Tablets can also be formulated if necessary as tablets with ordinary coatings, such as sugar-coated tablets, gelatin-coated tablets, enteric coated tablets and film coated tablets, as well as double tablets and multilayered tablets.

When a pill formulation is used, a wide variety of carriers that are known in the field can be used. Examples include glucose, lactose, starch, cacao butter, hardened vegetable oil, kaolin, talc and other excipients; gum arabic powder, traganth powder, gelatin, ethanol and other binders; and laminaran, agar and other disintegrators and the like.

When a suppository formulation is used, a wide variety of carriers that are known in the field can be used. Examples include polyethylene glycol, cacao butter, higher alcohol, esters of higher alcohol, gelatin semi-synthetic glyceride and the like.

Capsules are prepared according to ordinary methods by mixing anhydrous aripiprazole crystals with the various carriers described above and packing them in hard gelatin capsules, soft capsules, hydroxypropylmethyl cellulose capsules (HPMC capsules) and the like.

In addition, colorants, preservatives, perfumes, flavorings, sweeteners and the like as well as other drugs may be included in the medicinal composition.

In case of forming the pharmaceutical solid oral preparation in the form of granules, it can be prepared by wet granulating a mixed powder of granulating ingredients comprising, anhydrous aripiprazole crystals (conventional anhydrous aripiprazole crystals or anhydrous aripiprazole crystals selected from the group consisting of anhydrous aripiprazole type B, C, D, E, F and G crystals) and various carriers which are heretofore well-known in this field, such as excipients, disintegrators, disintegration inhibitors, humectants, absorption accelerators, adsorbents, lubricants, colorants and the like (for the examples of these agents, those of previously mentioned can be referred to) by adding a liquid (generally, water or an aqueous solution containing binding agents). As for the wet granulation, there are various methods are included, for example, fluidized bed granulation, kneading granulation, extruding granulation, rotating granulation and the like can be mentioned. Among these methods, in case of conducting the fluidized bed granulation, the granulating ingredients containing various carriers are mixed with inlet air, then upon continued fluidizing the granulating ingredients and the liquid is sprayed to conduct granulation. In case of conducting the kneading granulation, the granulating ingredients containing various carriers are mixed by agitation, then upon continued agitating the granulating ingredients, granulation is conducted by adding the liquid. After the granulation, if necessary, the obtained granules are sized to make them to the desired size by use of a suitable sieve or a mill having suitable screen size. The granules thus obtained by such a method are dried again in addition to usual drying being conducted when preparing the granules. As for the drying methods, various methods can be applied, for example, methods by use of a fluidized bed dryer, a fan dryer, a vacuum dryer and the like can be mentioned. Generally, drying methods can be conducted under conventional conditions, for example, in case of using the fluidized bed dryer, drying procedure is conducted with an air flow of 0.5 $m^3$/min to 50 $m^3$/min, an inlet air temperature at 70 to 100° C. for 10 min to 1 hour. After dried, the granules are subjected to size, then further dried. In case of using the fluidized bed dryer or fan dryer or the like, the drying procedure is conducted under the conditions with an air flow of 0.5 $m^3$/min to 50 $m^3$/min, an inlet air temperature at 70 to 100° C. for 1 to 6 hours. In case of using the vacuum dryer, the drying procedure is conducted under the conditions of reduced pressure of about at 0-10 torr of degree of vacuum at 70 to 100° C. of jacket temperature for 1 to 6 hour.

The thus prepared granules may be used as they are for the pharmaceutical solid oral preparations, or if necessary, they may be shaped in the form of tablets. Further, the dried granules dried by usual manner are shaped in the form of tablets, then they may be dried again.

The thus prepared pharmaceutical solid oral preparation comprising anhydrous aripiprazole crystals hardly changes to hydrates even if they are stored for a long period of time, therefore the pharmaceutical solid oral preparation, of which dissolution rate does not hardly lowered (dissolution rate to maintain maximum drug concentration (Cmax): 60% or higher dissolution rate obtained after 30 minutes at pH 4.5, 70, or higher dissolution rate obtained after 60 minutes at pH 4.5, or 55% or higher dissolution rate obtained after 60 minutes at pH 5.0) can be provided.

Another pharmaceutical solid oral preparation can be provided by granulating a conventional aripiprazole hydrate crystals by a method similar to that of mentioned above, and dried by usual manner under similar conditions, then dried again. Alternatively, the dried granules dried by usual manner are shaped to tablets form, then they are dried again, then pharmaceutical solid oral preparations of which dissolution rate does not lowered (dissolution rate to maintain maximum drug concentration (Cmax): 60% or higher dissolution rate obtained after 30 minutes at pH 4.5, 70% or higher dissolution rate obtained after 60 minutes at pH 4.5 or 55% or higher dissolution rate obtained after 60 minutes at pH 5.0) can be provided. These facts can be understood that, the conventional anhydrous aripiprazole crystals or the aripiprazole hydrate crystals contained in the pharmaceutical solid oral preparation are changed to "B type crystals" of anhydrous aripiprazole by drying twice.

The amount of Anhydrous Aripiprazole Crystals B, C, D, E, F and G that should be included in the medicinal composition of the present invention can be selected from a wide range suitable for the indication sought to be treated. Generally, the Anhydrous Aripiprazole Crystals B should be present in about 1-70% by weight or particularly about 1-30% by weight based on the medicinal composition.

The method of administration of the medicinal composition of the present invention may be adjusted to suit, for example, the formulation of the drug product, the age, gender and other conditions (including the severity thereof) of the patient. In the case of tablets, pills, liquids, suspensions, emulsions, granules and capsules, for example, administration is oral. In the case of an injection, it is administered intravenously either by itself or mixed with an ordinary replenisher such as glucose or amino acids, or may also be administered by itself intramuscularly, intracutaneously, subcutaneously or intraperitoneally, as necessary. In the case of a suppository, administration is intrarectal.

The dosage of the medicinal composition of the present invention is selected depending on the usage, the age, gender and other conditions of the patient, the severity of the condition and so forth, but ordinarily the amount of anhydrous aripiprazole crystals can be about 0.1-10 mg per 1 kg of body weight per day. The preparation which is the unit of administration should contain in the range of about 1-100 mg of Anhydrous Aripiprazole Crystals B, more particularly 1-30 mg per unit dose.

The medicinal composition of the present invention is extremely stable, with substantially no decrease in solubility even when stored for long periods of time.

The medicinal composition of the present invention is effective in the prevention and treatment of central nervous system disorders such as schizophrenia and may also be effective in the treatment of intractable (drug-resistant, chronic) schizophrenia with cognitive impairment and intractable (drug-resistant, chronic) schizophrenia without cognitive impairment, anxiety including mild anxiety, mania including bipolar disorder acute mania and acute mania, bipolar disorder, depression including bipolar disorder depression, autism, Down's syndrome, attention deficit hyperactivity disorder (ADHD), Alzheimer's disease, Parkinson's disease and other neurodegenerative diseases, panic, obsessive compulsive disorder (OCD), sleep disorders, sexual dysfunction, alcohol and drug dependency, vomiting, motion sickness, obesity, miparticlee headache and cognitive impairment.

Analytical Methods (1) The $^1$H-NMR spectrum was measured in DMSO-de using TMS as the standard.

(2) Powder X-ray Diffraction

Using a Rigaku Denki RAD-2B diffraction meter, the powder x-ray diffraction pattern was measured at room temperature using a Cu Kα filled tube (35 kV 20 mA) as the x-ray source with a wide-angle goniometer, a 1° scattering slit, an 0.15 mm light-intercepting slit, a graphite secondary monochromator and a scintillation counter. Data collection was done in 2θ continuous scan mode at a scan speed of 5°/minute in scan steps of 0.02° in the range of 3° to 40°.

(3) The IR spectrum was measured by the KBr method.

(4) Thermogravimetric/Differential Thermal Analysis

Thermogravimetric/differential thermal analysis was performed using a Seiko SSC 5200 control unit and a TG/DTA 220 simultaneous differential thermal/thermogravimetric measurement unit. 5-10 mg samples were placed in open aluminum pans and heated from 20° C. to 200° C. in a dry nitrogen atmosphere at a heating rate of 5° C./minute. α-alumina was used as the standard substance.

(5) Differential Scanning Calorimetry

Thermogravimetric/differential thermal analysis was performed using a Seiko SSC 5200 control unit and a DSC 220C differential scanning calorimeter. 5-10 mg samples were placed in crimped aluminum pans and heated from 20° C. to 200° C. in a dry nitrogen atmosphere at a heating rate of 5° C./minute. α-alumina was used as the standard substance.

(6) Particle Size Measurement 0.1 g of the particles to be measured were suspended in a 20 ml n-hexane solution of 0.5 g soy lecithin, and particle size was measured using a size distribution meter (Microtrack HPA, Microtrack Co.).

(7) Hygroscopicity Test Method

One g of the sample was accurately weighed in a weighing bottle (diameter 5 cm), covered with kimwipes and left to rest in a 60° C./100% RH environment (water/dessicator). 24 hours later, the weighing bottle was removed, transferred to an environment of a room temperature and about 30% RH (magnesium chloride hexahydrate saturated water solution/ dessicator) and left to rest for 24 hours and the water content of the sample was measured by the Karl Fischer method.

(8) Solid $^{13}$C-NMR Spectrometry

Solid C-NMR spectrum was measured under the conditions as follows.

Measuring apparatus: CMX-360 Solid State NMR Spectrometer (manufactured by Chemagnetic Inc.)

Computer: SPARC Station 2 (manufactured by SUN Microsystem, Inc.)

OS, Software: Solalis 1.1.1 Rev. B (Registered trademark: UNIX), Spinsight Ver. 2.5

Name of measured pulse: TOSS method (TOSS is a program name of the apparatus) among CP/MAS method.

Width of measured puls: 900 puls was used under the condition of CP.

Measuring sample tube: Test tube made of zirconia, having the outside diameter of 7.5 mm, and inside capacity of 0.8 ml Revolution: 4250 Hz (Revolution per second Contact time: 1 msec.

Waiting time: 20 sec.

Integrated times: 512 times

Measuring temperature: About 25° C. temperature of outside of test tube)

External standard: Methyl group (δ 17.3) of hexamethylbenzene was used as the external standard.

The present invention is explained in more detail below using reference examples, examples, sample preparations and formulation examples.

Reference Example 1

19.4 g of 7-(4-chlorobutoxy)-3,4-dihydrocarbostyril and 16.2 g of 1-(2,3-dichlorophenyl) piperadine 1 hydrochloride were added to 8.39 g of potassium carbonate dissolved in 140 ml of water, and circulated for 3 hours under agitation. After reaction the mixture was cooled and the precipitated crystals filtered out. These crystals were dissolved in 350 ml of ethyl acetate, and about 210 ml of water/ethyl acetate azeotrope removed under reflux. The remaining solution was cooled, and the precipitated crystals filtered out. The resulting crystals were dried for 14 hours at 60° C. to produce 20.4 g (74.2%) of raw aripiprazole.

30 g of the raw aripiprazole obtained above was recrystallized from 450 ml of ethanol according to the methods described in Japanese Unexamined Patent Publication No. 191256/1990, and the resulting crystals dried for 40 hours at 80° C. to obtain anhydrous aripiprazole crystals. The yield was 29.4 g (98.0%).

The melting point (mp) of these anhydrous aripiprazole crystals was 140° C., matching the melting point of the anhydrous aripiprazole crystals described in Japanese Unexamined Patent Publication No. 191256/1990.

When these crystals were left for 24 hours in a dessicator set at humidity 100%, temperature 60° C., they exhibited hygroscopicity of 3.28 (see Table 1 below).

Reference Example 2

6930 g of the intermediate raw aripiprazole obtained in Reference Example 1 was heat dissolved in 138 liters of hydrous ethanol (water content 20%) according to the method presented at the 4th Japanese-Korean Symposium on Separation Technology, gradually (2-3 hours) cooled to room temperature, and then chilled to near 0° C. The precipitated crystals were filtered out, producing about 7200 g of aripiprazole hydrate (wet state).

The wet-state aripiprazole hydrate crystals obtained above were dried for 30 hours at 80° C. to obtain 6480 g (93.5%) of conventional anhydrous aripiprazole crystals. The melting point (mp) of these crystals was 139.5° C. These crystals were confirmed by the Karl Fischer method to be anhydrous, with a moisture value of 0.03%.

When left for 24 hours in a dessicator set at humidity 100%, temperature 60° C., these crystals exhibited hygroscopicity of 1.78% (see Table 1 below).

Reference Example 3

Figure 6:
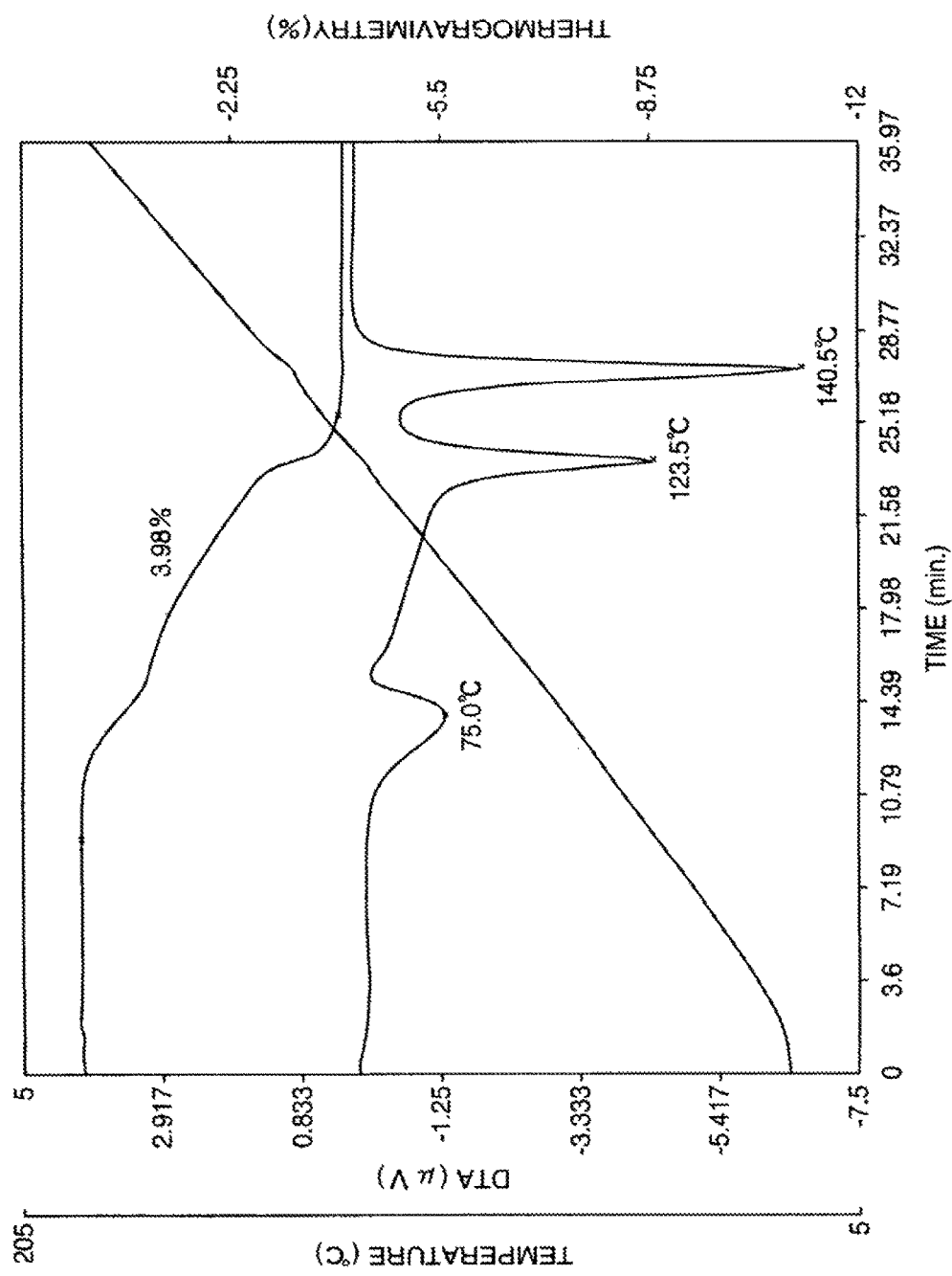
FIG. 6 is a thermogravimetric/differential thermogram of the aripiprazole hydrate obtained in Reference Example 3.

820 g of the intermediate wet-state aripiprazole hydrate obtained in Reference Example 2 was dried for 2 hours at 50° C. to obtain 780 g of aripiprazole hydrate crystals. These crystals had a moisture value of 3.82% according to the Karl. Fischer method. As shown in FIG. 6, thermogravimetric/ differential thermal analysis revealed endothermic peaks at 75.0, 123.5 and 140.5° C. Because dehydration began near 70° C., there was no clear melting point (mp).

Figure 7:
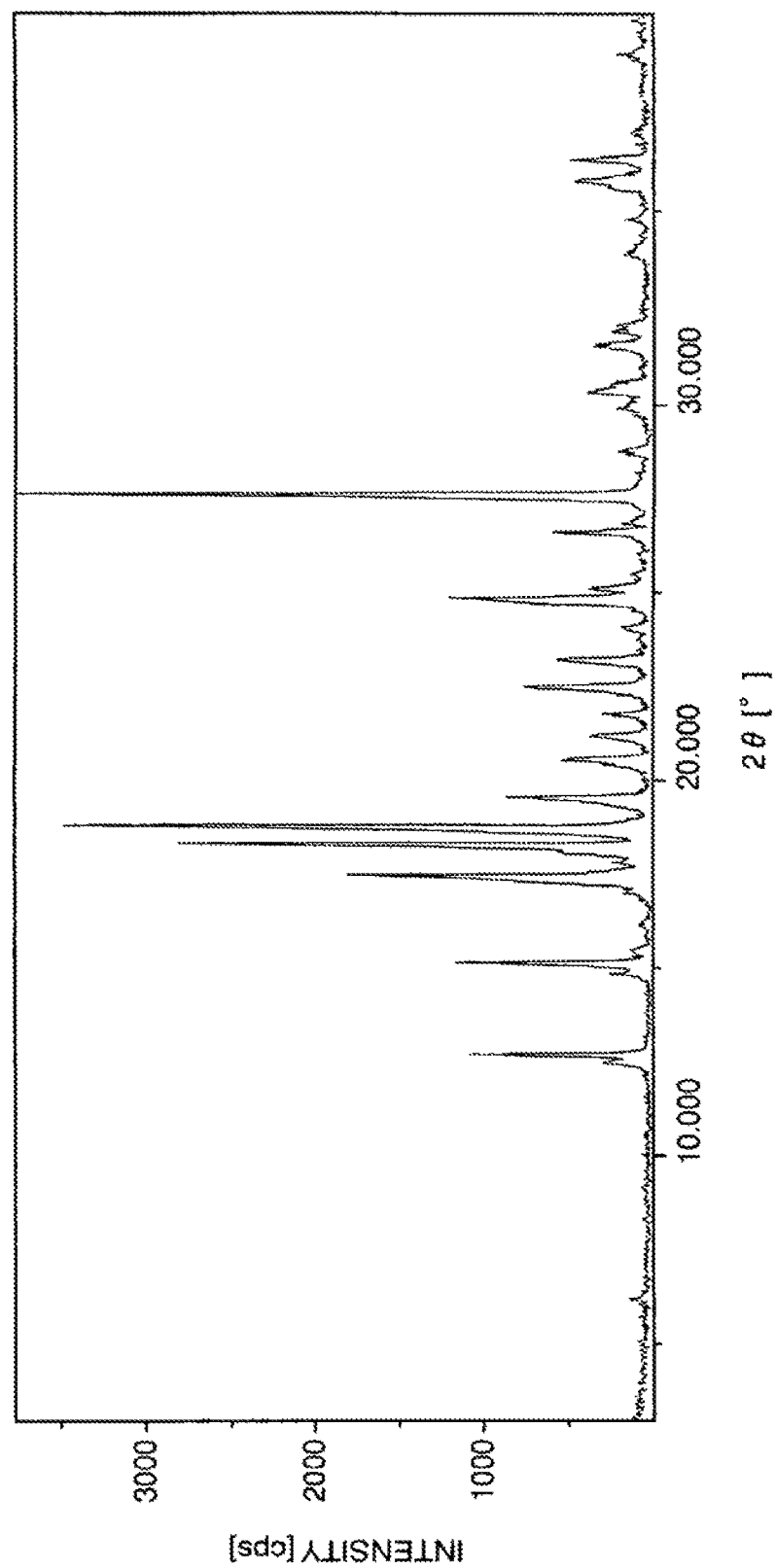
FIG. 7 is a powder x-ray diffraction diagram of the aripiprazole hydrate obtained in Reference Example 3.

As shown in FIG. 7, the powder x-ray diffraction spectrum of aripiprazole hydrate obtained by this method exhibited characteristic peaks at 2θ=12.6°, 15.1°, 17.4°, 18.2°, 18.7°, 24.8° and 27.5°.

The powder x-ray diffraction spectrum of this aripiprazole hydrate was identical to the powder x-ray diffraction spectrum of aripiprazole hydrate presented at the 4th Joint Japanese-Korean Symposium on Isolation Technology.

Reference Example 4

Preparation of 15 mg tablets containing type I crystals of anhydrous aripiprazole obtained in Reference Example 2.

Type-I crystals of anhydrous aripiprazole (525 g), lactose (1,995 g), corn starch (350 g) and crystalline cellulose (350 g) were charged in a fluidized bed granulating dryer (Flow coater FLO-5, manufactured by FREUND INDUSTRIAL CO., LTD.), and these granulating ingredients were mixed by fluidizing for about 3 minutes with an inlet air temperature at 70° C. and air flow rate of 3 m³/min. Further, the granulating ingredients were upon continued fluidizing under the same condition and sprayed about 1,400 g of the aqueous solution to obtained wet granules. The wet granules were dried under inlet air at temperature at 80° C., for about 15 minutes. The obtained dried granules contained 4.3% of water. (Yield: 99%). The dried granules were subjected to sizing by passing to a sieve of 710 μm.

About 1% by weight of magnesium stearate was added to the sized granules and mixed, then the granules were supplied to a tablet machine (Rotary single tablet press 12HUK: manufactured by KIKUSUI SEISAKUSHO CO., LTD.), there were obtained tablets, each having 95 mg of weight.

Water content of the tablets was measured according to volumetric titration method (Karl-Fischer method) described in water content measuring method in Japanese Pharmacopoea or the electrical quantity titration method.

Water Content Measuring Method:

Sample (0.1 to 0.5 g) (in case of a tablet, 1 tablet was used) was weighed precisely, and the water content was measured by use of a water content measuring equipment.

Volumetric Titration:

Automated water content measuring equipment Model: KF-06 (manufacture by MITSUBISHI CHEMICAL CORP.)

Electrical Quantity Titration Method:

Automated micro-water content measuring equipment Model: AQ-7F (manufactured by HIRANUMA SANGYO CO., LTD.)

Automated water vaporization equipment Model: LE-20S (manufactured by HIRANUMA SANGYO CO., LTD.)

Heating temperature: 165±10° C.

Nitrogen gas flow rate: about 150 ml/min.

Reference Example 5

Preparation of 15 mg tablets containing type B crystals of anhydrous aripiprazole Type B crystals of anhydrous aripiprazole (4,500 g), lactose (17,100 g), corn starch (3,000 g) and crystalline cellulose (3,000 g) were charged in a fluidized bed granulating dryer (NEW-MARUMERIZER Model: NQ-500, manufactured by FUJI PAUDAL CO., LTD.), and these granulating ingredients were mixed by fluidizing for about 3 minutes with an inlet air temperature at 70° C., air flow rate of 10 to 15 m³/min. Further, the granulating ingredients were upon continued fluidizing under the same condition, and sprayed about 12,000 g of 5% aqueous solution of hydrozypropyl cellulose to obtained wet granules. The wet granules were dried under inlet air at temperature at 85° C., for about 28 minutes. The thus obtained dried granules contained 3.8% of water (measured by the method according to Reference Example 4). (Yield: 96%). The dried granules were subjected to sizing by passing to a sieve of 850 μm.

About 1% by weight of magnesium stearate was added to the sized granules and mixed, then the granules were supplied to a tablet machine (Rotary single tablet press 12HUK: manufactured by KIKUSUI SEISAKUSHO CO., LTD.), there were obtained tablets, each having 95 mg of weight.

Example 1

500.3 g of the aripiprazole hydrate crystals obtained in Reference Example 3 were milled using a sample mill (small atomizer). The main axis rotation rate was set to 12,000 rpm and the feed rotation rate to 17 rpm, and a 1.0 mm herringbone screen was used. Milling was completed in 3 minutes, resulting in 474.6 g (94.9%) of Aripiprazole Hydrate A powder.

The Aripiprazole Hydrate A (powder) obtained in this way had a mean particle size of 20-25 μm. The melting point (np) was undetermined because dehydration was observed beginning near 70° C.

The Aripiprazole Hydrate A (powder) obtained above exhibited an $^1$H-NMR (DMSO-$d_6$, TMS) spectrum which was substantially the same as the $^1$H-NMR spectrum shown in FIG. 2. Specifically, it had characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The Aripiprazole Hydrate A (powder) obtained above had a powder x-ray diffraction spectrum which was substantially the same as the powder x-ray diffraction spectrum shown in FIG. 3. Specifically, it had characteristic peaks at 2θ=12.6°, 15.4°, 17.3°, 18.0°, 18.6°, 22.5° and 24.8°. This pattern is different from the powder x-ray spectrum of unmilled aripiprazole hydrate shown in FIG. 7.

The Aripiprazole Hydrate A (powder) obtained above had infrared absorption bands at 2951, 2822, 1692, 1577, 1447, 1378, 1187, 963 and 784 cm$^{-1}$ on the IR (KBr) spectrum.

As shown in FIG. 1, the Aripiprazole Hydrate A (powder) obtained above had a weak peak at 71.3° C. in thermogravimetric/differential thermal analysis and a broad endothermic peak (weight loss observed corresponding to one water molecule) between 60-120° C.—clearly different from the endothermic curve of unmilled aripiprazole hydrate (see FIG. 6).

Example 2

450 g of the Aripiprazole Hydrate A (powder) obtained in Example 1 was dried for 24 hours at 100° C. using a hot air dryer to produce 427 g (yield 98.7%) of Anhydrous Aripiprazole Crystals B.

These Anhydrous Aripiprazole Crystals B had a melting point (mp) of 139.7° C.

The Anhydrous Aripiprazole Crystals B obtained above had an $^1$H-NMR spectrum (DMSO-$d_6$, TMS) which was substantially the same as the $^1$H-NMR spectrum shown in FIG. 4. Specifically, they had characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The Anhydrous Aripiprazole Crystals B obtained above had a powder x-ray diffraction spectrum which was substantially the same as the powder x-ray diffraction spectrum shown in FIG. 5. Specifically, they had characteristic peaks at 2θ=11.0°, 16.6°, 19.3°, 20.3° and 22.1°.

The Anhydrous Aripiprazole Crystals B obtained above had remarkable infrared absorption bands at 2945, 2812, 1678, 1627, 1448, 1377, 1173, 960 and 779 cm$^{-1}$ on the IR (KBr) spectrum.

The Anhydrous Aripiprazole Crystals B obtained above exhibited an endothermic peak near about 141.5° C. in thermogravimetric/differential thermal analysis.

The Anhydrous Aripiprazole Crystals B obtained above exhibited an endothermic peak near about 140.7° C. in differential scanning calorimetry.

Even when the Anhydrous Aripiprazole Crystals B obtained above were left for 24 hours in a dessicator set at humidity 100%, temperature 60° C., they did not exhibit hygroscopicity exceeding 0.4% (See Table 1 below).

Example 3

44.29 kg of the Aripiprazole Hydrate A (powder) obtained in Example 1 was dry heated for 18 hours in a 100° C. hot air dryer and then heated for 3 hours at 120° C. to produce 42.46 kg (yield 99.3%) of Anhydrous Aripiprazole Crystals B.

The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Example 4

40.67 kg of the Aripiprazole Hydrate A (powder) obtained in Example 1 was dry heated for 18 hours in a 100° C. hot air dryer and then heated for 3 hours at 120° C. to produce 38.95 kg (yield 99.6%) of Anhydrous Aripiprazole Crystals B.

The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Examples 5-10 are useful for injectable or oral solution formulations but not solid dose formulations since they were made by heating Conventional Anhydrous Aripiprazole or Conventional Hydrate instead of Hydrate A.

Example 5

The hygroscopic anhydrous aripiprazole crystals obtained in Reference Example 1 were heated for 50 hours at 100° C. using the same methods as in Example 2. The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Example 6

The hygroscopic anhydrous aripiprazole crystals obtained in Reference Example 1 were heated for 3 hours at 120° C. using the same methods as in Example 2. The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Example 7

The hygroscopic anhydrous aripiprazole crystals obtained in Reference Example 2 were heated for 50 hours at 100° C. using the same methods as in Example 2. The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Example 8

The hygroscopic anhydrous aripiprazole crystals obtained in Reference Example 2 were heated for 3 hours at 120° C. using the same methods as in Example 2. The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Example 9

The aripiprazole hydrate crystals obtained in Reference Example 3 were heated for 50 hours at 100° C. using the same methods as in Example 2. The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way did not exhibit hygroscopicity of more than 0.4% even when left for 24 hours in a dessicator set at humidity 100%, temperature 60° C. (see Table 1 below).

Example 10

The aripiprazole hydrate crystals obtained in Reference Example 3 were heated for 3 hours at 120° C. using the same methods as in Example 2. The physicochemical properties of the resulting Anhydrous Aripiprazole Crystals B were the same as the physicochemical properties of the Anhydrous Aripiprazole Crystals B obtained in Example 2.

The Anhydrous Aripiprazole Crystals B obtained in this way exhibited hygroscopicity of no more than 0.4% even when left for 24 hours in a dessicator set at humidity 100%, temperature 60° C. (see Table 1 below).

Example 11 (Preparation of Type C Crystals of Anhydrous Aripiprazole)

100 Milligrams of type-I crystals of anhydrous aripiprazole obtained in Reference Example 2 were heated about 145° C. (±3° C.). In this occasion, there was observed the phenomena that the crystals were once melted, then again crystallized. After that, 100 mg (yield: 100%) of Type C crystals of anhydrous aripiprazole were obtained. The melting point of the crystals was 150° C. The crystals were colorless prism form.

The type C crystals of anhydrous aripiprazole obtained above had an endothermic curve which was substantially identical to the endothermic curve of thermogravimetric/differential thermal analysis (heating rate: 5° C./minute) shown in FIG. 8. Specifically, it showed the endothermic curve around 150.2° C.

The type C crystals of anhydrous aripiprazole thus obtained exhibited an $^1$H-NMR spectrum (DMSO-$d_6$, TMS)

which was substantially identical to the $^1$H-NMR spectrum (DMSO-d$_6$, TMS) shown in FIG. 9. Specifically, it had the characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H), and 10.00 ppm (s, 1H).

The type C crystals of anhydrous aripiprazole obtained above had a powder X-ray diffraction spectrum which was substantially identical to the powder X-ray diffraction spectrum shown in FIG. 10. Specifically, it had the characteristic peaks at 2θ=12.6°, 13.7°, 15.4°, 18.1°, 19.0°, 20.6°, 23.5° and 26.4°.

The type C crystals of anhydrous aripiprazole obtained above had an IR spectrum which was substantially identical to the IR (KBr) spectrum shown in FIG. 11. Specifically, it had the characteristic infrared absorption bands at 2939, 2804, 1680, 1375 and 780 cm$^{-1}$.

The type C crystals of anhydrous aripiprazole obtained above exhibited a solid $^{13}$C-NMR spectrum, which was substantially identical to the solid $^{13}$C-NMR spectrum shown in FIG. 12. Specifically, it had the characteristic peaks at 32.8 ppm, 60.8 ppm, 74.9 ppm, 104.9 ppm, 152.2 ppm, 159.9 ppm and 175.2 ppm.

According to the above-mentioned data on endothermic curve of thermogravimetric/differential thermal analysis (heating rate: 5° C./minute) and powder X-ray diffraction spectrum, the formation of the type C crystals of anhydrous aripiprazole was confirmed.

When the type C crystals of anhydrous aripiprazole crystals obtained above were left for 24 hours in a dessicator where the conditions were set at humidity 100%, and temperature 60° C., then the crystals did not exhibit hygroscopicity higher than 0.4% (see, Table 1 below).

Example 12 (Preparation of Type D Crystals of Anhydrous Aripiprazole)

The type-I crystals of anhydrous aripiprazole obtained in Reference Example 2 were added in 200 ml of toluene, and dissolved by heating at 74° C. After confirmed that it was dissolved completely, the toluene solution was cooled to 7° C., and the precipitated crystals were collected by filtration. The crystals were subjected to air-drying as they were so as to obtain 17.9 g (yield: 89.5%) of type D crystals of anhydrous aripiprazole.

The type D crystals of anhydrous aripiprazole obtained above had an endothermic curve substantially identical to the endothermic curve of thermogravimetric/differential thermal analysis (heating rate: 5° C./minute) shown in FIG. 13. Specifically, it had the endothermic peaks at about 136.8° C. and about 141.6°.

The type D crystals of anhydrous aripiprazole obtained above exhibited $^1$H-NMR spectrum (DMSO-d$_6$, TMS) which was substantially identical to the $^1$H-NMR spectrum (DMSO-d$_6$, TMS) shown in FIG. 14. Specifically, they had the characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H), and 10.00 ppm (s, 1H).

The type D crystals of anhydrous aripiprazole obtained above had a powder X-ray diffraction spectrum which was substantially identical to the powder X-ray diffraction spectrum shown in FIG. 15. Specifically, it had the characteristic peaks at 2θ=8.7°, 11.6°, 16.3°, 17.7°, 18.6°, 20.3°, 23.4° and 25.0°.

The type D crystals of anhydrous aripiprazole obtained above had an IR spectrum which was substantially identical to the IR (KBr) spectrum shown in FIG. 16. Specifically, it had the characteristic infrared absorption bands at 2946, 1681, 1375, 1273, 1175 and 862 cm$^{-1}$.

The type D crystals of anhydrous aripiprazole obtained above exhibited a solid $^{13}$C-NMR spectrum which was substantially identical to the solid $^{13}$C-NMR spectrum shown in FIG. 17. Specifically, it had the characteristic peaks at 32.1 ppm, 62.2 ppm, 66.6 ppm, 104.1 ppm, 152.4 ppm, 158.5 ppm and 174.1 ppm.

According to the above-mentioned data on the endothermic curve of thermogravimetric/differential thermal analysis (heating rate: 5° C./minute) and powder X-ray diffraction spectrum, the formation of type D crystals of anhydrous aripiprazole was confirmed.

When the type D crystals of anhydrous aripiprazole crystals obtained above were left for 24 hours in a dessicator where the conditions were set at humidity 100%, and temperature 60° C., the crystals did not have hygroscopicity higher than 0.4% (see, Table 1 below).

Example 13 (Preparation of Type D Crystals of Anhydrous Aripiprazole)

1,200 Grams of the type-I crystals of anhydrous aripiprazole obtained in Reference Example 2 were dissolved in 18 liters of toluene, with heating. This toluene solution was cooled to 40° C., and 36 g of type-D crystals of anhydrous aripiprazole obtained in Example 12 were added as seed crystals, then the solution was cooled to 10° C. and allowed to stand as it is. The precipitated crystals were collected by filtration, dried at 60° C. for 18 hours to obtain 1,073 g (yield: 86.8%) of type D crystals of anhydrous aripiprazole (purity: 100%). The crystals were colorless plate form.

The type D crystals of anhydrous aripiprazole had an endothermic curve substantially identical to the endothermic curve of thermogravimetric/differential thermal analysis (heating rate: 5° C./minute) shown in FIG. 13. Specifically, it had the endothermic peaks around about 136.8° C. and about 141.6°.

The type D crystals of anhydrous aripiprazole obtained above exhibited an $^1$H-NMR spectrum (DMSO-d$_6$, TMS) which was substantially identical to the $^1$H-NMR spectrum (DMSO-d$_6$, TMS) shown in FIG. 14. Specifically, it had the characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H), and 10.00 ppm (s, 18).

The type D crystals of anhydrous aripiprazole obtained above had a powder X-ray diffraction spectrum which was substantially identical to the powder X-ray diffraction spectrum shown in FIG. 15. Specifically, it had the characteristic peaks at 2θ=8.7°, 11.6°, 16.3°, 17.7°, 18.6°, 20.3°, 23.4° and 25.0°.

The type D crystals of anhydrous aripiprazole obtained above had an IR spectrum which was substantially identical to the IR (KBr) spectrum shown in FIG. 16. Specifically, it had characteristic infrared absorption bands at 2946, 1681, 1375, 1273, 1175 and 862 cm$^{-1}$.

The type D crystals of anhydrous aripiprazole obtained above had a solid $^{13}$C-NMR spectrum which was substantially identical to the solid $^{13}$C-NMR spectrum shown in FIG. 17. Specifically, it had the characteristic peaks at 32.1 ppm, 62.2 ppm, 66.6 ppm, 104.1 ppm, 152.4 ppm, 158.5 ppm and 174.1 ppm.

According to the above-mentioned data on the endothermic curve of thermogravimetric/differential thermal analysis (heating rate: 5° C./minute) and powder X-ray diffraction spectrum, the formation of type D crystals of anhydrous aripiprazole was confirmed.

When the type D crystals of anhydrous aripiprazole crystals obtained above were left for 24 hours in a dessicator where the conditions were set at humidity 100%, and temperature 60° C., the crystals did not exhibit hygroscopicity higher than 0.40 (see, Table 1 below).

Example 14 (Preparation of Type E Crystals of Anhydrous Aripiprazole)

40 Grams of type-I crystals of anhydrous aripiprazole obtained in Reference Example 2 was dissolved in 1000 ml of acetonitrile with heating at 80° C. This acetonitrile solution was cooled to about 70° C. by taking for about 10 minutes, and was kept at this temperature for about 30 minutes to precipitate the seed crystals. Next, the temperature of said solution was slowly risen to 75° C., and the crystals were grown up by keeping this temperature for 1 hour. Then, the solution was cooled to 10° C. by taking about 4 hours, and the precipitated crystals were collected by filtration. Thus obtained crystals were subjected to air-drying overnight, there were obtained 37.28 g (yield: 93.2%) of type E crystals of anhydrous aripiprazole (purity: 100%). The melting point of these crystals was 145° C., and the crystals were colorless needle form.

The type E crystals of anhydrous aripiprazole had an endothermic curve substantially identical to the endothermic curve of thermogravimetric/differential thermal analysis (heating rate: 5° C./minute) shown in FIG. 18. Specifically, it had endothermic peak at about 146.5°.

The type E crystals of anhydrous aripiprazole obtained above exhibited an $^1$H-NMR spectrum (DMSO-$d_6$, TMS) which was substantially identical to the $^1$H-NMR spectrum (DMSO-$d_6$, TMS) shown in FIG. 19. Specifically, it had the characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H), and 10.00 ppm (s, 1H).

The type E crystals of anhydrous aripiprazole obtained above had a powder X-ray diffraction spectrum which was substantially identical to the powder X-ray diffraction spectrum shown in FIG. 20. Specifically, it had the characteristic peaks at 2θ=8.0°, 13.7°, 14.6°, 17.6°, 22.5° and 24.0°.

The type E crystals of anhydrous aripiprazole obtained above had an IR spectrum which was substantially identical to the IR (KBr) spectrum shown in FIG. 21. Specifically, it had the characteristic infrared absorption bands at 2943, 2817, 1686, 1377, 1202, 969 and 774 cm$^{-1}$.

According to the data on endothermic curve of thermogravimetric/differential thermal analysis (heating rate: 5° C./minute) and powder X-ray diffraction spectrum, the formation of type E crystals of anhydrous aripiprazole was confirmed.

When the type E crystals of anhydrous aripiprazole obtained above were left for 24 hours in a dessicator where the conditions were set at humidity 1005, and temperature 60° C., the crystals did not exhibit hygroscopicity higher than 0.4% (see, Table 1 below).

Example 15 (Preparation of Type F Crystals of Anhydrous Aripiprazole)

140 Grams of type-I crystals of anhydrous aripiprazole obtained in Reference Example 2 were suspended in 980 ml of acetone and continued to reflux for 7.5 hours with stirring. Next, the suspension was filtered in hot condition, and crystals separated out were subjected to air-drying for 16 hours at room temperature, there was obtained 86.19 g (yield: 61.6%) of type F crystals of anhydrous aripiprazole (purity: 100%). The crystals were colorless prism form.

The type F crystals of anhydrous aripiprazole had an endothermic curve substantially identical to the endothermic curve of thermogravimetric/differential thermal analysis (heating rate: 5° C./minute) shown in FIG. 22. Specifically, it had the exothermic peaks at about 137.5° C. and about 149.8° C.

The type F crystals of anhydrous aripiprazole obtained above exhibited an $^1$H-NMR spectrum (DMSO-$d_6$, TMS) which was substantially identical to the $^1$H-NMR spectrum (DMSO-$d_6$, TMS) shown in FIG. 23. Specifically, it had the characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H), and 10.00 ppm (s, 1H).

The type F crystals of anhydrous aripiprazole obtained above had a powder X-ray diffraction spectrum which was substantially identical to the powder X-ray diffraction spectrum shown in FIG. 24. Specifically, it had the characteristic peaks at 2θ=11.3°, 13.3°, 15.4°, 22.8°, 25.2° and 26.9°.

The type F crystals of anhydrous aripiprazole obtained above had an IR spectrum which was substantially identical to the IR (KBr) spectrum shown in FIG. 25. Specifically, it had the characteristic infrared absorption bands at 2940, 2815, 1679, 1383, 1273, 1177, 1035, 963 and 790 cm$^{-1}$ According to the data on endothermic curve of thermogravimetric/differential thermal analysis (heating rate: 5° C./minute) and powder X-ray diffraction spectrum, the formation of type F crystals of anhydrous aripiprazole was confirmed.

When the type F crystals of anhydrous aripiprazole crystals obtained above were left for 24 hours in a dessicator where the conditions were set at humidity 100%, and temperature 60° C., the crystals did not exhibit hygroscopicity higher than 0.49 (see, Table 1 below).

TABLE 1

| Sample | Initial Moisture Content (%) | Moisture Content After 24 hrs (%) |
|---|---|---|
| Reference Example 1 | 0.04 | 3.28 |
| Reference Example 2 | 0.04 | 1.78 |
| Example 2 | 0.04 | 0.04 |
| Example 3 | 0.02 | 0.02 |
| Example 4 | 0.02 | 0.02 |
| Example 5 | 0.04 | 0.04 |
| Example 6 | 0.04 | 0.04 |
| Example 7 | 0.04 | 0.03 |

TABLE 1-continued

| Sample | Initial Moisture Content (%) | Moisture Content After 24 hrs (%) |
|---|---|---|
| Example 8 | 0.04 | 0.03 |
| Example 9 | 0.03 | 0.01 |
| Example 10 | 0.05 | 0.05 |
| Example 11 | 0.03 | 0.03 |
| Example 12 | 0.04 | 0.03 |
| Example 13 | 0.04 | 0.03 |
| Example 14 | 0.06 | 0.09 |
| Example 15 | 0.04 | 0.04 |

Figure 31:
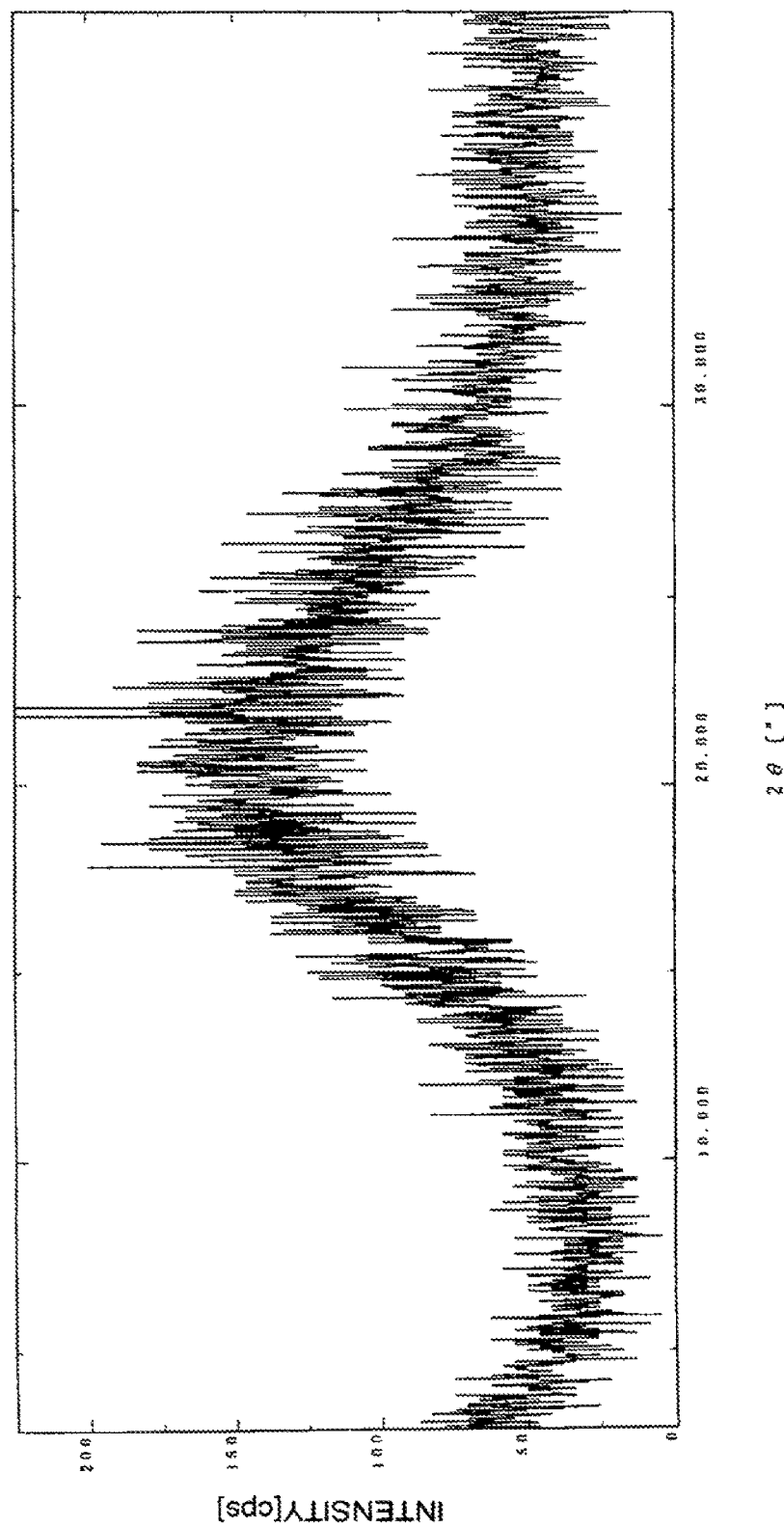
FIG. 31 shows a powder X-ray diffraction spectrum of the glassy state of anhydrous aripiprazole obtained in Example 16-a).

Example 16 a) Type I crystals of anhydrous aripiprazole (10 g) obtained in Reference Example 2 was charged in a stainless steel, round tray (diameter: 80 mm), and heated to about 170° C. so as to melted completely. When this melted liquid was cooled, then it solidified clarity with pale brawn in color, the solid was peeled off from the stainless steel round tray, there was obtained 9.8 g (yield: 98%) of glassy state of anhydrous aripiprazole. The obtained glassy state product was characterized by having no significant peak observed in a powder X-ray determination. (cf. FIG. 31).

Figure 30:
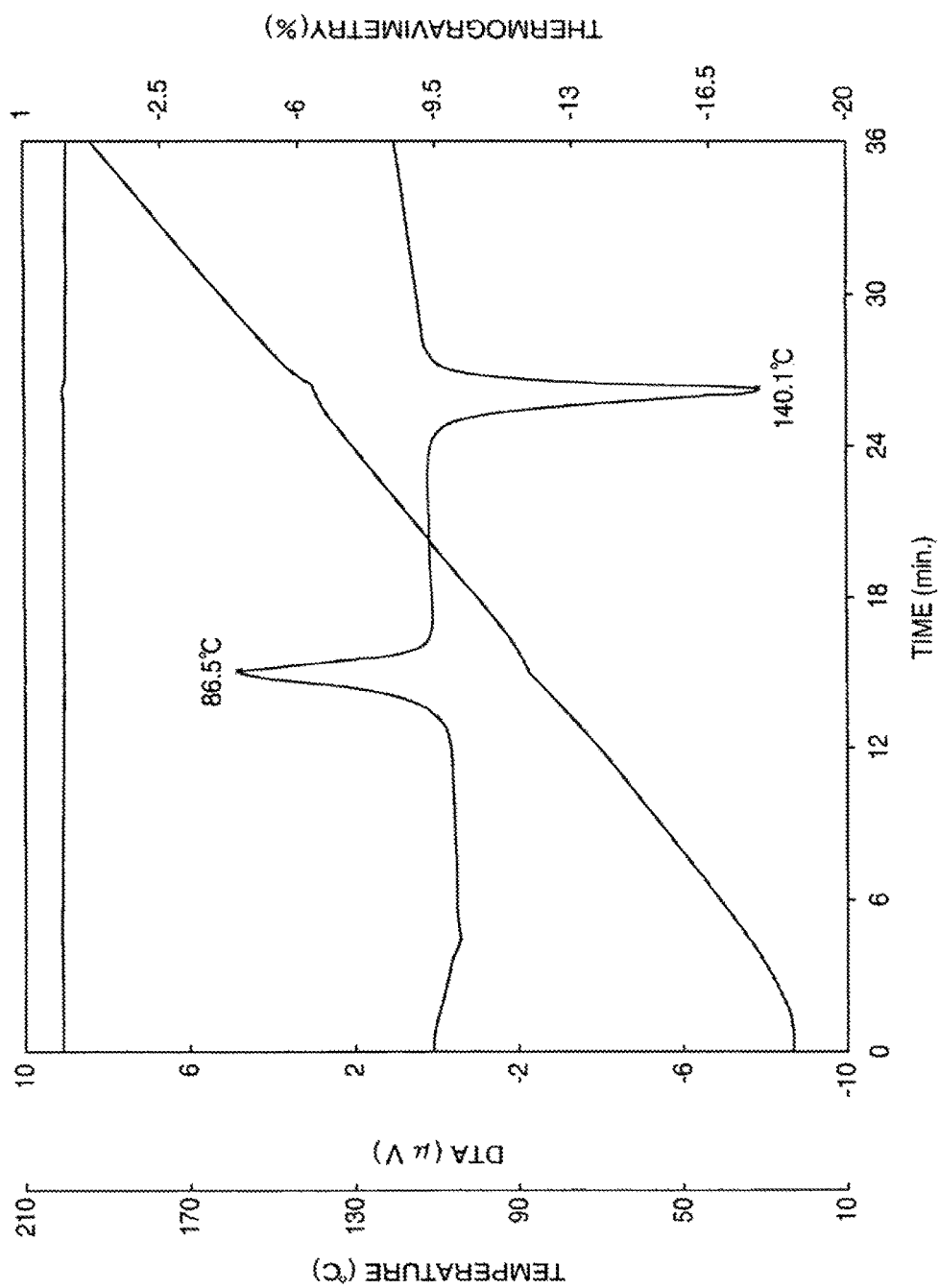
FIG. 30 shows a thermogravimetric/differential thermal analysis endothermic curve of the glass form of anhydrous aripiprazole obtained in Example 16-a).

According to the thermogravimetric/differential thermal analysis (heating rate: 5° C./minute), as shown in FIG. 30, an exothermic peak of type B crystals of anhydrous aripiprazole was observed at around 86.5° C. While, an endothermic peak of type B crystals of anhydrous aripiprazole owing to melting was observed at around 140.1° C.

b) When the glassy state of anhydrous aripiprazole obtained in Example 16-a) were charged in a sealed vessel and left to stand at room temperature for about 6 months, then type G crystals of anhydrous aripiprazole having white in color was obtained by changing the color from pale brown (25 g, yield: 100%). Melting point: 138 to 139° C.

The type G crystals of anhydrous aripiprazole had an endothermic curve which was substantially identical to the thermogravimetric/differential thermal analysis (heating rate: 5° C./min.) endothermic curve shown in FIG. 26, more particularly, it has an endothermic peak around 141.0° C. and an exothermic peak around 122.7° C.

The type G crystals of anhydrous aripiprazole obtained as above exhibited an $^1$H-NMR spectrum which was substantially identical to the $^1$H-NMR spectrum (DMSO-$d_6$, TMS) shown in FIG. 27. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J3=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The type G crystals of anhydrous aripiprazole obtained as above had a powder X-ray diffraction spectrum which was substantially identical to the powder X-ray diffraction spectrum shown in FIG. 28. Specifically, it has characteristic peak at 2θ=10.1°, 12.8°, 15.2°, 17.0°, 17.5°, 19.1°, 20.1°, 21.2°, 22.4°, 23.3°, 24.5° and 25.8°.

The type G crystals of anhydrous aripiprazole obtained above had an IR spectrum which was substantially identical to the IR (KBr) spectrum shown in FIG. 29. Specifically, it has clear infrared absorption bands at 2942, 2813, 1670, 1625, 1377, 1195, 962 and 787 $cm^{-1}$.

Example 17 a) Preparation of Granules of 30 mg Tablets Containing Type B Crystals of Anhydrous Aripiprazole for Additional Drying Type B crystals of anhydrous aripiprazole (1,500 g), lactose (5,700 g), corn starch (1,000 g) and crystalline cellulose (1,000 g) were charged in a fluidized bed granulating dryer (Flow Coater Model FLO-5M; manufactured by FROINT SANGYO KABUSHIKI KAISHA), and these granulating ingredients were mixed by fluidizing for about 3 minutes with an inlet air temperature at 60° C., air flow rate of 3 to 4 m?/min. Further, the granulating ingredients were continued fluidizing under the same condition, and sprayed with about 4,000 g of 5, aqueous solution of hydroxypropyl cellulose to obtain wet granules. The wet granules were dried under an inlet air temperature at 85° C., for about 20 minutes. The obtained dried granules contained 3.8% of water (measured by the method according to Reference Example 4).

b) The Dried Granules (4 kg) Obtained in Example 17-a) were Sized by Use of a Mill (FIORE F-0: Manufactured by TOKUJU CORPORATION).

The sized granules (3 kg) were charged in a fluidized bed granulating dryer (Flow Coater Model FLO-5M; manufactured by FREUND INDUSTRIAL CO., LTD.), and these granulating ingredients were dried under an inlet air temperature at 85° C., and air flow rate of 2 $m^3$/min for 2 hours. The obtained dried granules contained 3.6% of water (measured by the method according to Reference Example 4).

About 1% by weight of magnesium stearate was added to the sized granules and mixed, then the granules were supplied to a tabletting machine (a Rotary single tablet press, Model VIRGO: manufactured by KIKUSUI SEISAKUSHO CO., LTD.), and there were obtained tablets, each having 190 mg of weight.

c) The dried granules (3 kg) obtained in Example 17-a) were charged in a vacuum dryer (vacuum granulating dryer model; VG-50: manufactured by KIKUSUI SEISAKUSHO CO., LTD.), and dried at 70° C. of a jacket temperature, under a reduced pressure at 5 torr of degree of vacuum for 1 hour. The thus obtained dried granules contained 3.1% of water (measured by the method according to Reference Example 4). The dried granules were subjected to sizing by passing to a sieve of 850 μm.

About 1% by weight of magnesium stearate was added to the sized granules and mixed, then the granules were supplied to a tablet machine (Rotary single tablet press, Model VIRGO: manufactured by KIKUSUI SEISAKUSHO CO., LTD.), and there were obtained tablets, each having 190 mg of weight.

Example 18 a) Preparation of 30 mg Tablets Containing Type B Crystals of Anhydrous Aripiprazole Anhydrous aripiprazole (type B crystals) (4,500 g), lactose (17,100 g), corn starch (3,000 g) and crystalline cellulose (3,000 g) were charged in a fluidized bed granulating dryer (NEW-MARUMERIZER Model: NQ-500, manufactured by FUJI PAUDAL CO., LTD.), and these granulating ingredients were mixed by fluidizing for about 3 minutes with an inlet air temperature at 70° C., air flow rate of 10-15 $m^3$/min. Further, the granulating ingredients were continued fluidizing under the same condition, and were sprayed with about 12,000 g of 5 aqueous solution of hydroxypropyl cellulose to obtain wet granules. The wet granules were dried under inlet air at temperature of 85° C., for about 30 minutes. The obtained dried granules contained 3.6% of water (measured by the method according to Reference Example 4). (Yield: 96%). The dried granules were sized by passing to a mill (FIOLE F-0: manufactured by TOKUJU CORPORATION).

About 1% by weight of magnesium stearate was added to the sized granules and mixed, then the granules were supplied to a tablet machine (a Rotary single tablet press, VIRGO: manufactured by KIKUSUI SEISAKUSHO CO., LTD.), and there were obtained tablets, each having 190 mg of weight.

b) The tablets (5 kg) obtained in Example 18-a) were charged in a fan dryer (AQUA COATER AQC-48T, manufactured by FREUND INDUSTRIAL CO., LTD.), and dried under inlet air at temperature of 90° C., air flow rate of 2 m³/min for 6 hours. The obtained dried granules contained 3.3% of water (measured by the method according to Reference Example 4).

c) The dried tablets (3 kg) obtained in Example 18-a) were charged in a vacuum dryer (vacuum granulating dryer, VG-50: manufactured by KIKUSUI SEISAKUSHO CO., LTD.), and dried at 80° C. of a jacket temperature, under reduced pressure of 5 torr of degree of vacuum for 4 hours. The obtained dried tablets contained 2.7% of water (measured by the method according to Reference Example 4).

Example 19 a) By the procedures similar to those of Example 18-a), there were obtained tablets (containing type I crystals of anhydrous aripiprazole obtained in Reference Example 2), each having 190 mg of weight, b) The tablets were dried by the procedures similar to those of Example 18-b), except that air inlet temperature was 100° C. and dried for 1 hour.

c) The tablets were dried by the procedures similar to those of Example 18-b), except that inlet air temperature was 100° C. and dried for 3 hours.

Example 20

By the procedures similar to those of Example 18-a), there were obtained tablets, each having 190 mg of weight, containing type C crystals of anhydrous aripiprazole.

Example 21

By the procedures similar to those of Example 18-a), there were obtained tablets, each having 190 mg of weight, containing type D crystals of anhydrous aripiprazole.

Example 22 a) Aripiprazole hydrate crystals (156 g) obtained in Reference Example 3, lactose (570 g), corn starch (100 g) and crystalline cellulose (100 g) were charged in a fluidized bed granulating dryer (NEW-MARUMERIZER, NQ-160: manufactured by FUJI POWDAL CO., LTD.), and these granulating ingredients were mixed under fluidizing for about 3 minutes with an inlet air temperature at 60° C., air flow rate of 1.0 to 1.5 m³/min, and rotating disc with rotary speed of 400 rpm. Further, the granulating ingredients were continued fluidizing under the same condition, and sprayed about 500 g of 4% aqueous solution of hydroxypropyl cellulose to obtain wet granules. The inlet air temperature was elevated up to 85° C., and dried until the temperature of the product was reached to 46° C. The obtained dried granules were sized by passing to a sieve of 850 μm. The dried granules contained 4.37% of water (measured by the method according to Reference Example 4).

b) The dried granules (200 g) obtained in Example 22-a) were charged in a fluidized bed dryer (multiplex, MP-01: manufactured by POWREX CORPORATION), and dried at 85° C. of inlet air temperature, air flow rate of 0.5 m³/min for 2 hours. The dried granules contained 3.50% of water (measured by the method according to Reference Example 4).

c) The dried granules (100 g) obtained in Example 22-a) were charged in a vacuum dryer (vacuum granulating dryer LCV-232: manufactured by TABAI CO., LTD.), and dried 80° C. of tray temperature, about 760 mmHg of degree of vacuum for 2 hours. The dried granules were further dried similarly for 6 hours. The dried granules contained 3.17% of water (the product being dried for 2 hours: measured by the method according to Reference Example 4). The further dried granules contained 2.88% of water (the product being dried for 6 hours: measured by the method according to Reference Example 4).

d) About 1% by weight of magnesium stearate was added to the sized granules being obtained in Example 22-b) and mixed, then the mixed granules were supplied to a tablet machine (Single type Tablet machine No. 2B: manufactured by KIKUSUI SEISAKUSHO CO., LTD.), and tabletted with punch, there were obtained tablets, each having 191 mg of weight.

e) About 1% by weight of magnesium stearate was added to the sized granules being obtained in Example 22-c) and mixed, then the mixed granules were supplied to a tablet machine (Single type Tablet machine No. 2B: manufactured by KIKUSUI SEISAKUSHO CO., LTD.), and tabletted with punch, there were obtained tablets, each having 191 mg of weight.

Dissolution Test

Each tablets of the pharmaceutical solid oral preparations obtained previously was kept, respectively under the open at 25° C./60V RH for 6 months, and at 40° C./75% RH for 1 week, then their dissolution rates were measured by the following methods. The dissolution rates obtained from 60 minutes after the exposure are shown in Tables 2 and 3. The dissolution rates after 60 minutes, using the tablets kept under the open at 40° C./75% RH for 2 weeks, are shown in Tables 4 and 5. The dissolution rates after 60 minutes, using the tablets kept under the open condition at 40° C./75% RH for 1 week, are shown in Table 6.

Dissolution test equipment: USP

Model: NTR-6100 (manufactured by TOYAMA SANGYO CO., LTD.)

Model: DT-610 (manufactured by JASCO CORPORATION)

a) Method of Dissolution Test of the 15 mg Tablet

One tablet (containing 15 mg each of anhydrous aripiprazole or hydrate) was tested by using 900 ml of acetic acid buffer solution (pH 5.0) (Note: 1) as the test solution, and by rotating a paddle at 100 rpm according to the method of USP (United States Pharmacopoea) (Note: 2).

The test solutions obtained respectively from 10 minutes, 20 minutes, 30 minutes, 45 minutes and 60 minutes after the start of test are named as T10, T20, T30, T45 and T60.

On the other hand, about 0.05 g of standard sample of aripiprazole was weighed accurately, dissolved in ethanol (95%) so as to make exactly 50 ml of ethanol solution. Twenty (20) ml of this ethanol solution was taken accurately, and to prepared exactly 1000 ml of the standard solution by adding 0.01 mol/liter of hydrochloric acid reagent solution (Note: 3).

The test solutions and the standard solution were subjected to filtration, respectively by using a filter having micropores of 10 to 20 μm in diameters, then each of the filtrates were introduced to a spectrophotometer installed with flow cell (cell length: 10 mm), and to measure the absorbance of wave length at 249 nm and absorbance of wave length at 325 nm and determined the differences between absorbances to named as At10, At20, At30, At45, At60 and As, respectively.

After the measurements, the test solutions of T10, T20, T30 and T45 were put back to the test vessels respectively. Further, similar procedures were conducted to other 5 samples of the test solutions.

Dissolution rate (%) relating to the indicated amount of aripiprazole=Amount of the standard sample of aripiprazole (mg)×$At$×$As$×9/5×20/C wherein, At: At10, At20, At30, At45 or At60
As: standard solution
C: Indicated amount of aripiprazole (mg)
(Note: 1) Water was added to 1.97 g of acetic acid (100) and 9.15 g of sodium acetate-trihydrate to make 1000 ml of solution (0.1 mol/l).
(Note: 2) Paddle method
(Note: 3) Water was added to 100 ml of 0.1 mol/l hydrochloric acid (Note: 4) to make 1000 ml of solution.
(Note: 4) Water was added to 0.9 ml of hydrochloric acid to make 1000 ml of solution.

b) Method of Dissolution Test of the 30 mg Tablet

One tablet each of the pharmaceutical solid oral preparations (containing 30 mg each of anhydrous aripiprazole or hydrate) was tested by using 900 ml of acetic acid buffer solution (pH 4.5) (Note: 5) as the test solution, and to conduct the test by rotating a paddle at 75 rpm in accordance with the method of USP (United States Pharmacopoea) (Note: 6).

The test solutions obtained respectively from 10 minutes, 20 minutes, 30 minutes 45 minutes and 60 minutes after the start of test, were named as T10, T20, T30, T45 and T60.

On the other hand, about 0.05 g of the standard sample of aripiprazole was weighed accurately, and dissolved in ethanol (95%) so as to made exactly 50 ml of the ethanol solution. Twenty (20) ml of the ethanol solution was taken accurately, and prepared exactly 1000 ml of the standard solution by adding 0.01 mol/liter of hydrochloric acid reagent solution (Note: 7).

The test solutions and standard solution were subjected to filtration, respectively by using a filter having micropores of 10 to 20 μm in diameters, then each of the filtrates were introduced to a spectrophotometer in which a flow cell (cell length: 10 mm) was installed, and measured the absorbance of wave length at 249 nm and absorbance of wave length at 325 nm, and the difference between these absorbances were named as At10, At20, At30, At45, At60 and As, respectively.

After the measurements, the test solutions of T10, T20, T30 and T45 were put back respectively to the test vessels. Further, similar procedures were conducted to other 5 samples of the test solutions.

Dissolution rate (%) relating to the indicated amount of aripiprazole=Amount of the standard sample of aripiprazole (mg)×$At$×$As$×9/5×20/C wherein, At: At10, At20, At30, At45 or At60
As: standard solution
C: Indicated amount of aripiprazole (mg)

(Note: 5) Water was added to 1.91 g of acetic acid (100) and 2.99 g of sodium acetate-trihydrate to made 1000 ml of solution (0.05 mol/l).
(Note: 6) Paddle method
(Note: 7) Water is added to 100 ml of 0.1 mol/l hydrochloric acid (Note: 8) to made 1000 ml of solution.
(Note: 8) Water was added to 0.9 ml of hydrochloric acid to make 1000 ml of solution.

TABLE 2

| Samples used | Open at 25° C./60% RH | | Open at 40° C./75% RH | |
| --- | --- | --- | --- | --- |
| | Initial | After 6 months | Initial | After 1 week |
| Tablet(15 mg) of Reference Example 4 | 83.4% | 44.3% | 83.4% | 44.1% |
| Tablet(15 mg) of Reference Example 5 | 90.1% | 61.9% | 90.1% | 65.2% |

TABLE 3

| Samples used | Open at 25° C./60% RH | | Open at 40° C./75% RH | |
| --- | --- | --- | --- | --- |
| | Initial | After 6 months | Initial | After 1 week |
| Tablet (30 mg) of Example 18-a) | 96.7% | 77.1% | 96.7% | 75.9% |
| Tablet (30 mg) of Example 17-b) | 96.5% | 93.6% | 95.0% | 92.2% |
| Tablet(30 mg) of Example 17-c) | 97.0% | 96.3% | 94.7% | 94.8% |
| Tablet (30 mg) of Reference Example 18-b) | 97.2% | 95.3% | 97.2% | 97.8% |
| Tablet(30 mg) of Reference Example 18-c) | 97.8% | 96.3% | 97.8% | 96.9% |

TABLE 4

| Samples used | Initial | After 2 weeks |
| --- | --- | --- |
| Samples used Tablet (30 mg) of Example 19-a) | 89.8% | 66.9% |
| Tablet (30 mg) of Example 19-b) | — | 79.8% |
| Tablet (30 mg) of Example 19-c) | — | 85.9% |

TABLE 5

| Samples used | Initial | After 2 weeks |
| --- | --- | --- |
| Tablet (30 of Example 18-a) | 94.8% | 94.7% |
| Tablet (30 mg) of Example 20 | 93.7% | 93.1% |
| Tablet (30 mg) of Example 21 | 94.8% | 90.9% |

TABLE 6

| Samples used | Initial | After 1 weeks |
| --- | --- | --- |
| Tablet (30 mg) of Example 22-d) | 96.5% | 84.5% |
| Tablet (30 mg) of Example 22-e) (dreid for 2 hours) | 92.5% | 74.4% |
| Tablet (30 mg) of Example 22-e) (dreid for 6 hours) | 96.2% | 83.4% |

(Note: Dissolution tests in Table 5 were conducted similarly to the procedures in the above-mentioned "b) Method of dissolution test of the 30 mg tablet" except that by using 900 ml of acetic acid buffer solution (pH 4.0) as the test solution, and by rotating a paddle at 50 rpm.

As can be seen clearly from the data shown in Table 2, in comparison with the 15 mg tablet containing conventional anhydrous aripiprazole crystals (Reference Example 4), the 15 mg tablet containing type B crystals of anhydrous aripiprazole (Reference Example 5) had the dissolution rate to maintain maximum drug concentration (Cmax), at pH 5.0 after 60 minutes, even though such tablet was kept under the open at 25° C./60% RH for 6 months and under the open at 40° C./75% RH for 1 week.

As can be seen clearly from the data shown in Table 3, even though 30 mg tablets (Examples 17-b) and 17-c)) prepared from twice dried granules of type B crystals of anhydrous aripiprazole, and 30 mg tablets (Examples 18-b) and 18-c)) prepared from further dried pharmaceutical solid oral preparation containing type B crystals of anhydrous aripiprazole were subjected to keep under the open at 25° C./60% RH for 6 months or 40° C./75% RH for 1 week, the dissolution rates of these tablets obtained 60 minutes after the test at pH 4.5 were not substantially lowered.

As can be seen clearly from the data shown in Table 4, when 30 mg tablets (Examples 19-a), 19-b) and 19-c)) containing conventional anhydrous aripiprazole crystals were further dried and subjected to keep under open at 40° C./75% RH for 2 weeks, then the dissolution rates of the tablets obtained 60 minutes after the test at pH 4.5 were the dissolution rates to maintain maximum drug concentration (Cmax).

As can be seen clearly from the data shown in Table 5, when 30 mg tablet (Example 18-a)) containing type B crystals of anhydrous aripiprazole, 30 mg tablet (Example 20) containing type C crystals of anhydrous aripiprazole and 30 mg tablet (Example 21) containing type D crystals of anhydrous aripiprazole were subjected to keep under open at 40° C./75% RH for 2 weeks, then the dissolution rates of the tablets obtained 60 minutes after the test at pH 4.0 were not substantially lowered.

As can be seen clearly from the data shown in Table 6, when 30 mg tablets (Examples 22-d) and 22-e)) prepared from granules of conventional aripiprazole hydrate being twice dried, and subjected to keep under open at 40° C./75% RH for 1 week, then the dissolution rates of the tablets obtained 60 minutes after the test at pH 4.5 were the dissolution rates to maintain maximum drug concentration (Cmax).

Sample Preparation 1

| Anhydrous aripiprazole crystals B | 5 mg |
|---|---|
| Starch | 131 mg |
| Magnesium stearate | 4 mg |
| Lactose | 60 mg |
| Total | 200 mg |

Tablets containing the above ingredients in each tablet were prepared by formulation methods known to one skilled in the art of pharmaceutical formulation.

Sample Preparation 2

| Type C crystals of anhydrous aripiprazole | 5 mg |
|---|---|
| Starch | 131 mg |
| Magnesium stearate | 4 mg |
| Lactose | 60 mg |
| Total | 200 mg |

In accordance with an ordinary method, tablet preparation, containing the above-mentioned ingredients per 1 tablet was prepared.

Sample Preparation 3

| Type D crystals of anhydrous aripiprazole | 5 mg |
|---|---|
| Starch | 131 mg |
| Magnesium stearate | 4 mg |
| Lactose | 60 mg |
| Total | 200 mg |

In accordance with an ordinary method, tablet preparation, containing the above-mentioned ingredients per 1 tablet was prepared.

Sample Preparation 4

| Type E crystals of anhydrous aripiprazole | 5 mg |
|---|---|
| Starch | 131 mg |
| Magnesium stearate | 4 mg |
| Lactose | 60 mg |
| Total | 200 mg |

In accordance with an ordinary method, tablet preparation, containing the above-mentioned ingredients per 1 tablet was prepared.

Sample Preparation 5

| Type F crystals of anhydrous aripiprazole | 5 mg |
|---|---|
| Starch | 131 mg |
| Magnesium stearate | 4 mg |
| Lactose | 60 mg |
| Total | 200 mg |

In accordance with an ordinary method, tablet preparation, containing the above-mentioned ingredients per 1 tablet was prepared.

Sample Preparation 6

| Type G crystals of anhydrous aripiprazole | 5 mg |
|---|---|
| Starch | 131 mg |
| Magnesium stearate | 4 mg |
| Lactose | 60 mg |
| Total | 200 mg |

In accordance with an ordinary method, tablet preparation, containing the above-mentioned ingredients per 1 tablet was prepared.

Formulation Example

The following examples used aripiprazole drug substance made by first milling or pulverizing the conventional hydrate of aripiprazole and then heating it to form the anhydrous form (anhydrous aripiprazole crystals B).

Formulation Example 1

Flash-melt tablets were prepared as follows:
Intragranulation:

| Ingredient | Percent w/w | Mg. per tablet |
|---|---|---|
| Xylitol (300) Xylisorb | 26 | 52 |
| Avicel ® PH 102 | 12 | 24 |
| Calcium Silicate | 43.35 | 86.7 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 0.25 | 0.5 |
| Total weight | 92.75 | 185.5 |

The ingredients except for the magnesium stearate were blended in a commercial V-blender in geometric proportions for 5 minutes each until all were added. The magnesium stearate was then added and the mixture blended for an additional three minutes. The blended formulation was compacted at a pressure of 30-35 kgF/cm$^2$ in a commercial compactor equipped with an orifice such that the compacts therefrom are in the form of ribbons. The ribbons were passed through a 30 mesh (600 microns) screen to form stable granules of about 150 to 400 microns.
Extragranulation Ingredients:

| Ingredient | Percent w/w | Mg. per tablet |
|---|---|---|
| Intragranulation | 92.75 | 185.5 |
| Avicel ® PH 200 | 3 | 6 |
| Crospovidone | 4 | 8 |
| Magnesium stearate | 0.25 | 0.5 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.3 kP (3.5 SCU) and disintegrated in 10 seconds in 5 ml of water. The final blend formulation demonstrated excellent flow and was free of other problems such as chipping, capping and sticking. It has been found that utilizing Avicel® PH 102 for the intragranulation and Avicel® PH 200 for the extragranulation ingredient enhanced the quality of the resultant tablets.

Formulation Example 2

Flash-melt tablets containing a combination of two grades of calcium silicate were prepared as follows:
Intragranulation:

| Ingredient | Percent w/w | Mg. per tablet |
|---|---|---|
| Xylitol (300) Xylisorb | 26 | 52 |
| Avicel ® PH 102 | 12 | 24 |
| Calcium Silicate (crystalline, alpha triclinic) | 33.35 | 66.7 |
| Hubersorb 600 NF (amorphous calcium silicate) | 10 | 20 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 0.25 | 0.5 |
| Total weight | 92.75 | 185.5 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Formulation Example 1.
Extragranulation Ingredients:

| Ingredient | Percent w/w | Mg. per tablet |
|---|---|---|
| Intragranulation | 92.75 | 185.5 |
| Avicel ® PH 200 | 3 | 6 |
| Crospovidone | 4 | 8 |
| Magnesium stearate | 0.25 | 0.5 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.0 kP (3.1 SCU) and disintegrated in 10 seconds in 5 ml of water.

Formulation Example 3

Flash-melt tablets containing aripiprazole, an antischizophrenic drug, were prepared as follows:
Intragranulation

| Ingredient | Percent w/w | Mg. per tablet |
|---|---|---|
| Aripiprazole | 15 | 30 |
| Xylitol (300) Xylisorb | 25 | 50 |
| Avicel ® PH 102 | 6 | 12 |
| Calcium Silicate | 37 | 74 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 00.25 | 0.5 |
| Total weight | 94.4 | 188.8 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Formulation Example 1.

Extragranulation Ingredients:

| Ingredient | Percent w/w | Mg. per tablet |
|---|---|---|
| Intragranulation | 94.4 | 188.8 |
| Avicel ® PH 200 | 1.1 | 2.2 |
| Crospovidone | 4 | 8 |
| Magnesium stearate | 0.5 | 1 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.0 kP (3.1 SCU) and disintegrated in 10 seconds in 5 ml of water.

Formulation Example 4

Flash-melt tablets containing aripiprazole were prepared as follows:
Intragranulation:

| Ingredient | Percent w/w | Mg. per tablet |
|---|---|---|
| Aripiprazole | 0.5 | 1 |
| Xylitol (300) Xylisorb | 27 | 54 |
| Avicel ® PH 102 | 12 | 24 |
| Calcium Silicate | 42 | 84 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 0.25 | 0.5 |
| Total weight | 92.9 | 185.8 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Formulation Example 1.
Extragranulation Ingredients:

| Ingredient | Percent w/w | Mg. per tablet |
|---|---|---|
| Intragranulation | 92.9 | 185.8 |
| Avicel ® PH 200 | 2.6 | 5.2 |
| Crospovidone | 4 | 8 |
| Magnesium stearate | 0.5 | 1 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.3 kP (3.5 SCU) and disintegrated in 10 seconds in 5 ml of water.

The invention claimed is:

1. A process for preparing Anhydrous Aripiprazole Crystals B having low hygroscopicity, wherein said process comprises:
   heating Hydrate A of aripiprazole,
   wherein said low hygroscopicity is defined as a moisture content of 0.40% or less when the Anhydrous Aripiprazole Crystals B are placed for 24 hours in a dessicator maintained at a temperature of 60° C. and a humidity level of 100%.

2. The process according to claim 1, wherein said process comprises heating Hydrate A of aripiprazole at 90-125° C. for about 3-50 hours.

3. The process according to claim 1, wherein said process comprises heating Hydrate A of aripiprazole at 100° C. for about about 18 hours.

4. The process according to claim 1, wherein said process comprises heating Hydrate A of aripiprazole at 100° C. for about about 24 hours.

5. The process according to claim 1, wherein said process comprises heating Hydrate A of aripiprazole at 120° C. for about about 3 hours.

6. The process according to claim 1, wherein said process comprises heating Hydrate A of aripiprazole for about 18 hours at 100° C. followed by additional heating for about 3 hours at 120° C.

7. A process for preparing Anhydrous Aripiprazole Crystals B having low hygroscopicity, wherein said process comprises:
   heating Hydrate A of aripiprazole,
   wherein said low hygroscopicity is defined as a moisture content of 0.10% or less when the Anhydrous Aripiprazole Crystals B are placed for 24 hours in a dessicator maintained at a temperature of 60° C. and a humidity level of 100%.

8. The process according to claim 7, wherein said process comprises heating Hydrate A of aripiprazole at 90-125° C. for about 3-50 hours.

9. The process according to claim 7, wherein said process comprises heating Hydrate A of aripiprazole at 100° C. for about about 18 hours.

10. The process according to claim 7, wherein said process comprises heating Hydrate A of aripiprazole at 100° C. for about about 24 hours.

11. The process according to claim 7, wherein said process comprises heating Hydrate A of aripiprazole at 120° C. for about about 3 hours.

12. The process according to claim 7, wherein said process comprises heating Hydrate A of aripiprazole for about 18 hours at 100° C. followed by additional heating for about 3 hours at 120° C.

* * * * *